(12) United States Patent
Lederman et al.

(10) Patent No.: US 6,610,294 B1
(45) Date of Patent: *Aug. 26, 2003

(54) METHODS OF INHIBITING AN AUTOIMMUNE RESPONSE IN A HUMAN SUFFERING FROM AN AUTOIMMUNE DISEASE BY ADMINISTERING AN ANTIBODY THAT BINDS TO A PROTEIN TO WHICH MONOCLONAL ANTIBODY 5C8 BINDS

(75) Inventors: Seth Lederman, New York, NY (US); Leonard Chess, Scarsdale, NY (US); Michael J. Yellin, Riverdale, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/244,087

(22) PCT Filed: Nov. 16, 1992

(86) PCT No.: PCT/US92/09955
§ 371 (c)(1),
(2), (4) Date: Oct. 20, 1994

(87) PCT Pub. No.: WO93/09812
PCT Pub. Date: May 27, 1993

Related U.S. Application Data

(63) Continuation-in-part of application No. 07/792,728, filed on Nov. 15, 1991, now Pat. No. 5,474,771.

(51) Int. Cl.[7] ........................ A61K 39/395; C07K 16/28
(52) U.S. Cl. .................. 424/154.1; 424/130.1; 424/133.1; 424/141.1; 424/143.1; 424/153.1; 424/173.1; 424/178.1; 424/188.1; 424/183.1; 530/387.4; 530/387.3; 530/388.1; 530/388.22; 530/388.7; 530/388.73; 530/388.75; 530/391.3; 530/391.7
(58) Field of Search ................... 424/1.49, 130.1, 424/141.1, 152.1, 172.1, 181.1; 435/326, 343, 346, 7.1, 7.2, 7.21, 7.23; 530/387.1, 388.22, 388.75, 387.3

(56) References Cited

U.S. PATENT DOCUMENTS

| | | |
|---|---|---|
| 5,102,909 A | 4/1992 | Veltri et al. |
| 5,340,829 A | 8/1994 | Clark et al. |
| 5,474,771 A | 12/1995 | Lederman et al. |
| 5,683,693 A | 11/1997 | Noelle et al. |
| 5,747,037 A | 5/1998 | Noelle et al. |
| 5,833,987 A | 11/1998 | Noelle et al. |
| 5,961,974 A | 10/1999 | Armitage et al. |

FOREIGN PATENT DOCUMENTS

| | | |
|---|---|---|
| EP | 0555880 | 8/1993 |
| WO | 9308207 | 4/1993 |
| WO | WO 9506480 | 3/1995 |
| WO | WO 9623071 | 8/1996 |
| WO | WO 9830240 | 7/1998 |
| WO | WO 9830241 | 7/1998 |

OTHER PUBLICATIONS

Bach Tips 14: 213–216 (1993).*
Resetkova et al. Thyroid 6: 267–273 (1996).*
Seachrist Bioworld Today 10(204):1,3, Oct. 25, 1999.*
Press Release From IDEC Pharmaceuticals, Inc. Apr. 20, 2000 (See IDEC–131).*
Paul (Ed) Fundamental Immunology Raven Press NY 1993 p. 242 only.*
Jain Scientific American Jul. 1994 pp. 58–65.*
Gray et al. J Exp Med. 180: 141–155 (1994).*
Stuber et al. J Exp Med 183: 693–698 (1996).*
Biacone et al. Kidney Intl. 48: 458–468 (1996).*
Lauerna Biodrugs 8: 96–106 (1997).*
Nickoloff et al. J. Immunol. 150: 2148–2159 (1993).*
Kover KL, et al., Anti–CD154 (CD40L) prevents recurrence of diabetes in islet isografts in the DR–BB rat. *Diabetes* Oct. 2000; 49(10):1666–70.
Seung E, et al., Allogenic hematopoietic chimerism in mice treated with sublethal myeloablation and anti–CD154 antibody: absence of graft–versus–host disease, induction of skin allograft tolerance, and prevention of recurrent autoimmunity in islet–allografted NOD/Lt mice *Blood* Mar. 15, 2000; 95(6):2175–82.
Mandik–Nayak L, et al., Functional consequences of the developmental arrest and follicular exclusion of anti–double–stranded DNA B cells. *J Immunol* Feb. 1, 2000;164(3):1161–8.
McCormick AL, et al., Cell surface expression of CD154 inhibits alloantibody responses: A mechanism for the prevention of autoimmune responses against activated T cells? *Cell Immunol* Aug. 1, 1999; 195(2):157–61.
Biancone L, et al., CD40–CD154 interaction in experimental and human disease (review). *Int J Mol Med* Apr. 1999; 3(4):343–53.
Press Release from Biogen, Inc., dated Oct. 21, 1999, "Biogen Says It Has Halted Several Trials of Anti–CD40 Ligand Monoclonal Antibody".
Press Release from Biogen, Inc., dated Nov. 2, 1999, "Biogen Says It Has Stopped Ongoing Tirals of Anti–CD40 Ligand Monoclonal Antibody".

(List continued on next page.)

Primary Examiner—Phillip Gambel
(74) Attorney, Agent, or Firm—John P. White; Cooper & Dunham LLP

(57) ABSTRACT

This invention provides a method of inhibiting an autoimmune response in an animal suffering from an autoimmune disease selected from the group consisting of psoriasis, Lyme disease and hyper IgE syndrome which comprises administering to the animal, in an amount effective to treat the autoimmune disease, an antibody that binds specifically to a protein specifically recognized by monoclonal antibody 5c8 produced by the hybridoma having ATCC Accession No. HB 10916.

16 Claims, 42 Drawing Sheets

OTHER PUBLICATIONS van Essen et al. (1995), 378 *Nature* 620–623.
Kirk et al. (1999) *Nature Medicine* 5(6):686–693.
Allen, et al. (1993) CD40 ligand gene defects responsible for X–linked hyper–IgM syndrome, *Science* 259(5097):990–3.
Kirk, A.D. and Harlan, D.M. (2000) Reply to Thromboembolic Complications After Treatment With Monoclonal Antibody Against CD40 Ligand, *Nature Medicine*, 6(2): 115.
Strom T.B. et al. 1989, "Toward More Selective Therapies to Block Undesired Immune Responses", *Kidney International* 35(4):1026–1033.
Yellin M.J. et al. 1991, "A Human CD4 Negative T–Cell Leukemia Cell Sublcone with Contact–Dependent Helper Function", *Journal of Immunology* 147(10):3389–3395.
Lederman S. et al. 1992, "Anti–CD40 Monoclonal Antibody Blocks the Contact Dependent T Helper Signal Medicated by 5c8 Antigen", *Clinical Research* 40(2):154A.
Waldmann, T.A., *Science* (1991) 252:1657–1662.
Cunningham, C., et al., *TIBTECH* (1992) vol. 10.
Rogozinski, et al., *J. Immunol.* (1984) 132:735–739.
Dillman, R.O., *Annals Int. Med.* (1989) 111:592–603.
Weiss, et al., *Adv. Immunol.* (1987) 41:1–38.
Harris, W., et al., *TIBTECH* (1993) 11:42–44.
Lederman, et al., *J. Exp. Med.* (1992) 175:1091–1101.
Joliffe, L.K.., *Intern. Rev. Immunol.* (1993) 10:241–250.
Borrebaeck, C.A.K., et al., *Immunol. Today* (1993) 14:477–482.
Kahan, B., *Current Opin. Immunol.* (1992) 4:553–560.
Tueveson, G., et al., *Immunol. Rev.* (1993) Issue No. 136:99–109.
Emery, S.C., et al., *Exp. Opin. Invest. Drugs* (1994) 3:241–251.
Winter, G., et al., *TIPS* (1993) 14:139–143.
Borst, J., et al., *Eur. J. Immunol.* (1989) 19:357–364.
Brian, A., *Proc. Natl. Acad. Sci. USA* (1988) 85:564–568.
Crow, M.K., et al., *Cell. Immunol.* (1989) 121:99–112.
Damle, N.K., et al., *Eur. J. Immunol.* (1991) 21:1277–1282.
Hirohata, S., et al., *J. Immunol.* (1988) 140(11):3726–3744.
Hodgkin, P.D., et al., *J. Immunol.* (1990) 145:2025–2034.
Kubota, E., et al., *Immunol.* (1991) 72:40–47.
Noelle, R.J., et al., *J. Immunol.* (1989) 143(6):1807–1814.
Noelle, R.J., et al., *J. Immunol.* (1991) 146(4):1118–1124.
Rabin, E.M., et al., *Proc. Natl. Acad. Sci. USA* (1985) 82:2935–2939.
Reinherz, E.L., et al., *J. Exp. Med.* (1979) 150:1472–1482.
Sanders, V.M., et al., *J. Immunol.* (1986) 137(8):2395–2404.
Sekita, K., et al., *Eur. J. Immunol.* (1988) 18:1405–1410.
Smith, S.H., et al., *Immunol.* (1986) 58:63–70.
Tohma, S., Hirohata, S., and Lipsky, P.E., *J. Immunol.* (1991)146 (2):492–499.
Tohma, S., and Lipsky, P.E., *J. Immunol.* (1991) 146(8):2544–2552.
Torimoto, Y., et al., *J. Immunol.* (1991) 146(7):2176–2184.
R.J. Armitage et al., *Nature* (1992) 357:80–82.
P. Lane et al., *Eur. J. Immunol.* (1992) 22:2573–2578.
L.S. Marshall and R.J. Noelle, *FASEB J.* (1991) 5(4):A608; Abstract No. 1379.
R.J. Noelle et al., *Proc. Natl. Acad. Sci. USA* (1991) 89:6550–6554.
R.J. Noelle et al., *Immunol. Today*, (1992) 13(11):431–433.
R.J. Noelle and E.C. Snow, *FASEB J.* (1991) 5(13):2770–2776.
R. Noelle and E.C. Snow, *Current Opinion in Immunology*, (1992) 333–337.

R.J. Noelle et al., in *Mechanisms of Lymphocyte Activation and Immune Regulation IV: Cellular Communications*, S. Gupta and T.A. Waldmann, eds. (Plenum, New York 1992) 131–137.
Akdis et al. (1997) *Eur. J. Immunol.* 27:2351–2357.
Bartlett, W.C., et al. (1990). *J. Immunol.* 145:3956–3962.
Callard et al. (1993) *Imm. Today* 14:559–564.
Christadoss, P. and Dauphinee, M.J. (1986) *J. Immunol.*136:2437–2440.
Clark, E.A. and Ledbetter, J.A. (1986) *Proc. Natl. Acad. Sci. USA* 83: 4494–4498.
Cosimi A.B. et al (1981) *Transplant Proc* 13:499–503.
Durie et al. (1994) *J. Clin. Invest.* 94:1333–38.
Edington et al. (1993) *Biotech.* 11:998–1000.
Freeman, G.J., et al.(1991). *J. Exp. Med.*174:625–631.
Gascan H. et al. (1991) *J. Immunol* 147:8–13.
Goldberg D. et al. (1991) *J. Autoimmun.* 4:617–630.
Gordon J. et al. (1988) *J. Immunol.* 140:1425–1430.
Hafler D.A. (1988) *J. Immunol* 141:131–138.
Haynes M. K. et al. (1987) *Diabetes* 36:877–881.
Horneff G. et al. (1991) *Arthritis & Rheum.* 34:129–140.
Jenkins M.K. et al. (1987) *J. Exp. Med.* 165:302–319.
Junghans R.P. (1990) *Cancer Res.* 50:1495–1502.
Kennedy M.K .(1987) *J. Neuroimmunol.* 16:345–364.
Koike T. (1987) *Diabetes* 36:539–541.
Kung P.C. et al. (1979) *Sci.* 206:347–349.
Kung P.C. et al. (1980) *Vox. Sang.* 39:121–127.
Lederman S. et al. (1994) *Res. in Imm.* 145(3):215–221.
Lenz et al. (1993) *J. Clin. Invest.* 92:2587–2596.
Ling N.R. (1987) A.J. Michaels ed p302–35.
Linsley P.S. et al. (1991) *J. Exp. Med.* 174:561–569.
Madec A.M. et al. (1996) *J. Immunol.* 156:3541–3549.
Marshall L. S. et al. (1990) *Res. Immunol.* 141:412–417.
Noelle R.J. et al (1996) *Immunity* 4:415–19.
Noelle R. (1990) *Imm.Today* 11(10):361–68.
Paul (Ed) *Fund. Imm.*, Third Edition Raven Press p242, 1993.
Pisetsky D.S. (1985) in Pincus S.H. et al eds. p171–76, Biologically Based Immuno Modulators in the Therapy of Rheumatic Diseases, Elsevier, New York.
Potocnik A.J. et al. (1990) *Scand. J. Immunol.* 31:213–224.
Ranges G.E. et al. (1985) *J. Exp. Med.*162:1105–1110.
Reinherz E.L. et al. (1979) *J. Exp. Med.*150:1472–1482.
Reiter C. et al. (1991) *Arthritis & Rheum.* 34:525–36.
Satoh J. et al. (1988) *J. Neuroimmunol.*18:105–116.
Schwarz R.H. et al. (1990) *Sci.* 248:1349–1356.
Shizuru J.A. et al. (1988) *Sci.* 240659–662.
Snow E. C. et al. (1989) *Fed. Am. Soc. for Exp. Bio.* 73$^{rd}$ meeting Abs no.4267.
Sriram S. et al. (1986) *J. Immunol.* 136:4464–69.
Stull S.J. at al. (1988) *Cell Immunol.* 117:188–98.
Traugott U. (1983) *Science* 219:308–310.
Traugott U. (1983) *J. Neuroimmunol.* 4:201–21.
Valent P. et al. (1990) *Int. Arch. Allergy. Appl. Immunol.*91:198–203.
van Seventer G.A. et al. (1990)*J. Immunol.* 144:4579–4586.
Waldmann H. et al. (1989) *Ann. Rev. Immunol.* 7:407–444.
Waldor M.K. et al (1985) *Sci.* 227:415–17.
Williams I.R. et al. (1990) *J. Immunol.* 145:85–93.
Wofsy, D., et al. (1985). *J. Immunol.*134:852–857.
Wofsy, D. and Seaman, W.E. (1985). (S.H. Pincus, et al. eds.), pp. 187–195 Biologically Based Immunomodulators in the Therapy of Rheumatic Diseases, Elsevier, New York.

Wofsy, D. and Seaman, W.E. (1985). *J. Exp.Med.* 161:378–391.

Wofsy, D. and Seaman, W.E. (1987). *J. Immunol.* 138:3247–3253.

Wofsy, D. (1986). *J. Immunol.* 136:4554–4560.

Wofsy, D. and Carteron, N.L. (1990). *Semin. Immunol.* 2:419–425.

Young, L.S., et al. (1989) *Int. J. Cancer* 43:786–794.

* cited by examiner

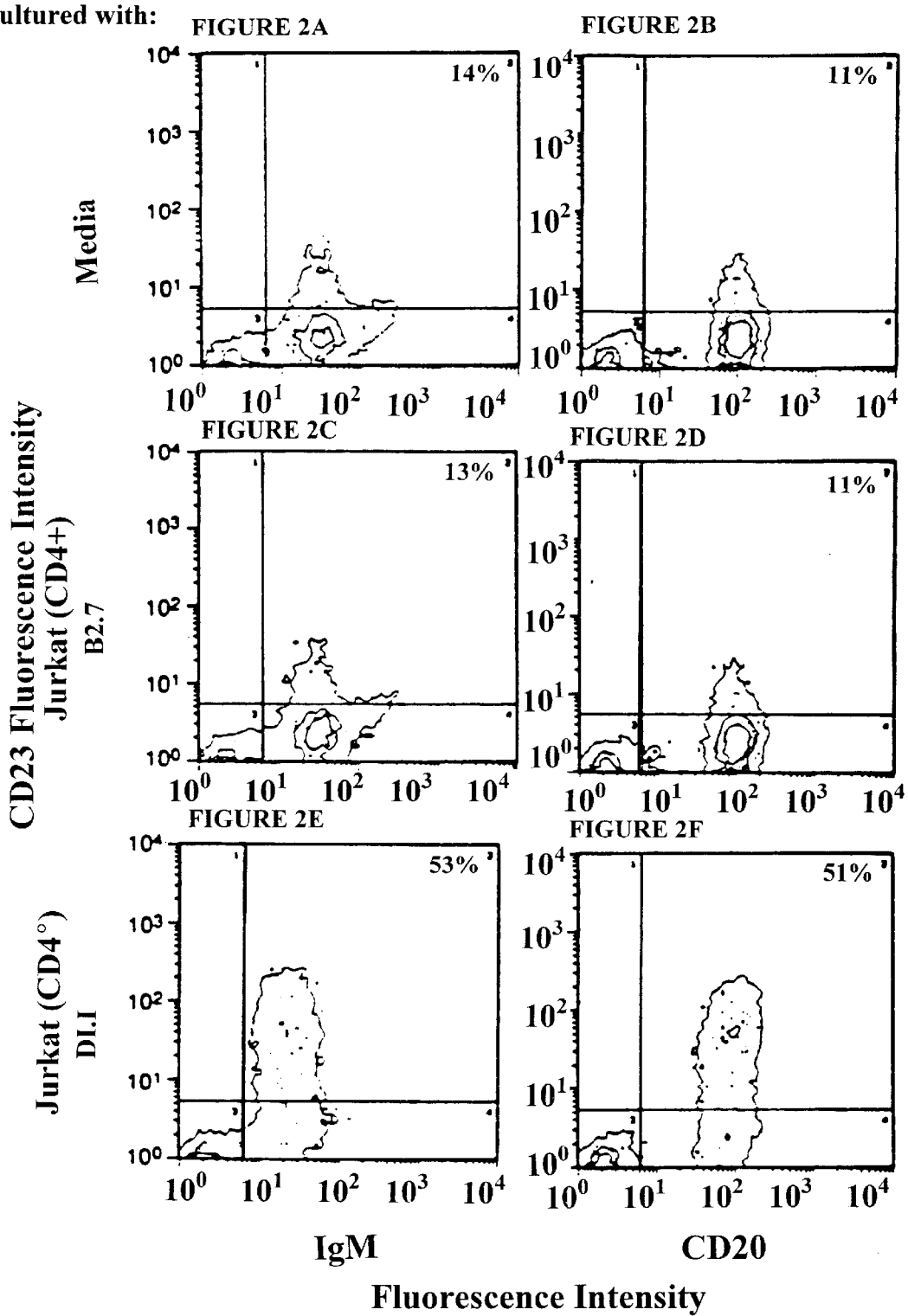

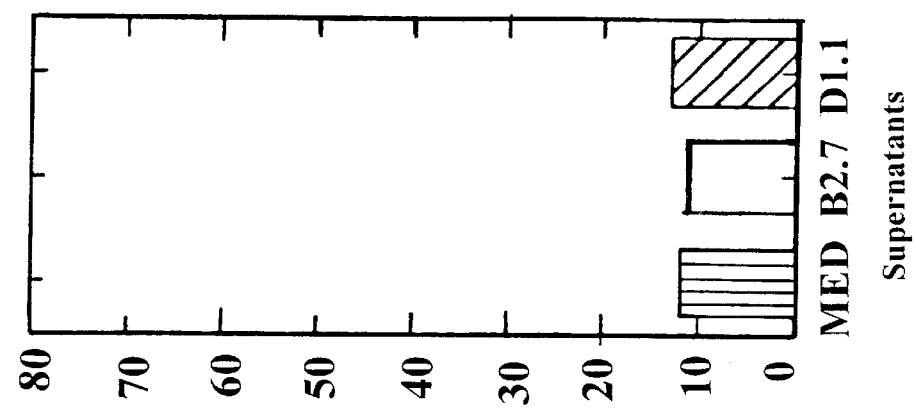
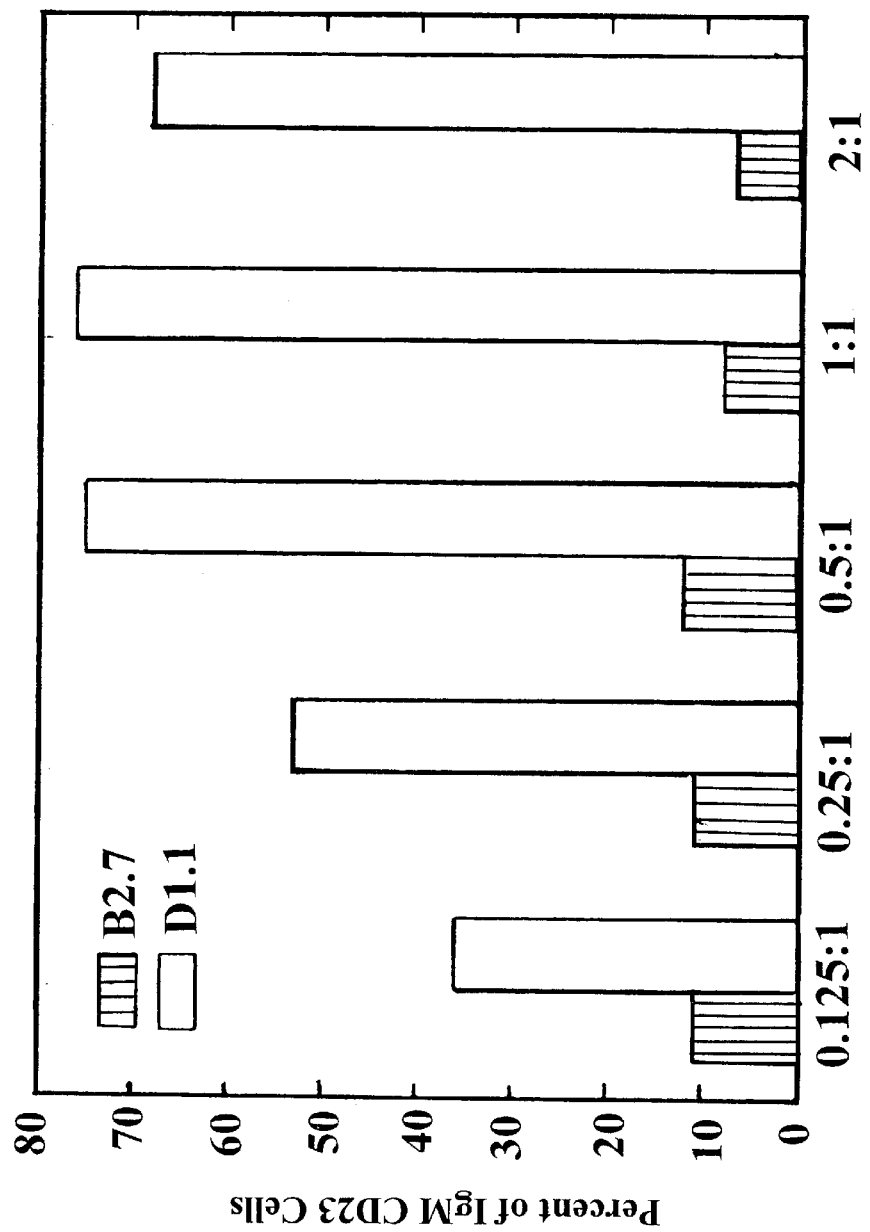
FIGURE 3B
FIGURE 3A

FIGURE 5A
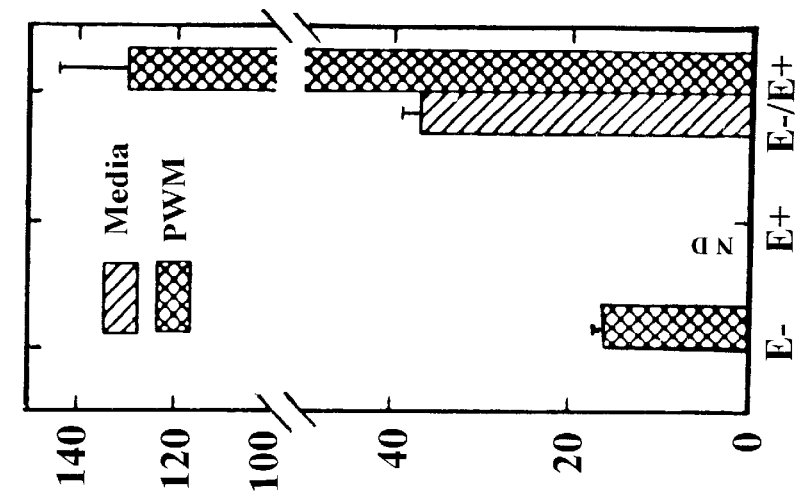
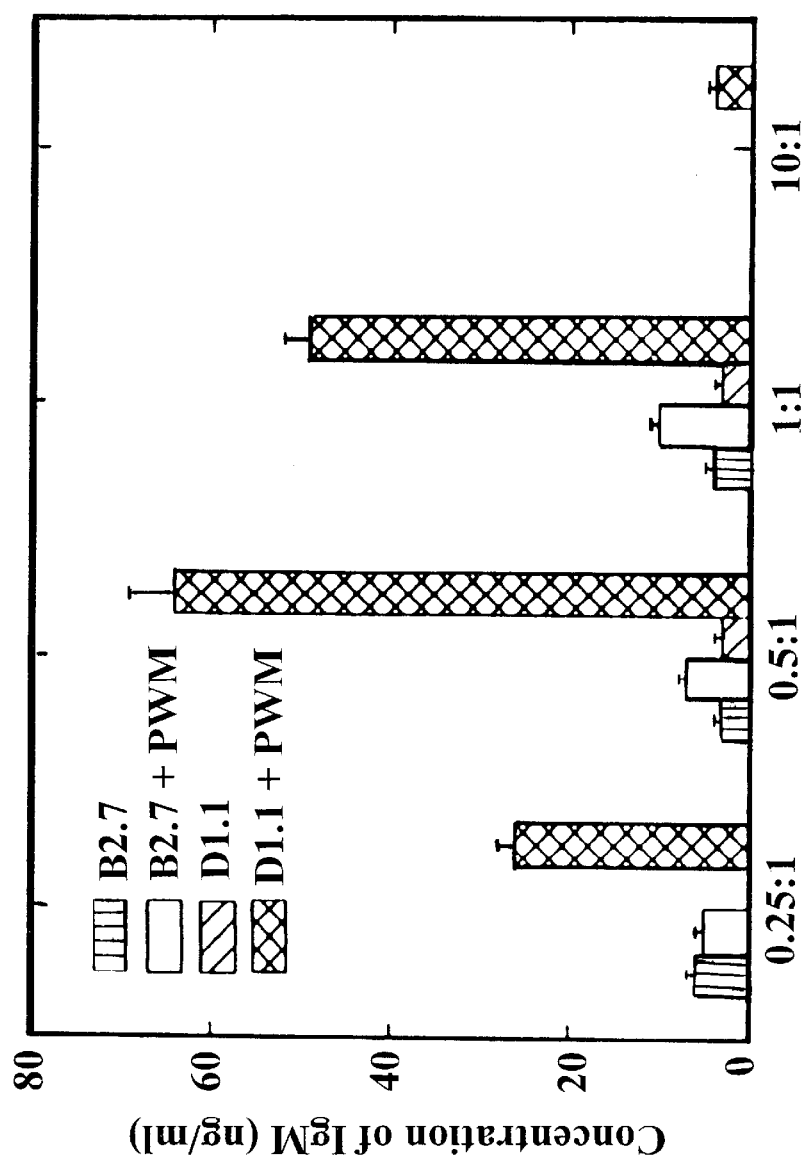

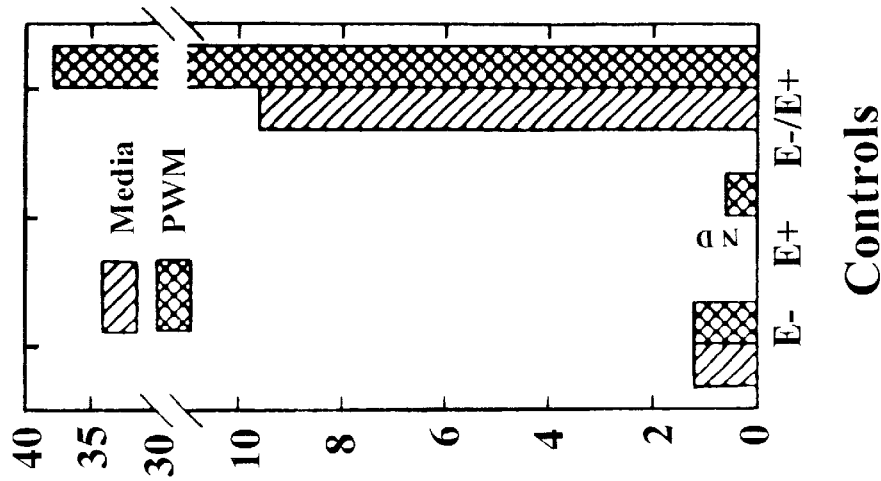
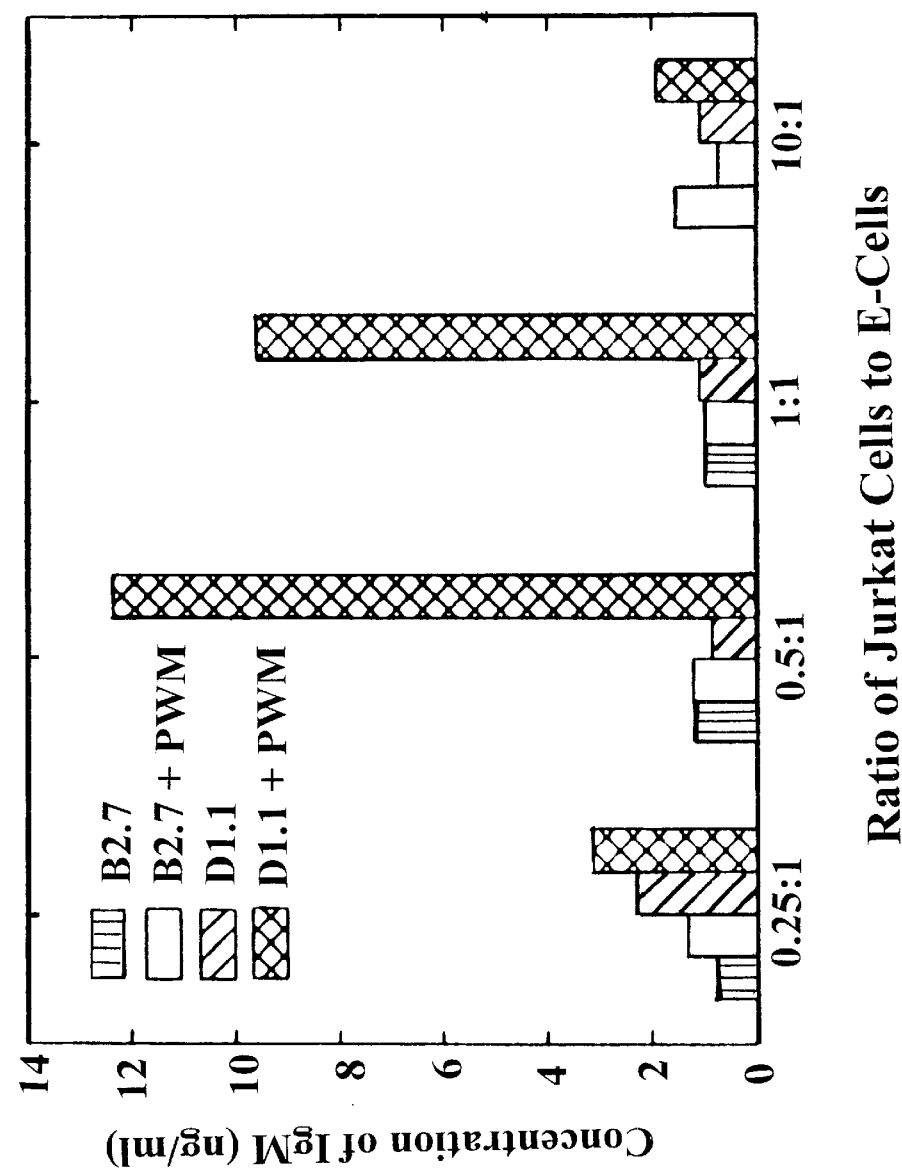
FIGURE 5B

B cells cultured with:

IgG mean channel fluorescence

40

Jurkat B2.7

34

Jurkat D1.1

44 rIL2

100 rIL4

41 rIL4 + anti-IL4 anti-IgM Fluorescence

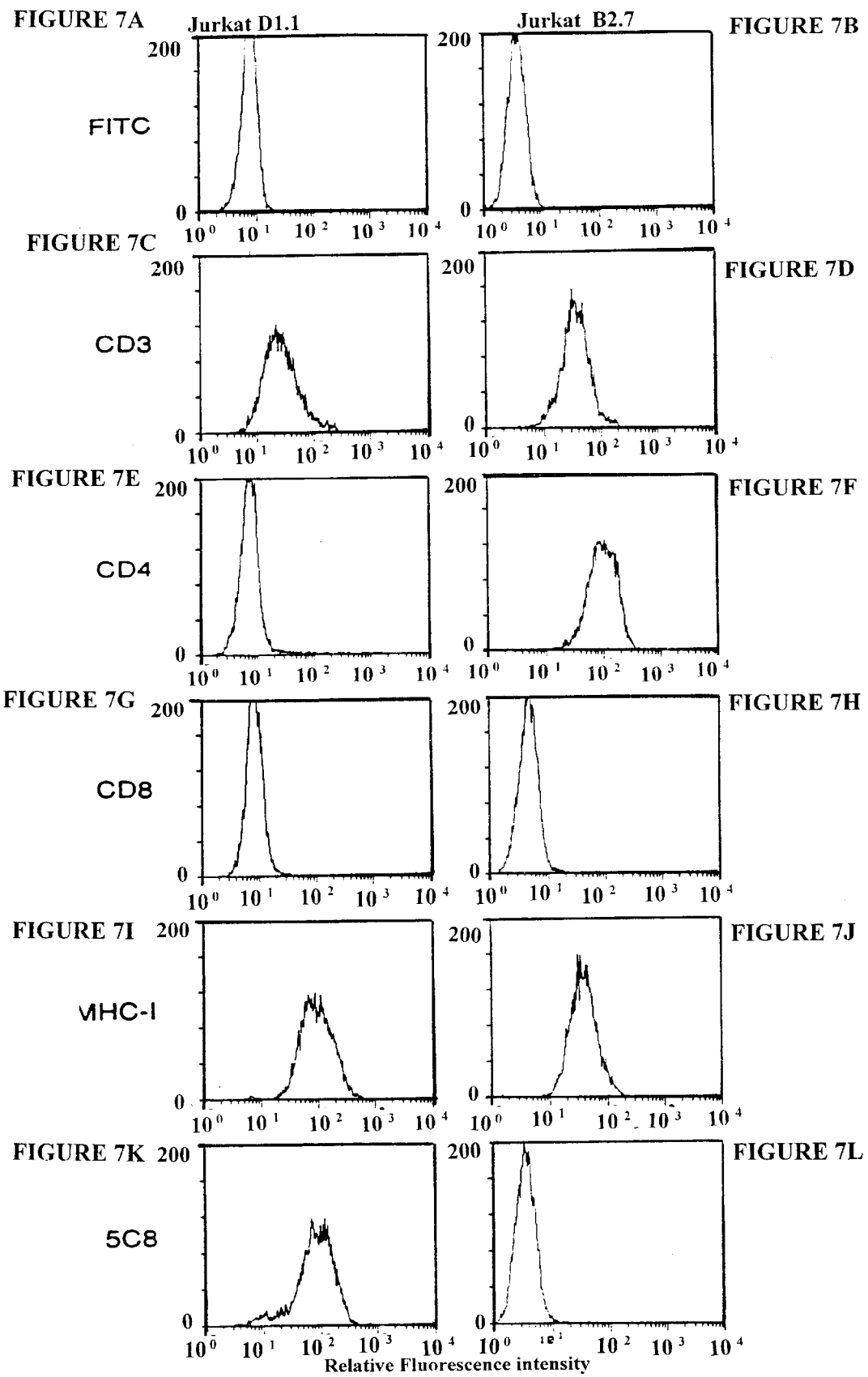

B cells cultured with:

B Cells Alone 1%

B2.7 Cells 1%

D1.1 Cells 50%

D1.1 Cells plus 5C8 1%

D1.1 Cells plus W6/32 50% anti-CD23 Fluorescence anti-IgM-Fluorescence

Jurkat D1.1

Jurkat B2.7

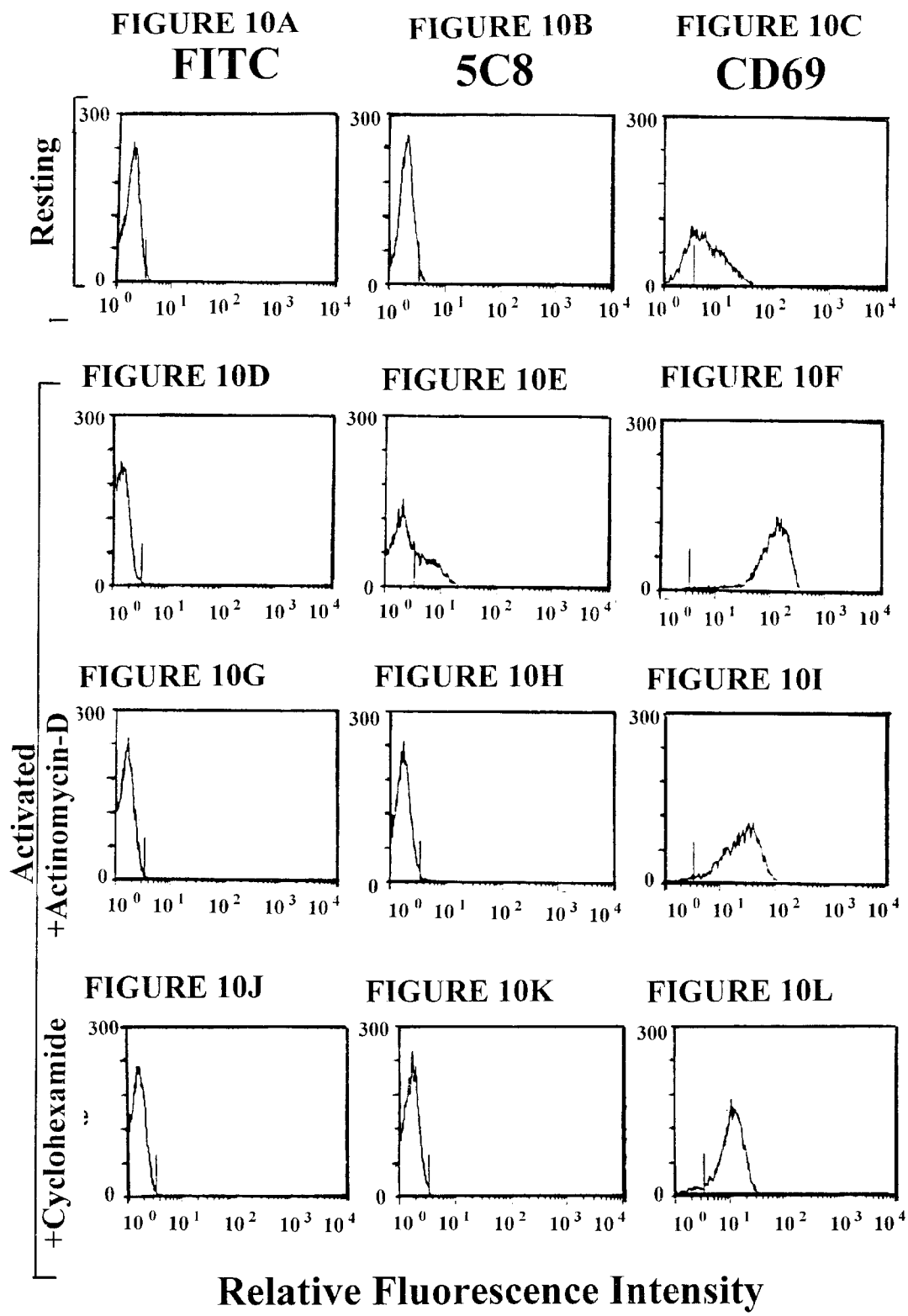

CD4⁺

CD8⁺

Mean Fluorescence

FIGURE 18
Models of Molecular T-B Interactions
Model #1.
T-BAM-CD40: receptor-ligand relationship
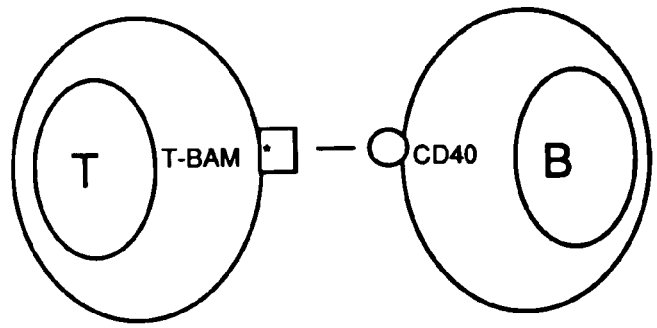
Model #2.
Interactions between T-BAM and CD40 with distinct ligands are both necessary for B cell activation
CD40 is a receptor for a distinct T cell ligand
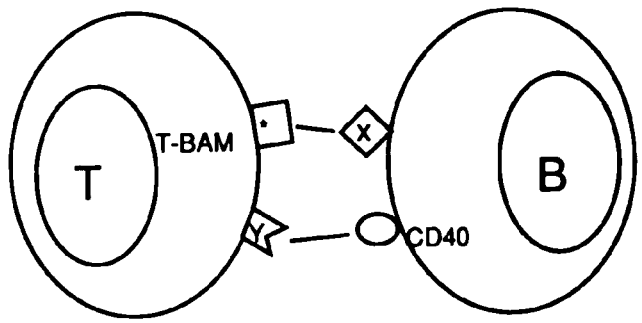
CD40 is a receptor for a soluble growth factor derived from
a.) T cells or
b.) B cells
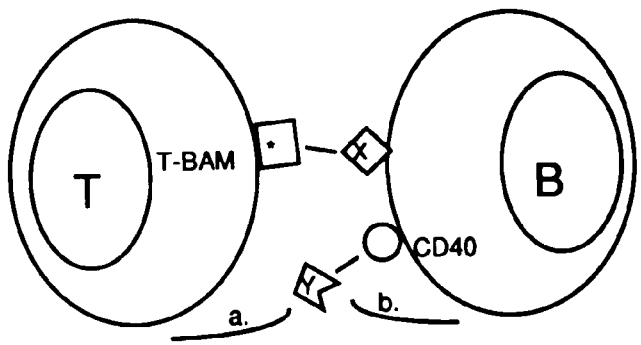

*Rheumatoid Arthritis a CD3 DAB Low Power*

*Rheumatoid Arthritis α CD3 DAB High Power*

*Rheumatoid Arthritis anti-CD4 (blue) anti-TBAM (brown)*

*Rheumatoid Arthritis anti-CD8 (blue) anti-TBAM (brown)*

*Psoriasis - low power*

*Psoriasis - high power* non-Hodgkins lymphoma non-Hodgkins lymphoma

```
                            SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:1:

ATHGARACNT AYAAYCA                                                     17

(2) INFORMATION FOR SEQ ID NO:2:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

ATGATHGARA CNTAYAAYCA                                                  20

(2) INFORMATION FOR SEQ ID NO:3:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

TGRTTRTANG TYTCDATCAT                                                  20
```

(2) INFORMATION FOR SEQ ID NO:4:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

```
GCATGATAGA AACATACAGC CAAC                                   24
```

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:5:

```
AACTGGACTT CCAGCGAGCA T                                      21
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

```
GGATCCTCAT CACCTCTTTG C                                      21
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:7:

```
ACAACGTGTG CTGCAATTTG AGG                                    23
```

(2) INFORMATION FOR SEQ ID NO:8:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:8:

TGACACCAGA CCAACTGGTA ATGG                                            24

(2) INFORMATION FOR SEQ ID NO:9:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:9:

Met Ile Glu Thr Tyr Asn Gln Gln Ser Pro Pro Xaa Ala Ala Ser
1               5                   10                  15

(2) INFORMATION FOR SEQ ID NO:10:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

Met Ile Glu Thr Tyr Ser Gln Pro Ser Pro Arg Ser Val Ala Thr
1               5                   10                  15

(2) INFORMATION FOR SEQ ID NO:11:

(i) SEQUENCE CHARACTERISTICS:
            (A) LENGTH: 10 amino acids
            (B) TYPE: amino acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:11:

Xaa Ile Glu Xaa Tyr Asn Gln Xaa Ser Pro
1               5                   10

(2) INFORMATION FOR SEQ ID NO:12:

```
        (i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

CTTTCAGTCA GC                                                             12

(2) INFORMATION FOR SEQ ID NO:13:

(i) SEQUENCE CHARACTERISTICS:
            (A) LENGTH: 325 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

TGGACTTCCA GCGAGCATGA AGATTTTTAT GTATTTACTT ACTGTTTTCC TTATCACCCA          60

AATGATTGGA TCTGTGCTTT TTGCTGTGTA TCTTCATAGA AGATTGGATA AGGTCGAAGA        120

GGAAGTAAAC CTTCATGAAG ATTTTGTATT CATAAAAAAG CTAAAGAGAT GCAACAAAGG        180

AGAAGGATCT TTATCCTTGC TGAACTGTGA GGAGATGAGA AGGCAATTTG AAGACCTTGT        240

CAAGGATATA ACGTTAAACA AGAAGAGAA AAAAGAAAAC AGCTTTGAAA TGCAAAGAGG         300

TGATGAGGAT CCTCAAATTG CAGCA                                              325

(2) INFORMATION FOR SEQ ID NO:14:

(i) SEQUENCE CHARACTERISTICS:
            (A) LENGTH: 342 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

TGGACTTCCA ACCGANCTTG GAAAATTTTT ATTGTATTTA CNTTCCTTGT TTTTCTTATC         60

CACCCCAAGA TGATTGGGTC AAGCACTTTT TNCTGTGTAT CTTCATAAGA AGGGTTGGAC        120

AAGATAGAAG ATGAAAGGAA TCTTCATTGA AGATTTGTA TTCATGAAAA CGATACAGAG         180

ATGCAACACA GGAGAAAGAT CCCTTATCCT TACTGAACTG TGAGGAGATT AAAAGCCAGT        240

TTGAAGGCTT TGTGAAGGAT ATAATGTTAA ACAAAGAGGA GACGAAGAAA GAAAACAGCT        300

TTGAAATNCA AAGAGGTGAT GAGGATCCAT CGAATTCCTG CA                           342

(2) INFORMATION FOR SEQ ID NO:15:

(i) SEQUENCE CHARACTERISTICS:
            (A) LENGTH: 53 base pairs
```

-continued

```
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

TGCAACACAG GAGAAAGATC CTTATCCTTA CTGCAACTGT GAGGAGATTA AAA            53

(2) INFORMATION FOR SEQ ID NO:16:

(i) SEQUENCE CHARACTERISTICS:
         (A) LENGTH: 53 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

TGCAACACAG GAGAAAGATC CCTTATCCTT ACTGAACTGT GAGGAGATTA AAA            53
```

METHODS OF INHIBITING AN AUTOIMMUNE RESPONSE IN A HUMAN SUFFERING FROM AN AUTOIMMUNE DISEASE BY ADMINISTERING AN ANTIBODY THAT BINDS TO A PROTEIN TO WHICH MONOCLONAL ANTIBODY 5C8 BINDS

This application is the United States national stage application of International Application No. PCT/US92/09955, international Filing date Nov. 16, 1992, which is a continuation-in-part of U.S. Ser. No. 07/792,728, filed Nov. 15, 1991, now U.S. Pat. No. 5,474,771, issued Dec. 12, 1995, the contents of each of which are hereby incorporated by reference in their entireties.

The invention described herein was made in the course of work under grant Nos. PO1-AI-26886, RO-1-AI-14969, RO-1-CA-55713 and Immunology Training Grant AI-07132 from the National Institutes of Health. The United States government therefore has certain rights in this invention.

BACKGROUND OF THE INVENTION

Throughout this application, various publications are referenced by the last name of the authors, followed by the year of publication within parenthesis. Full citations for these publications may be found at the end of the specification, immediately preceding the claims. The disclosures of these publications are hereby incorporated by reference into this application in order to more full describe the state of the art as known skilled therein as of the date of the invention described and claimed herein.

In a contact-dependent process termed "T cell helper function," $CD4^{30}$ T lymphocytes direct the activation and differentiation of B lymphocytes and thereby regulate the humoral immune response by modulating the specificity, secretion and isotype-encoded functions of antibody molecules (Mitchell, et al., 1968; Michison, 1971; White, et al., 1978; Reinherz, et al. 1979; Janeway, et al. 1988; O'Brien, et al., 1988; Rahemtulla, et al., 1991; and Grusby, et al., 1991). The T cell surface molecules that mediate the contact-dependent elements of T cell helper function are not yet fully known to one (Noelle, et al., 1991).

The process by which T cells help B cells to differentiate has been divided into two distinct phases: the inductive and effector phases (Vitetta, et al., 1989; Noelle, et al., 1990). In the inductive phase, resting T cells contact antigen-primed B cells and this association allows clonotypic T cell receptor (TCR)-CD4 complexes to interact with Ia/Ag complexes on B cells (Janeway, et al., 1988; Katz, et al., 1973; Zinkernagel, 1976; Sprent, 1978a; Sprent, 1978b; Jones, et al., 1981; Julius, et al., 1982; Chestnut, et al., 1981; Rogozinski, et al., 1984). TCR/CD4 recognition of Ia/Ag results in the formation of stable T-B cognate pairs and bidirectional T and B cell activation (Sanders, et al., 1986; Snow, et al., 1983; Krusemeier, et al., 1988; Noelle, et al., 1989; Bartlett, et al., 1989; Kupfer, et al., 1987). In the effector phase, activated T cells drive B cell differentiation by secreting lymphokines (Noelle, et al., 1983; Thompson, et al., 1985) and by contact-dependent stimuli (Noelle, et al., 1989; Clement, et al., 1984; Crow, et al., 1986; Brian, 1988; Hirohata, et al., 1988; Jover, et al., 1989; Whalen, et al., 1988; Pollok, et al., 1991; Bartlett, et al., 1990), both of which are required for T cells to drive small, resting B cells go terminally differentiate into Ig secreting cells (Clement, et al., 1984; Martinez, et al., 1981; Andersson, et al., 1980).

Although the inductive phase of T cell help is Ag-dependent and MHC-restricted (Janeway, et al., 1988; Katz, et al., 1973; Zinkernagle, 1976; Sprent, 1978a; Sprent, 1978b; Jones, et al., 1981; Julius, et al., 1982; Chestnut, et al., 1981; Andersson, et al., 1980), the effector phase of T cell helper function can be Ag-independent and MHC-nonrestricted (Clement, et al., 1984; Hirohata, et al., 1988; Whalen, et al., 1988; Andersson, et al., 1980; DeFranco, et al., 1984; Julius, et al., 1988a; Julius, et al., 1988b; Riedel, et al., 1988; Owens, 1998; Cambier, et al., 1988; Tohma, et al., 1999; Lohoff, et al., 1977). An additional contrasting feature is that the inductive phase of T cell help often requires CD4 molecules and is inhibited by anti-CD4 mAb (Rogoznski, et al., 1984), whereas helper effector function does not require CD4 molecules (Friedman,e t al., 1986) and is not inhibited by anti-CD4 mAbs (Brian, 1988; Hirohata, et al., 1988; Whalen, et al., 1988; Tohma, et al., 1991). The nonspecific helper effector function is believed to be focused on specific B cell targets by the localized nature of the T-B cell interactions with antigen specific, cognate pairs (Bartlett, et al., 1989; Kupfer, et al., 1987; Poo, et al., 1988).

Although terminal B cell differentiation requires both contact- and lymphokine-mediated stimuli from T cells, intermediate stages of B cell differentiation can be induced by activated T cell surfaces in the absence of secreted factors (Crow, et al., 1986; Brian, 1988; Sekita, et al., 1988; Hodgkin, et al., 1990; Noelle, et al., 1991; Kubota, et al., 1991). These intermediate effects on B cells include induction of surface CD23 expression (Crow, et al., Jover, et al., 1989; Crow, et al., 1989), enzymes associated with cell cycle progression (Pollok, et al., 1991) and responsiveness to lymphokines (Noelle, et al., 1989; Pollok, et al., 1991; Tohma, et al., 1991; Hodgkin, et al., 1990; Noelle, et al., 1991; Kubota, et al., 1991). Although the activation-induced T cell surface molecules that direct B cell activation have not been previously identified, functional studies have characterized some features of their induction and biochemistry. First, T cells acquire the ability to stimulate B cells 4–8 h following activation (Bartlett, et al. 1990; Tohma, et al., 1991). Second, the B cell stimulatory activity associated with the surfaces of activated T cells is preserved on paraformaldehyde fixed cells (Noelle, et al., 1989; Crow, et al., 1986; Pollok, et al., 1991; Tohma, et al., 1991; Kubota, et al., 1991) and on purified membrane fragments (Hodgkin, et al., 1990; Martinez, et al., 1981). Third, the B cell stimulatory activity is sensitive to protease treatment (Noelle, et al., 1989; Sekita, et al., 1988; Hodgkin, et al., 1990). Fourth, the process of acquiring these surface active structures following T cell activation is inhibited by cyclohexamide (Tohma, et al., 1991; Hodgkin, et al., 1990). Although these studies strongly suggest the existence of activation-induced T cell surface proteins that deliver contact dependent stimuli to B cells, the molecular identities of such structures remain unknown.

The isolation of a $CD4^{-1}$ Jurkat subclone (D1.1) that possessed the unique functional potential to activate B cells to express surface CD23 molecules and to support the terminal differentiation of B cells in the presence of lectins was previously reported (Yellin, et al., 1991). Jurkat D1.1 activated B cells from a large number of unrelated donors suggesting that the D1.1 effect was Ag independent and MHC unrestricted. The mechanism of Jurkat D1.1 mediated B cell activation was found to depend on cell-cell contacts or close proximity because paraformaldehyde fixed D1.1 cells, but not secreted factors, possessed the ability to induce B cell CD23. In addition, the effect of D1.1 on B cells was not inhibited by anti-IL-4 antibodies. Further, the effect of D1.1 on B cells was distinct from that of IL-4 because rIL-4 but not D1.1 induced upregulation of B cell surface IgM (sIgM) (Yellin, et al., 1991; Shields, et al., 1989). Taken together, these data suggested that Jurkat D1.1 and activated CD4+ T cells shared surface structures that provide contact dependent elements of T cell help to B cells (Yellin, et al., 1991).

In this application, a murine IgG2a mAb (5c8) was generated that inhibits D1.1 mediated B cell activation and immunoprecipitates a novel 30 kilodalton (kD) non-disulfide linked protein from the surface of D1.1. On normal T cells, the 5c8 antigen is transiently expressed on activated CD4+ T cells in a manner than requires mRNA and protein synthesis. In functional studies, mAb 5c8 inhibits the ability of T cells to mediate B cell activation and terminal differentiation. Taken together, these data demonstrate that the 5c8 Ag is an important component of the activation-induced T cell surface structures that mediate contact dependent stimuli for B cell differentiation.

SUMMARY OF THE INVENTION

This invention provides a monoclonal antibody capable of binding to a protein which is specifically recognized by monoclonal antibody 5c8 produced by the hybridoma having ATCC Accession No. HB 10916. This invention also provides the monoclonal antibody 5c8 produced by the hybridoma having ATCC Accession No. 10916.

This invention provides a human CD4⁻T cell leukemia cell line designated D1.1 having ATCC Accession No. CRL 10915 capable of constitutively providing contact-dependent helper function to B cells. This invention also provides an isolated protein from the surface of activated T cells, wherein the protein is necessary for T cell activation of B cells. This invention further provides an isolated, soluble protein from the surface of activated T cells, wherein the protein is necessary for T cell activation of B cells.

This invention further provides an isolated nucleic acid molecule encoding a protein which is specifically recognized by monoclonal antibody 5c8 produced by the hybridoma having ATCC No. HB 10916.

BRIEF DESCRIPTION OF THE FIGURES

FIG. 1A. A fluorescence histogram (FACS) analysis of CD4+ Jurkat B2.7 is shown. This figure is a "control" which represents the background staining in the absence of added primary mAb.

FIG. 1B. A fluorescence histogram (FACS) analysis of CD4– Jurkat D1.1 is shown. This figure is a "control" which represents the background staining in the absence of added primary mAb.

FIG. 1C. Fluorescence histogram (FACS) analysis of CD4+ Jurkat B2.7 stained with mAb OKT3 (anti-CD3).

FIG. 1D. Fluorescence histogram (FACS) analysis of CD4– Jurkat D1.1 stained with mAb OKT3 (anti-CD3).

FIG. 1E. Fluorescence histogram (FACS) analysis of CD4+ Jurkat B2.7 stained with mAb OKT4 (anti-CD4).

FIG. 1F. Fluorescence histogram (FACS) analysis of CD4– Jurkat D1.1 stained with mAb OKT4 (anti-CD4).

FIG. 1G. Fluorescence histogram (FACS) analysis of CD4+ Jurkat B2.7 stained with mAb W6/32 (anti-MHC I).

FIG. 1H. Fluorescence histogram (FACS) analysis of CD4– Jurkat D1.1 stained with mAb W6/32 (anti-MHC I).

FIGS. 2A–F. Jurkat D1.1 induces CD23 expression on resting B lymphocytes. Shown are two-color FACS analyses of adherence depleted, high density B cells after 24 h of culture alone (media) or with CD4– Jurkat (D1.1) or CD4– Jurkat (B2.7) by using anti-IgM-FITC or anti-CD20 (Leu-16)-FITC on the x axis and anti-CD23-PE on the y-axis (Becton-Dickinson). The numbers shown in the upper right hand corner of each of the histograms in FIGS. 2A–F represents the percentage of all gated cells that express both molecules. In the experiment shown, single color FACS showed the population of small, high density B cells to be 2% CD3(OKT3)+, 84% IgM+, 84% CR2(HB-5)+, and 87% CD20(Leu-16G)+.

FIG. 2A. Two-color FACS analysis of adherence depleted, high density B cells after 24 h of culture alone (media) by using anti-IgM-FITC on the x axis and anti-CD23-PE on the y-axis.

FIG. 2B. Two-color FACS analysis of adherence depleted, high density B cells after 24 h of culture alone (media) by using anti-CD20 (Leu-16)-FITC on the x axis and anti-CD23-PE on the y-axis.

FIG. 2C. Two-color FACS analysis of adherence depleted, high density B cells after 24 h of culture with CD4+ Jurkat (B2.7) by using anti-IgM-FITC on the x axis and anti-CD23-PE on the y-axis. The population of B cells cultured with Jurkats B2.7 expressed CD23 on 16% of IgM+ cells.

FIG. 2D. Two-color FACS analysis of adherence depleted, high density B cells after 24 h of culture with CD4+ Jurkat (B2.7) by using anti-CD20 (Leu-16)-FITC on the x axis and anti-CD23-PE on the y-axis. The population of B cells cultured with Jurkat B2.7 expressed CD23 on 16% of CD20+ cells.

FIG. 2E. Two-color FACS analysis of adherence depleted, high density B cells after 24 h of culture with CD4– Jurkat (D1.1) by using anti-IgM-FITC on the x axis and anti-CD23-PE on the y-axis. The population of B cells cultured with Jurkat D1.1 expressed CD23 on.66% of IgM+ cells.

FIG. 2F. Two-color FACS analysis of adherence depleted, high density B cells after 24 h of culture with CD4– Jurkat (D1.1) by using anti-CD20 (Leu-16)-FITC on the x axis and anti-CD23-PE on the y-axis. The population of B cells cultured with Jurkat D1.1 expressed CD23 on 69% of CD20+cells.

FIGS. 3A–B. Dose response of D1.1-induced CD23 expression.

FIG. 3A. Shown are the percentage of IgM⁺ cells that express CD23 after 24 h culture with varying ratios of D1.1 or B2.7 cells or cell supernatants. Experimental conditions and two-color FACS analysis were as described for FIGS. 2A–2F except that the ratio of Jurkats added to 2×10⁵ B cells was varied as shown. The background level (B cells alone) of CD23 expression of IgM⁺ cells was 12%. The B cell population was 65% IgM⁺ in this experiment.

FIG. 3B. Supernatants were obtained 48 h after 1×10⁵ D1.1 or B2.7 cells were cultured in 1 ml of Iscove's modified Dulbecco medium/10% FCS and were passed through 0.2-μm filters before addition to the B cells.

FIG. 4A. Shown is [³H] thymidine uptake of B cells cultured with mitocycin-C-treated Jurkat cells in the presence of the indicated combinations of rIL-2 (25 U/ml), rIL-4(25 U/ml), or PHA (5 μg/ml). Error bars represent standard deviation of the means of triplicate cultures.

FIG. 4B. Controls for the experiment shown in FIG. 4A.

FIGS. 5A–C. Jurkat D1.1 induces B cell differentiation into Ig secreting cells. E– cells are E rosette-depleted, adherence-depleted, high density PERCOLL® population that is predominantly B cells. E+ cells are E rosette-positive, resting T cells treated with mitomycin-C. Measurement of Ig was performed by quantitative sandwich ELISA and error bars represent calculated standard deviation based on standard curves. E rosettes were performed with neuraminidase-treated sheep erythrocytes.

FIG. 5A. IgM in supernatants from the same experiments as in FIG. 5B. FIG. 5A-2 shows controls for the experiment shown in FIG. 5A-1.

FIG. 5B. Number of plaque-forming colonies per $10^6$ B cells induced by indicated ratios of Jurkat D1.1 or B2.7 to B cells in the presence of absence of PWM. FIG. 5B-2 shows controls for the experiment shown in FIG. 5B-1.

FIG. 5C. IgG in supernatants from the same experiments as in FIG. 53. FIG. 5C-2 shows controls for the experiment shown in FIG. 5C-1.

FIG. 6A. FACS analysis of B cells cultured with Jurkat B2.7.

FIG. 6B. FACS analysis of B cells cultured with Jurkat D1.1.

FIG. 6C. FACS analysis of B cells cultured with Jurkat rIL2. The concentration of rIL-4 is 50 U/ml.

FIG. 6D. FACS analysis of 3 cells cultured with rIL-4. The concentration of rIL-4 is 50 U/ml.

FIG. 6E. FACS analysis of B cells cultured with rIL-4+ anti-IL4. The concentration of anti-IL-4 shown is 1.25 µg/ml and the concentration of rIL-4 is 50 U/ml.

FIGS. 7A–L. Binding of mAb 5c8 to Jurkat D1.1 cells. Shown are fluorescence histogram (FACS) analyses of CD4– Jurkat D1.1 and CD4+ Jurkat B2.7 cells. The Y axis represents number of cells and the X axis represents relative fluorescence intensity. FITC represents the background staining of an isotype matched control mAb.

FIG. 7A. A fluorescence histogram (FACS) analysis of CD4– Jurkat D1.1 cells.

FIG. 7B. A fluorescence histogram (FACS) analysis of CD4+ Jurkat B2.7 cells. FITC represents the background staining of an isotype matched control mAb.

FIG. 7C. A fluorescence histogram (FACS) analysis of CD4– Jurkat D1.1 cells stained with mAb OKT3 (anti-CD3).

FIG. 7D. A fluorescence histogram (FACS) analysis of CD4+ Jurkat B2.7 cells stained with mAb OKT3(anti-CD3).

FIG. 7E. A fluorescence histogram (FACS) analysis of CD4– Jurkat D1.1 cells stained with mAb OKT4 (anti-CD4).

FIG. 7F. A fluorescence histogram (FACS) analysis of CD4+ Jurkat B2.7 cells stained with mAb OKT4 (anti-CD4).

FIG. 7G. A fluorescence histogram (FACS) analysis of CD4– Jurkat D1.1 cells stained with mAb OKT8.(anti-CD8).

FIG. 7H. A fluorescence histogram (FACS) analysis of CD4+ Jurkat B2.7 cells stained with mAb OKT8 (anti-CD8).

FIG. 7I. A fluorescence histogram (FACS) analysis of CD4– Jurkat D1.1 cells stained with mAb W6/32(anti-MHC I).

FIG. 7J. A fluorescence histogram (FACS) analysis of CD4+ Jurkat B2.7 cells stained with mAb W6/32(anti-MHC I).

FIG. 7K. A fluorescence histogram (FACS) analysis of CD4– Jurkat D1.1 cells stained with mAb 5c8.

FIG. 7L. A fluorescence histogram (FACS) analysis of CD4+ Jurkat B2.7 cells stained with mAb 5c8.

FIG. 8A. Two color FACS analyses of adherence depleted, high density B cells after 24 h of culture alone.

FIG. 8B. Two color FACS analyses of adherence depleted, high density B cells after 24 h of culture with the B2.7 Jurkat clones.

FIG. 8C. Two color FACS analyses of adherence depleted, high density B cells after 24 h of culture with the D1.1 Jurkat clones.

FIG. 8D. Two color FACS analyses of adherence depleted, high density B cells after 24 h of culture with the D1.1 Jurkat clones in the presence of mAb 5c8. The mAb 5c8 was present at a 1:200 dilution of hybridoma supernatant.

FIG. 8E. Two color FACS analyses of adherence depleted, high density B cells after 24 h of culture with the D1.1 Jurkat clones in the presence of W6/32. The mAb W6/32 was present at 1 µg/ml. The murine IgG2a mAb W6/32 recognizes a monomorphic determinant on Class I MHC molecules.

FIG. 9A. Shown are autoradiogram of immunoprecipitates with mAb 5c8 or control mAbs from cells lysates of surface iodinated Jurkat D1.1 cells that were separated on 12.5% polyacrylamide in the presence (reduced, R) or absence (non-reduced, NR) of 2-ME (2-mercaptoethanol). mAbs shown are anti-CD28 (KOLT-4) and anti-MHC Class I (W6/32). MW markers represent the migration of pre-labeled standard. NMS: normal mouse serum.

FIG. 9B. Same as FIG. 9A except that Jukat B2.7 cells were used in place of Jurkat D1.1 cells.

FIGS. 10A–L. Effects of T cell activation and metabolic inhibitors on the expression of 5c8 antigen on activated T cells.

FIG. 10A. FACS histogram of resting T cells using FITC. FITC represents a control for background staining.

FIG. 10B. FACS histogram of resting T cells using mAb 5c8.

FIG. 10C. FACS histogram of resting T cells using anti-CD69.

FIG. 10D. FACS histogram of activated T cells using FITC. T cells were activated by PMA (10 ng/ml) and PHA (10 µg/ml) for 5 h. FITC represents a control for background staining.

FIG. 10E. FACS histogram of activated T cells using mAb 5c8. T cells were activated by PMA (10 ng/ml) and PHA (10 µg/ml) for 5 h.

FIG. 10F. FACS histogram of activated T cells using anti-CD69. T cells were activated by PMA (10 ng/ml) and PHA (10 µg/ml) for 5 h.

FIG. 10G. FACS histogram of activated T cells using FITC. T cells were activated by PMA (10 ng/ml) and PHA (10 µg/ml) for 5 h performed in the presence of actinomycin D (10 µM). FITC represents a control for background staining.

FIG. 10H. FACS histogram of activated T cells using mAb 5c8. T cells were activated by PMA (10 ng/ml) and PHA (10 µg/ml) for 5 h performed in the presence of actinomycin D (10 µM).

FIG. 10I. FACS histogram of activated T cells using anti-CD69. T cells were activated by PMA (10 ng/ml) and PHA (10 µg/ml) for 5 h performed in the presence of actinomycin D (10 µM).

FIG. 10J. FACS histogram of activated T cells using FITC. T cells were activated by PMA (10 ng/ml) and PHA (10 µg/ml) for 5 h performed in the presence of cycloheximide (100 µM). FITC represents a control or background staining.

FIG. 10K. FACS histogram of activated T cells using mAb 5c8. T cells were activated by PMA (10 ng/ml) and PHA (10 µg/ml) for 5 h performed in the presence of or cycloheximide (100 µM).

FIG. 10L. FACS histogram of activated T cells using anti-CD69. T cells were activated by PMA (10 ng/ml) and PHA (10 µg/ml) for 5 h performed in the presence of cycloheximide (100 µM).

FIG. 11A. Fluorescence histogram of $CD4^+$ cells which were not activated with PHA (10 µg/ml) and PMA (10 ng/ml). Solid line: 5c8 binding; dashed line: IgG2a control; and dotted line: anti-CD69.

FIG. 11B. Fluorescence histogram of CD4+ cells 6 hours after freshly purified T cell subsets were activated with PHA (10 µg/ml) and PMA (10 ng/ml).

FIG. 11C. Fluorescence histogram of $CD4^+$ cells 24 hours after freshly purified T cell subsets were activated with PHA (10 µg/ml) and PMA (10 ng/ml).

FIG. 11D. Fluorescence histogram of $CD8^+$ cells which were not activated with PHA (10 µg/ml) and PMA (10 ng/ml).

FIG. 11E. Fluorescence histogram of $CD8^+$ cells 6 hours after freshly purified T cell subsets were activated with PHA (10 µg/ml) and PMA (10 ng/ml).

FIG. 11F. Fluorescence histogram of $CD8^+$ cells 24 hours after freshly purified T cell subsets were activated with PHA (10 µg/ml) and PMA (10 ng/ml).

(FIG. 14A) rIL4 and rIL-2 were present at 10 units/ml, anti-IL-4 and anti-GM-CSF ("CSF") were present at 10 µg/ml. (FIG. 14B) the indicated mAbs were added at the initiation of culture at saturating concentrations.

FIG. 17E x63) using mAb 5c8 and a modified ABC technique (see Materials and Methods). T-BAM positivity is manifested as membrane staining.

FIG. 18. Model of T-B Molecular Interactions

(FIGS. 19A–B) anti-CD3 diaminobenzidine (DAB) staining (FIG. 19A low power, FIG. 19B high power). (FIG. 19C) double staining anti-CD4 (blue fuscin, APAP staining) and anti-T-BAM (mAb 5c8, brown, DAB). (FIG. 19D) anti-CD8 (blue fuscin, APAP staining and anti-T-BAM (mAB 5c8, brown, DAB). Together these specimens show that T-BAM is expressed on CD4+ T cells involved in the synovial inflammation of rheumatoid arthritis.

DETAILED DESCRIPTION OF THE INVENTION

Figure 1A:
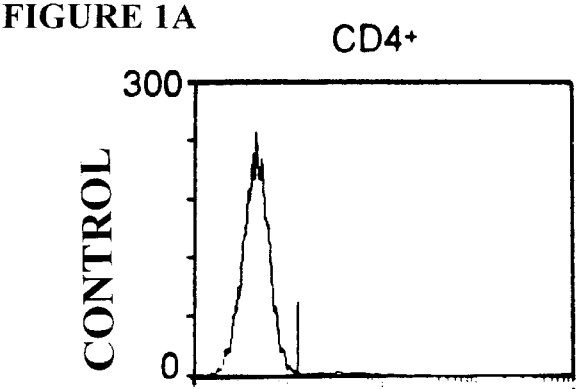
FIGS. 1A–H. Cell surface phenotype of CD4– Jurkat D1.1. Shown are fluorescence histogram (FACS) analyses of CD4– Jurkat D1.1 and CD4+ Jurkat B2.7. The Y axis represents number of cells and the X axis represents relative fluorescence intensity.
Figure 1B:
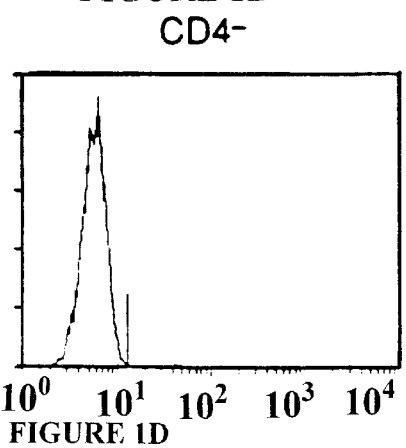
Figure 1C:
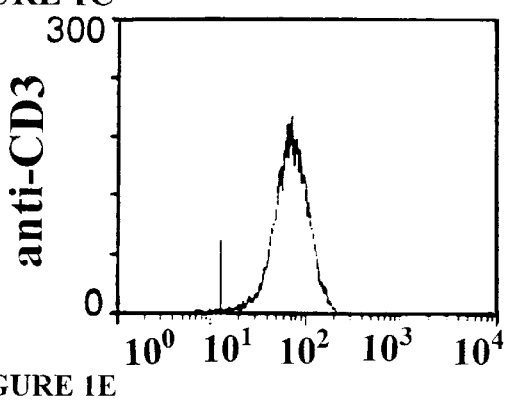
Figure 1D:
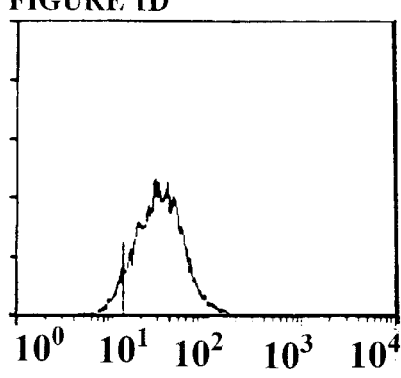
Figure 1E:
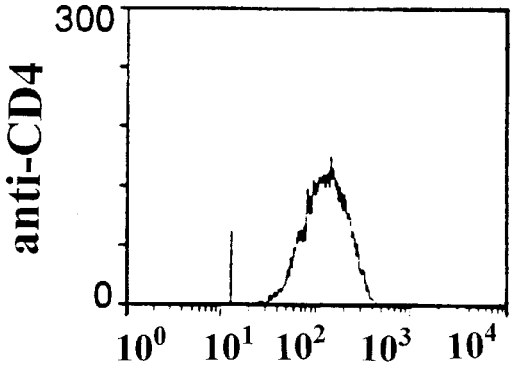
Figure 1F:
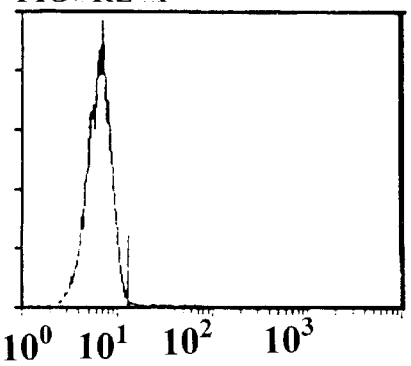
Figure 1G:
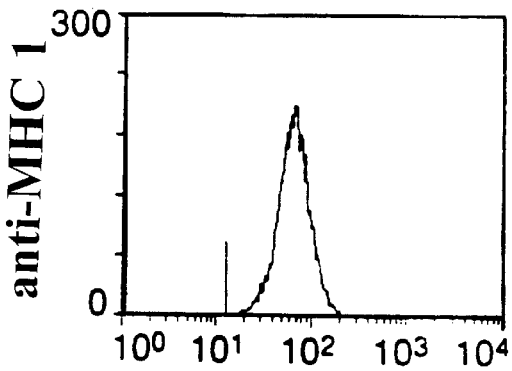
Figure 1H:
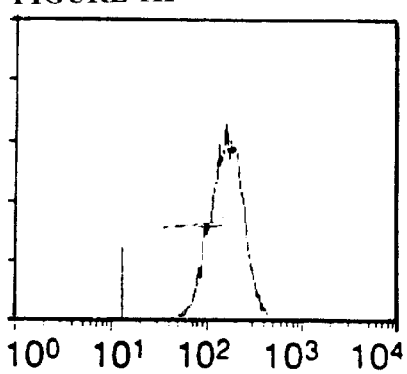

This invention provides a monoclonal antibody capable of binding to a protein which is specifically recognized by monoclonal antibody 5c8 produced by the hybridoma having ATCC Accession No. HB 10916.

This invention provides a monoclonal antibody which specifically recognizes and forms a complex with a protein located on the surface of activated T cells, thereby inhibiting T cell activation of B cells. Activated T cells are found normally only in the germinal centers of an animal's lymph nodes. However, activated T cells are found in the peripheral blood of animals suffering from T cell tumors, e.g., T cell leukemias and lymphomas or infiltrating tissues of diseases such as rheumatoid arthritis and psoriasis.

The monoclonal antibody described and claimed herein binds to T cells which are interacting with B cells in the germinal centers of lymph nodes and not to other T cells in healthy individuals. Monoclonal antibodies known to those skilled in the art to specifically recognize and bind to proteins on the surface of T cells and thereby inhibit the activation of B cells, e.g., anti-CD28 monoclonal antibody and anti-LFA-1 monoclonal antibody, do not distinguish activated T cells.

For the purposes of this invention, "activated T cells" are T cells capable of providing T cell helper function to resting B cells. For the purposes of this invention, "germinal centers of lymph nodes" are the areas in lymph nodes where T cells provide T cell helper function to B cells.

For the purposes of this invention a "monoclonal antibody" is an antibody produced by a hybridoma cell. Methods of making monoclonal antibody-synthesizing hybridoma cells are well known to those skilled in the art, e.g., by the fusion of an antibody producing B lymphocyte with an immortalized B-lymphocyte cell line.

In one embodiment of this invention, the B cells are resting B cells. In another embodiment of this invention, the B cells are primed B cells. For the purposes of this invention, "resting" B cells are unactivated B cells, i.e., undifferentiated B cells which do not synthesize antibody molecules. For the purposes of this invention, "primed" B cells are B cells which have been contacted with antigen and have thereby been partially activated, but which do not yet synthesize antibody molecules.

In one embodiment of this invention, the monoclonal antibody is a murine monoclonal antibody. In another embodiment of this invention, the monoclonal antibody is a chimaeric monoclonal antibody. In still another embodiment of this invention, the monoclonal antibody is a humanized monoclonal antibody. However, in the preferred embodiment of this invention, the monoclonal antibody is a human monoclonal antibody.

For the purposes of this invention, a "chimaeric" monoclonal antibody is a murine monoclonal antibody comprising constant region fragments ($F_c$) from a different animal. In a preferred embodiment of this invention, the chimaeric monoclonal antibody comprises human $F_c$ and murine $F_{ab}$. For the purposes of this invention, a "humanized" monoclonal antibody is a murine monoclonal antibody in which human protein sequences have been substituted for all the murine protein sequences except for the murine complementarity determining regions (CDR) of both the light and heavy chains.

In one embodiment of this invention, the monoclonal antibody is directed to the epitope which is specifically recognized by the monoclonal antibody 5c8 produced by the hybridoma having ATCC Accession No. HB10916 is directed. In still another embodiment of this invention, the monoclonal antibody is the monoclonal antibody 5c8.

This invention further provides a hybridoma cell producing the monoclonal antibody capable of binding to a protein which as specifically recognized by monoclonal antibody 5c8 produced by the hybridoma having ATCC Accession No. HB 10916. For the purposes of this invention, a "hybridoma cell" is a cell formed by the fusion of an immortalized cell and an antibody-producing cell, thereby forming a cell which makes a monoclonal antibody. In an embodiment, the hybridoma cell was accorded with ATCC Accession No. HB 10916 which was deposited on Nov. 14, 1991 with the American Type Culture Collection (ATCC), 10801 University Blvd., Manassas, Va. 20110-2209, U.S.A. under the provision of the Budapest Treaty for the International Recognition of the Deposit of Microorganism for the Purposes of Patent Procedure.

In one of this invention, the monoclonal antibody is labelled with a detectable marker, for example, a radioactive isotope, enzyme, dye or biotin. In another embodiment of this invention, the monoclonal antibody is conjugated to a therapeutic agent, for example, a radioisotope, toxin, toxoid or chemotherapeutic agent. In still another embodiment of this invention, the monoclonal antibody is conjugated to an imaging agent for example, a radioisotope.

This invention provides a pharmaceutical composition comprising the monoclonal antibody and a pharmaceutically acceptable carrier. For the purposes of this invention "pharmaceutically acceptable carriers" means any of the standard pharmaceutical carriers. Examples of suitable carriers are well known in the art and may include, but not limited to, any of the standard pharmaceutical carriers such as a phosphate buffered saline solutions, phosphate buffered saline containing POLYSORB® 80, water, emulsions such as oil/water emulsion, and various type of wetting agents. Other carriers may also include sterile solutions, tablets, coated tablets, and capsules.

Typically such carriers contain excipients such as starch, milk, sugar, certain types of clay, gelatin, stearic acid or salts thereof, magnesium or calcium sterate, talc, vegetable fats or oils, gums, glycols, or other known excipients. Such carriers may also include flavor and color additives or other ingredients. Compositions comprising such carriers are formulated by well known conventional methods.

Such carriers are well known in the art and may include, but not intended to be limited to, any of the standard pharmaceutical carriers such as a phosphate buffered saline solutions, water, emulsions such as oil/water emulsion, and various types of wetting agents. Other carriers may also include sterile solutions, tablets, coated tablets, and capsules.

The monoclonal antibodies described and claimed herein are useful for isolating the proteins to which the monoclonal antibodies bind. The monoclonal antibodies are also valuable in new and useful methods for: inhibiting the immune response in an animal; modulating the immune response in diseases characterized by immune dysfunctions such as autoimmune diseases or infectious diseases with autoimmune manifestation such as lyme disease, syphilis, tuberculosis and HIV infections; imaging tumors or neoplasia in an animal; detecting the presence of tumor or neoplasm in an animal; determining whether an animal harbors tumor cells; inhibiting the proliferation of T cell tumor cells in an animal suffering from a T cell cancer; and inhibiting viral infection of the T cells of an animal.

This invention provides an isolated nucleic acid molecule encoding the light chain protein of the monoclonal antibody. In one embodiment of this invention, the nucleic acid molecule is a DNA molecule. Preferably, the DNA molecule is a cDNA molecule.

Throughout this application, references to specific nucleotides are to nucleotides present on the coding strand of the nucleic acid. The following standard abbreviations are used throughout the specification to indicate specific nucleotides:

| C = cytosine | A = adenosine |
|---|---|
| T = thymidine | G = guanosine |

DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs whereon one or more amino acid residues is added to a terminal or medial portion of the polypeptides) and which share some or all properties of naturally-occurring forms. These include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acid sequences described and claimed herein are useful for generating new viral and circular plasmid vectors described below. The nucleic acid molecules are also valuable in a new and useful method of gene therapy, i.e., by stably transforming cells isolated from an animal with the nucleic acid molecules and then readministering the stably transformed cells to the animal. Methods of isolating cells include any of the standard methods of withdrawing cells from an animal. Suitable isolated cells include, but are not limited to, bone marrow cells. Methods of readministering cells include any of the standard methods of readministering cells to an animal.

This invention provides a gene transfer vector, for example a plasmid or a viral vector, comprising a nucleic acid molecule encoding the light chain protein of the monoclonal antibody operably linked to a promoter of RNA transcription. This invention also provides a gene transfer vector, for example a plasmid or a viral vector, comprising a nucleic acid molecule encoding the heavy chain protein of the monoclonal antibody operably linked to a promoter of RNA transcription.

The gene transfer vectors described and claimed herein are valuable as products useful for generating stably transformed eukaryotic host cells, and thereby in new and useful methods of growing such host cells under conditions suitable for the production of a protein.

This invention provides a host vector system comprising the gene transfer vectors described and claimed herein in a suitable host cell. In one embodiment of this invention, the suitable host cell is a stably transformed eukaryotic cell, for example a stably transformed yeast or a mammalian cell. In the preferred embodiment of this invention, the stably transformed eukaryotic cell is a stably transformed mammalian cell.

The host vector system described and claimed herein is valuable in a new and useful method for the synthesis of a monoclonal antibody, comprising growing the host vector system under conditions suitable for the production of the monoclonal antibody.

This invention provides a CD4$^-$ human T cell leukemia cell line designated D1.1 having ATCC Accession No. CRL 10915 capable of constitutively providing contact-dependent helping function to B cells. The D1.1 cell was deposited on Nov. 14, 1991 with the American Type Culture Collection (ATCC), 10801 University Blvd., Manassas, Va. 20110-2209, U.S.A. under the provision of the Budapest Treaty for the International Recognition of the Deposit of Microorganism for the Purposes of Patent Procedure. In one embodiment of this invention, the B cells are resting B cells. In another embodiment of this invention, the B cells are primed B cells.

The cell line described and claimed herein is valuable as a source of the isolated protein which is specifically recognized by monoclonal antibody 5c8 produced by the hybridoma having ATCC Accession No. 10916. The isolated protein is valuable for the information it provides concerning the nucleotide sequences which encode it. The nucleotide sequences are valuable in a new and useful method of producing the soluble activated T cell surface protein described and claimed herein. The cell line is also valuable in new and useful methods for immunizing an animal against a protein antigen and for screening pharmaceutical compounds for their ability to inhibit T cell activation of B cells.

This invention provides an isolated protein which is specifically recognized by monoclonal antibody 5c8 produced by the hybridoma having ATCC Accession No. HB 10916.

This invention further provides that the isolated protein which is specifically recognized by monoclonal antibody 5c8 produced by the hybridoma having ATCC Accession No. 10916, wherein the isolated protein is from the surface of activated T cells and is necessary for T cell induction of terminal differentiation of B cells. In this application, "terminal differentiation" means that the cell are committed to certain secretion and this term is well known for an ordinary skillful practitioner. This invention also provides an isolated protein which is specifically recognized by monoclonal antibody 5c8 produced by the hybridoma having ATCC Accession No. 10916 having an apparent molecular weight of 30 kilodaltons. protein is from the surface of activated T cells and is necessary for T cell activation of B cells.

In one embodiment of this invention, the B cells are resting B cells. In another embodiment of this invention, the B cells are primed B cells.

This invention also provides an isolated protein which is specifically recognized by monoclonal antibody 5c8 produced by the hybridoma having ATCC Accession No. HB 10916 having a sequence, Xaa-Ile-Glu-Xaa-Tyr-Asn-Gln-Xaa-Ser-Pro- (SEQ ID No. 11) at the N-terminus. In the application, "Xaa" may be any amino acid residue.

This invention provides an isolated nucleic acid molecule encoding the T cell surface protein. In one embodiment of this invention, the nucleic acid molecule is a DNA molecule. Preferably, the DNA molecule is a cDNA molecule. The nucleic acid molecules are valuable as products for generating new viral and circular plasmid vectors described below. The nucleic acid molecules are also valuable in a new and useful method of gene therapy, i.e., by stably transforming cells isolated from an animal with the nucleic acid molecules and then readministering the stably transformed cells to the animal. Methods of isolating cells include any of the standard methods of withdrawing cells from an animal. Suitable isolated cells include, but are not limited to, bone marrow cells. Methods of readministering cells include any of the standard methods of readministering cells to an animal.

This invention also provides a gene transfer vector, for example a plasmid or a viral vector, comprising the isolated nucleic acid molecule encoding the activated T cell surface protein.

The gene transfer vectors described and claimed herein are valuable as products useful for generating stably transformed eukaryotic host cells, and thereby in new and useful methods of growing such host cells under conditions suitable for the production of a protein.

This invention further provides a host vector system comprising the gene transfer vector in a suitable host cell. In one embodiment of this invention, the suitable host cell is a bacterial cell, insect cell, yeast cell or mammalian cell.

The host vector system is valuable as a product useful for the large scale synthesis of the activated T cell surface protein by growing the host vector system under conditions suitable for the production of protein. Thus, a method of producing the activated T cell surface protein is also provided. This invention further provides the protein produced by this method.

This invention provides an isolated, soluble protein from the surface of activated T cells necessary for T cell activation of B cells. In one embodiment of this invention, the B cells are resting B cells. In another embodiment of this invention, the B cells are primed B cells.

For the purposes of this invention, a "soluble protein" is a protein free of cell membranes and other cellular components. Preferably, the soluble protein is the protein which is specifically recognized by the monoclonal antibody 5c8 produced by the hybridoma having ATCC Accession No. HB 10916. In one embodiment of this invention, the soluble protein as labelled with a detectable marker, for example, a radioactive isotope, enzyme, dye or biotin. The soluble protein is valuable as a product for making a new and useful pharmaceutical composition.

Thus, a pharmaceutical composition comprising the soluble protein and a pharmaceutically acceptable carrier is also provided. "Pharmaceutically acceptable carriers" means any of the standard pharmaceutically acceptable carriers. Examples include, but are not limited to, phosphate buffered saline, physiological saline, water and emulsions, such as oil/water emulsions.

This invention provides an isolated nucleic acid molecule encoding the soluble protein. In one embodiment of this invention, the nucleic acid molecule is a DNA molecule. Preferably, the DNA molecule is a cDNA molecule.

The nucleic acid sequences described and claimed herein are useful for generating new viral and circular plasmid vectors described below. The nucleic acid molecules are also valuable in a new and useful method of gene therapy, i.e., by stably transforming cells isolated from an animal with the nucleic acid molecules and then readministering the stably transformed cells to the animal. Methods of isolating cells include any of the standard methods of withdrawing cells from an animal. Suitable isolated cells include, but are not limited to, bone marrow cells. Methods of readministering cells include any of the standard methods of readministering cells to an animal.

This invention also provides a gene transfer vector, for example, a plasmid vector or a viral vector, comprising the isolated nucleic acid molecule operably linked to a promoter of RNA transcription.

The gene transfer vectors described and claimed herein are valuable as products useful for generating stably transformed eukaryotic host cells, and thereby in new and useful methods of growing such host cells under conditions suitable for the production of a protein.

This invention further provides a host vector system comprising the gene transfer vector in a suitable host cell. In one embodiment of this invention, the suitable host cell is a stably transformed eukaryotic cell, for example, a stably transformed eukaryotic yeast or mammalian cell. Preferably, the stably transformed cell is a mammalian cell.

The host vector system is valuable as a product useful for the large scale synthesis of the soluble activated T cell surface protein by growing the host vector system under conditions suitable for the production of protein and recovering the protein so produced. Thus, a method of producing the soluble protein is also provided. This invention further provides the soluble protein produced by this method.

This invention provides a method of inhibiting B cell activation in an animal which comprises administering to the animal an effective inhibiting amount of a pharmaceutical composition comprising the monoclonal antibody which specifically recognizes the activated T cell surface protein and a pharmaceutically acceptable carrier. For the purposes of this invention, an "effective inhibiting amount" of a pharmaceutical composition is any amount of the pharmaceutical composition which is effective to bind to a protein on the surface of activated T cells and thereby inhibit T cell activation of B cells. This effective inhibiting amount may easily be determined by an ordinary skilled practitioner using experiments well known in the art. One such experimental approach is by titration. In one embodiment of this invention, the B cells are resting B cells. In another embodiment of this invention, the B cells are primed B cells.

Methods of determining an "effective amount" are well known to those skilled in the art and will depend upon factors including, but not limited to, the type of animal involved and the animal's body weight. In one embodiment of this invention, the animal is a mammal, for example a mouse or a human. Preferably, the mammal is a human.

For the purposes of this invention, "administration" means any of the standard methods of administering a pharmaceutical composition known to those skilled in the art. Examples include, but are not limited to, intravenous, intraperitoneal or intramuscular administration.

The method of inhibiting B cell activation is valuable in a new and useful method for inhibiting the immune response of an animal. In one embodiment of this invention, the animal is a mammal, for example a mouse or a human. Preferably, the mammal is a human.

In one embodiment of this invention, inhibiting the immune response of an animal is valuable as a method of inhibiting the rejection by the animal of a transplant organ, for example, a heart, kidney or liver.

In another embodiment of this invention, inhibiting the immune response of an animals valuable as a method of inhibiting the autoimmune response in an animal suffering from an idiopathic autoimmune disease. Examples of idiopathic autoimmune diseases include, but are not limited to, psoriasis, rheumatoid arthritis, Myasthenia gravis, systemic lupus erythematosus, Graves' disease, idiopathic thrombocytopenia purpura, hemolytic anemia, hyper IgE syndrome, diabetes mellitus and drug-induced autoimmune diseases, e.g., drug-induced lupus.

In another embodiment, this invention provides a method of inhibiting the autoimmune response in humans suffering from autoimmune manifestations of infectious diseases. The autoimmune manifestations may be derived from Reiter's syndrome, spondyloarthritis, Lyme disease, HIV infections, syphilis or tuberculosis.

In still another embodiment of this invention, inhibiting the immune response in an animal is valuable as a method of inhibiting allergic responses, e.g., hay fever or an allergy to penicillin, in the animal.

This invention provides a method of imaging tumor cells or neoplastic cells which express an protein which is specifically recognized by monoclonal antibody 5c8 produced by the hybridoma having ATCC Accession No. 10916 comprising (i) administering to the patient an effective amount of the pharmaceutical composition of monoclonal antibody 5c8 wherein the antibody is conjugated to an imaging agent, under conditions permitting the formation of a complex between the monoclonal antibody and the protein and (ii) imaging any monoclonal antibody/protein complex formed, thereby imaging any tumor cells or neoplastic cells in the patient.

Such tumor cells or neoplastic cells may be derived from T cell tumor, e.g., T cell leukemias or lymphomas. Preferably, the patient is a human patient.

"Administering" means any of the standard methods of administering a pharmaceutical composition known to those skilled in the art. Examples include, but are not limited to intravenous, intramuscular or intraperitoneal administration. Methods of detecting the formation of monoclonal antibody/protein complexes, e.g., by exposure of x-ray film, are well known to those skilled in the art.

An "effective imaging amount" of the pharmaceutical composition is any amount effective for the formation of complexes between the monoclonal antibody and a cell surface protein, such that the complexes can be imaged. Methods of determining an "effective imaging amount" are well known to those skilled in the art and depend upon factors including, but not limited to the type of animal involved, the size of the animal and the imaging agent used. And the exact effective imaging amount may be determined by empirical experiment such as titration which is well known to an ordinary skilled practitioner. In one embodiment of this invention, the imaging agent is a radioisotope.

This invention provides a method of detecting the presence of tumor cells or neoplastic cells which express an protein which is specifically recognized by monoclonal antibody 5c8 produced by the hybridoma having ATCC Accession No. 10916 in an animal which comprises: administering to the animal an amount of a pharmaceutical composition comprising a monoclonal antibody bound to an detectable marker effective to bind to a protein on the surface of tumor cells or neoplastic cells under conditions permitting the formation of complexes between the monoclonal antibody and the protein; clearing any unbound imaging agent from the animal; and detecting the presence of any monoclonal antibody/protein complex so formed, the presence of such complex indicating the presence of tumor cells or neoplastic cells in the animal. The tumor cell may be derived from a T cell leukemia or lymphoma. In a prefered embodiment, the tumor is non-Hodgkin's lymphoma. In one embodiment of this invention, the animal is a mammal, e.g., a mouse or a human. Preferably, the mammal is a human.

"Administering" means any of the standard methods of administering a pharmaceutical composition known to those skilled in the art. Examples include, but are not limited to intravenous, intramuscular or intraperitoneal administration. Methods of detecting the formation of monoclonal antibody/protein complexes, e.g., by exposure of x-ray film or microscopic examination, are well known to those skilled in the art.

An "effective amount" of the pharmaceutical composition is any amount of the pharmaceutical composition effective to detect the presence of tumor cells or neoplastic cells in the animal. Methods of determining an "effective amount" are well known to those skilled in the art and depend upon a number of factors including, but not limited to: the type of animal involved, the size of the blood sample contacted and the detectable marker used. In one embodiment of this invention, the detectable marker is a radioisotope, enzyme, dye or biotin.

This invention provides a method of determining whether an animal harbors tumor cells or neoplastic cells which express an protein which is specifically recognized by monoclonal antibody 5c8 produced by the hybridoma having ATCC Accession No. 10916 which comprises: isolating a sample of blood from the animal; contacting said sample with an amount of pharmaceutical composition comprising a monoclonal antibody, wherein the monoclonal antibody is labelled with a detectable marker, effective to bind to a soluble protein under conditions permitting the formation of a complex between the monoclonal antibody and the protein; and detecting the presence of any monoclonal antibody/protein complex so formed, the presence of such complex indicating the presence of tumor cells or neoplastic cells in the patient.

In one embodiment, the tumor cells are derived from a T cell tumor e.g., a T cell leukemia or lymphoma. In a prefered embodiment, the T cell lymphoma is a non-Hodgkin's lymphoma.

The method provided by this invention as valuable as a new and useful method of detecting the presence of T cell tumor cells in the blood of an animal before the presence of the tumor cells themselves can be detected. The method provided by this invention is also valuable as a new and useful method for determining the effectiveness of the treatment of an animal with an anti-T cell tumor drug, i.e., by determining the level of soluble protein in the blood of the animal, such level being indicative of the effectiveness of the treatment.

It is well known to those skilled in the art that the blood of patients suffering from T cell tumors contains soluble proteins, e.g., the tac antigen, shed from the surface of T cell, tumor cells. Thus, the presence of soluble T cell surface proteins in the blood of an animal is indicative of the presence of T cell tumors in the animal.

For the purposes of this invention, a "soluble protein" is a protein free of cell membranes and other cellular components. In the preferred embodiment of this invention, the soluble protein is the protein which is specifically recognized by the monoclonal antibody 5c8 produced by the hybridoma having ATCC Accession No. H210916 binds.

"Isolating" blood from an animal means any of the generally acceptable methods of withdrawing blood and immediately placing the blood into a receptacle containing an anticoagulant, e.g., heparin EDTA or citrate. Methods of detecting monoclonal antibody/protein complexes are well known to those skilled in the art. Examples include, but are not limited to, exposure of x-ray film and ELISA.

An "effective amount" of the pharmaceutical composition is any amount of the pharmaceutical composition effective to detect the presence of the soluble protein in the blood of the animal. Methods of determining an "effective amount" are well known to those skilled in the art and depend upon a number so factors including, but not limited to: the type of animal involved, the size of the blood sample contacted and the detectable marker used. In one embodiment of this invention, the detectable marker is a radioisotope, enzyme, dye or biotin.

In one embodiment of this invention, the animal is a mammal, e.g., a mouse or a human. Preferably, the mammal is a human.

This invention provides a method of inhibiting the proliferation of tumor cells or neoplastic cells which express the protein specifically recognized by monoclonal antibody 5c8 produced by the hybridoma having ATCC Accession No. HB 10916, in an animal suffering from a tumor or neoplasm, e.g., a T cell leukemia or lymphoma, which comprises administering to the patient an amount of the pharmaceutical composition, comprising a monoclonal antibody unconjugated or conjugated to a therapeutic agent, effective to inhibit the proliferation of tumor cells or neoplastic cells which express the protein specifically recognized by monoclonal antibody 5c8 produced by the hybridoma having ATCC Accession No. HB 10916. In one embodiment or this invention, the animal is a mammal, e.g., a mouse or a human. Preferably, the mammal is a human.

"Administering" means any of the standard methods is administering a pharmaceutical composition known to those skilled in the art. Examples include, but are not limited to intravenous, intramuscular or intraperitoneal administration.

An "effective amount" of the pharmaceutical composition is any amount of the pharmaceutical composition effective to inhibit the proliferation of tumor cells or neoplastic cells which express the protein specifically recognized by monoclonal antibody 5c8 produced by the hybridoma having ATCC Accession No. HB 10916. Methods of determining an "effective amount" are well known to those skilled in the art and depend upon factors including, but not limited to: the type of animal involved, the size of the animal and the therapeutic agent used. In one embodiment of this invention, the therapeutic agent is a radioisotope, toxin, toxoid or chemotherapeutic agent.

This invention provides a method of inhibiting viral infection of the T cells of an animal by the HTLV I virus comprising administering to the animal an amount of a pharmaceutical composition, comprising a monoclonal antibody which specifically recognizes a protein on the surface of activated T cells, effective to inhibit the infection of T cells by the HTLV I virus. In one embodiment of this invention, the animal is a mammal, e.g., a mouse or a human. Preferably, the mammal is a human.

It is well known to those skilled in the art that the CD4 protein is the cellular protein to which the HTLV I virus binds. HTLV I virus thus preferentially infects CD4⁻, but not CD8⁻ T cells. This invention provides a protein, the protein to which monoclonal antibody; 5c8 binds, also specific to CD4⁺ T cells.

This invention provides a method of screening a pharmaceutical compound, e.g., cyclosporin, cyclophosphamide or azothioprine, for its ability to inhibit T cell helper function which comprises: isolating a sample of blood from an animal; culturing said sample under conditions permitting activation of the B cells contained therein; contacting the sample with an amount of the D1.1 cell line or cells expressing the isolated protein which is specifically recognized by monoclonal antibody 5c8 produced by the hybridoma having ATCC Accession No. HB 10916 effective to activate B cells; contacting the sample with an amount of a pharmaceutical compound effective to inhibit T cell induction of terminal differentiation of B cells if the pharmaceutical compound is capable of inhibiting T cell activation; and determining whether the T cell line activates B cells in the presence of the pharmaceutical compound.

In one embodiment of this invention, the B cells are resting B cells. In another embodiment of this invention, the B cells are primed B cells.

In one embodiment of this invention, the blood is isolated from a mammal, e.g., a mouse or a human.

"Isolating" blood from an animal means any of the generally acceptable methods of withdrawing blood and immediately placing the blood into a receptacle containing an anticoaoulant, e.g., heparin, EDTA or citrate. Culturing B cells under "conditions permitting activation of B cells" comprises culturing B cells in the presence of lymphokines.

An "effective activating amount" of the D1.1 cell line is any concentration of the cells in culture effective to activate B cells in the culture. Methods of determining an "effective activating amount" are well known to those skilled in the art.

A method of immunizing an animal against a protein antigen which comprises: isolating a sample of blood including resting B lymphocytes from the animal; recovering resting B cells from said sample; coculturing said resting B cells with an amount of the cell line D1.1 or cells expressing the isolated protein which is specifically recognized by monoclonal antibody 5c8 produced by the hybridoma having ATCC Accession No. HB 10916 to stimulate the B cells to differentiate under conditions permitting the differentiation of B cells; contacting said differentiated B cells with an amount of the protein antigen effective to induce the differentiated B cells to produce an antibody which recognizes the protein antigen; and administering said antibody-producing B lymphocytes to the animal from which the blood sample was isolated.

For the purposes of this invention, "resting B cells" are either undifferentiated, non-antibody synthesizing B cells or memory B cell.

"Isolating" blood from an animal means any of the generally acceptable methods of withdrawing blood and immediately placing the blood into a receptacle containing an anticoagulant, e.g., heparin, EDNA or citrate. Culturing B cells under "conditions permitting differentiation of B cells" comprises culturing B cells in the presence of lymphokines. Methods of administering the B lymphocytes to the animal include any of the generally acceptable methods for administering cells to an animal.

An "effective amount" of the D1.1 cell line or the soluble activated cell surface protein is any amount of the cell line or the soluble protein effective to induce B cells to differentiate. Methods of determining an "effective amount are well known to those skilled in the art.

An "effective differentiating amount" of a protein antigen is any amount of the antigen effective to induce differentiated B cells to produce an antibody which specifically recognizes the antigen.

In one embodiment of this invention, the animal is a mammal, e.g., a mouse or a human. Preferably, the mammal is a human.

In one embodiment of the invention, the antigen is a viral protein antigen, e.g., a hepatitis B virus protein antigen, a Human T cell Leukemia Virus protein antigen or a Human Immunodeficiency Virus protein antigen. In another embodiment of this invention, the antigen is an autoantigen or tumor antigen. Examples of such autoantigens are Ro, La, RNP and rheumatoid factor (IgG) which are well known to an ordinary person skilled in the art.

This invention further provides a method of inducing isotype switching of an antibody producing cell comprising (i) contacting the antibody producing cell with an effective amount of the cell line D1.1 or cells expressing the isolated protein which is specifically recognized by monoclonal antibody 5c8 produced by the hybridoma having ATCC Accession No. HB 10916 to induce the isotype switching under conditions permitting the differentiation of B cells; and (ii) detect the isotype of the antibody producing cell. In one embodiment, the antibody producing cell is a hybridoma cell. In another embodiment, the antibody producing cell is a EBV transformed cell line.

This invention also provides a method of increasing the affinity of an antibody produced by an antibody producing cell comprising contacting the antibody producing cell with effective amount of the cell line D1.1 or cells expressing the isolated protein which is specifically recognized by monoclonal antibody 5c8 produced by the hybridoma having ATCC Accession No. HB 10916 under the condition permitting the contact of the cells; and determining binding affinity of the antibody producing by the antibody producing cell.

This invention provides a method of treating a patient suffering from hypogammoglobulinemia which comprises administering to the patient an amount of the soluble activated T cell surface protein effective to treat the patient for hypogammoglobulinemia. Methods of determining an "effective amount" are known to those skilled in the art. One example of such method is by titration.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

First Series of Experiments

Materials and Methods
Generation and Characterization of 5c8 Monoclonal Antibody Five Balb/c mice were immunized with $2\times10^6$ D1.1 cells in saline intravenously and then boosted intraperitoneally at five, approximately two-week, intervals. The sera of these mice were titrated to test for the presence of antibodies that bound preferentially to Jurkat D1.1 versus B2.7 cells by FACS. One mouse, which showed the best differential titer, received a boost of $2\times10^6$ D1.1 cells intravenously 3 d prior to fusion. Splenocytes from this mouse were fused with $7\times10^7$ murine SP2/0 myeloma fusion partner cells as previously described (Kirchevsky, et al., 1988). The cell mixture was cultured overnight in Dulbeccols Modified Eagle's Medium (DMEM) containing 15% FCS before the fusion product was seeded into 360 8-mm wells. Colonies appeared in 220 wells and all were screened by FACS for differential binding to D1.1 and 92.7 cells. A mAb designated 5c8 was found to bind to D1.1 cells and not B2.7 cells. The 5c8 clone was subcloned multiple times until monoclonality was established. The 5c8 mAb was found to be IgG2a by Elisa (HYCLONE®, Logan, Uath).

Monoclonal Antibodies

The following mAbs were produced by hybridomas available from the American Type Culture Collection (Manassas, Va.): OKT11 (anti-CD2), OKT10(anti-38), OKT8(anti-CD8), OKT6(anti-CD1a), OKT4(anti-CD4), OKT3(anti-CD3), OKT1(anti-CD5), 3A1(anti-CD7), tac(anti-CD25), T-HB5(anti-CD21, CR2), W6/32(anti-MHC class I), AB2.06 (anti-MHC class II), L243 (anti MHC class II) 93F10(anti-MHC class II), TS1/22.1.13(anti-LFA-1a), TS1/18.1.2.11.4(anti-LFA-1β), TS2/9.1.4.3(anti-LFA-3) and 187.1(anti-human Ig(Fab)). These mAbs were either used at saturating concentrations of hybridoma supernatants, or purified from ascites fluid on protein A columns (3Biorad, Rockville Center, NY). The anti-Jurkat TCR clonotypic (anti-vβ8) mAb 16G8 and a panel of other such anti-TCR mAb were purchased from Diversi-T, T Cell Science (Cambridge, Mass.). The mAb OKT4A was purchased from Ortho Pharmaceutical (Raritan, N.J.), TCRδ-1 was the gift of Dr. Michael Brenner, Harvard Medical School (Boston, Mass.). M241(anti-CD1c) was the gift of Dr. Cox Terhorst of Harvard Medical College. FITC labeled ant-CD23-PE mAbs and unlabelled anti-CD69 were purchased from Becton Dickinson (Mountainview, Calif.). FITC labeled anti-IgM was purchased from Tago (Burlingame, Calif.). Kolt-4 (anti-CD28) and anti-CD27 were purchased from Accurate Scientific (Westbury, N.Y.).

Recombinant proteins, rIL-4 was purchased from Genzyme (Cambridge, Mass.). rIL-2 was a gift of Hoffmann-LaRoche (Nutley, N.J.).

Cytofluorographic Analysis

Approximately $10^6$ cells were incubated with saturating concentrations of the indicated mAbs for 45 min at 4° C. In the presence of 80 µg/ml heat-aggregated human IgG (International enzyme, Fallbrook, Calif.). Cells were washed to remove unbound mAb before incubation with goat anti-mouse Ig secondary antibody coupled to fluorescein (Cappel, Cochranville, Pa.).

For two color analysis, cells were reacted with the indicated directly coupled FITC or Phycoerythrin (PE) conjugated mAb for 45 min at 4° C. In the presence of aggregated human IgG. Prior to analysis, cells were washed and resuspended in PBS. Fluorescence intensity was measured on a FACSCAN Cytofluorograph with the consort-30 software (Becton-Dickinson, Mountainview, Calif.). In experiments involving co-culture of B cells with Jurkat clones, the Jurkat cells were excluded from the analysis of B cell fluorescence by gating on the distinct population of cells with low forward and side light scatter. In experiments with PMA and PHA activated cells, dead cells were excluded from analysis by treatment with propridium iodide and electronic FACS gating.

Cell Lines

The following cell lines are available from the American Type Culture Collection (Manassas, Va.): HPB-ALL, Jurkat, CEM, PEER, MOLT-IV, K562, Ramos, Raji and U937. BA is an Epstein Barr virus transformed B cell line that has been previously reported (Bank, e. al., 1986). H9 is available from the HIV Repository (Rockville, Md.). HLA typings was performed by Dr Elaine Reed of the Department of Pathology, Columbia University (One Lambda, Los Angeles, Calif.). Jurkat D1.1 and B2.7 were negative for mycoplasma by the Mycotect kit (GIBCOC®, Grand Island, N.Y.) and by the DNA hybridization method (Genprobe, La Jolla, Calif.).

Isolation of Cell Populations

Peripheral blood lymphocytes were obtained from the freshly drawn blood of healthy volunteers by centrifugation on Ficoll-Hypaque (SIGMA®, St. Louis, Mo.) or Leukoprep (Becton-Dickson). T cells were positively selected with neuraminidase treated sheep erythrocytes. $CD4^+CD8^-$ and $CD4^-CD8^+$ cell subsets were isolated by anti-CD8 or anti-CD4 mAb treatment, respectively, followed by complement mediated lysis as previously described (Rogozinksi, et al., 1984). B cells were derived from the population of cells that did not pellet through ficoll-hypaque after two rounds of resetting with neuraminidase treated sheep erythrocytes.

B cells were further purified by either density centrifugation or by positive selection on an anti-Ig column. In the first method, E− cells were cultured overnight in polystyrene flasks (37° C., 5% $CO_2$) to delete the macrophage by adherence. These non-T cell, non-macrophage cells were fractionated into high and low density fractions in a discontinuous 30%/50%/100% percoll gradient by centrifugation at 2300 rpm for 12 min. High-density cells were obtained from the 50/100% interface and low-density cells from the 30/50% interface (Crow, et al., 1985). The high density (resting) cells were typically 60–80% $CD20^+$, 55–80% $IgM^+$ and <5% $CD3^-$ and <5% $CD23^+$ (background). In other experiments (where indicated) B cells were purified by SEPHADEX® G-200 anti-F(ab)$_2$ Ig affinity chromatography into $sIg^+$ cells as has been described (Rogozinski, et, al., 1984; Friedman, et al., 1976). The $sIg^+$ populations were typically <5% $CD3^+$, <10 $CD2^+$ and >90% $CD20^+$ when analyzed by FACS.

SDS Polyacrylamide Gel Electrophoresis

Jurkat clones were iodinated by the lactoperoxidase method, solubilized in 1% NP40, 25 mM Tris-Buffered PBS containing iodoacetamide and 10 μm-PMSF. The cell lysates were reacted with protein A-4B SEPHAROSE® beads (PHARMACIA®, Uppsula, Sweden) that were coated with mAb 187.1 (anti-human F(ab)Ig) and approximately 10 μg of the indicated mAb. After washing the beads to remove non-specifically bound proteins, the precipitated proteins were denatured by heating in SDS in the presence or absence of 2-ME. The denatured proteins and pre-stained MW markers (Biorad, Rockville Center, NY) were electrophoresed through 12% polyacrylamide in 12 cm gels (Biorad Protean Gel, Rockville Center, NY) and dried gels were used to expose X-ray film (KODAK®, Rochester, NY).

Mitomycin-C and Paraformaldehyde Treatments

Jurkat cells ($10^7$/ml) were treated with 50 μg/ml mitomycin-C (SIGMA®, St. Louis, Mo.) for 60 min at 37° C. The mitomycin-treated Jurkat cells were washed twice, resuspended in mitomycin free media and then cultured for 45–60 min at 37° C. The cells were washed two additional times and then added to the B cell cultures. In fixation experiments, T cells were treated with freshly made 0.5% paraformaldehyde for 5–10 minutes, quenched with 0.2 M L-lysine and washed five times before addition to cultures of 3 cells.

T Cell Activation

In experiments studying expression of 5c8 Ag, resting T cells were cultured in the presence or absence of 10 μg/ml phorbol myristate acetate (PMA) (SIGMA®, St. Louis, Mo.) and 10 μg/ml PHA (SIGMA®). In experiments studying the metabolic requirements for 5c8 Ag expression, T cells were activated in the presence of 100 μm cyclohexamide (SIGMA®) or 10 μg/ml acinomycin D (SIGMA®).

In experiments studying the induction of CD23 expression on high density B cells by activated T cells, the mAbs OKT3 or OKT4 were immobilized on the surfaces of 24 well culture plates by incubation of 10 μg/ml of mAb in PBS for 1 h. Control wells were incubated in PBS containing no mAb. After washing unbound mAb coated plates at $2\times10^6$ cell/well in the presence of 10 ng/ml phorbol dibutyrate (PDB) (Sigma) for 6 h. The cells were removed by vigorous pipetting, washed and fixed with 0.5% paraformaldehyde as described above before culture at a 1:1 ratio with $2\times10^5$ high density, PERCOLL® isolated, resting B cells for 18 h. B cell CD23 expression was determined by 2-color FACS as described above.

Assays of B Cell Activation and Differentiation

In experiments measuring the induction of B cell surface CD23 expression, $2\times10^5$ high density B cells were added to the indicated number of Jurkat cells or T cells in 200 μl of Iscove's Modified Dulbecco Medium (IMDM) 10% FCS round bottom microtiter wells (Nunc) and assayed for CD23 expression after 18–24 h. Two chamber experiments were performed with $1\times10^6$ Jurkat cells in the presence or absence of $1\times10^6$ B cells separated from $1\times10^6$ cells by 45-μm culture plate inserts from MILLIPORE® (Bedford, Mass.).

B cell proliferation was measured by culturing $10^5$ B cells with equal numbers of mitomycin-C-treated E⁺ cells or Jurkat clones in flat bottom microtiter wells (NUNC) in the presence or absence of PHA (5 μg/ml). The cultures were pulsed with 1 μCi (H,) thymidine (New England Nuclear, Boston, Mass.) after 60 h and harvested 16 h later on glass fiber filter paper (Cambridge Technology, Watertown, Mass.). Beta scintillation cpm were measured on a beta counter (LKB® Rackbeta counter, Model 1209). The measurement of plaque forming colonies (PFC) was a modification of the Jerne hemolytic plaque assay (Rogozinski, et al., 1984). Briefly, $2.5\times10^5$ B cells were cultured with varying numbers of mitomycin-C treated Jurkat cells or untreated freshly isolated, autologous T cells for 6 days in the presence or absence of a 1:400 dilution of poleweed mitogen (PWM) (GIBCO®, Grand Island, N.Y.). The cells were washed twice and resuspended in Hanks balanced salt solution. From an appropriate dilution, 50 ul of cultured cell suspension was mixed with: 10 μl of an 11% solution of SRBC that had been coated with rabbit anti-human Ig by chromic chloride, 10 μl of diluted rabbit anti-human Ig and 10 μl of guinea pig complement. These mixtures were introduced into duplicate glass chambers and cultured for 2 h at 37° C. Plaques were counted using a dissecting microscope and expressed as plaque forming colonies (PFC) $10^6$ B cells.

ELISA for Ig isotype quantitation were performed by coating polystyrene 96-well plates (IUMMULON® II, Dynatech Laboratories, Chantilly, Va.) with dilutions of goat anti-human IgA, IgG, or IgM (Tago, Burlingame, Calif.) In carbonate buffer, pH 9.6, for 18 h at 4° C. The plates were washed with 0.05% TWEEN® in PBS, and nonspecific sites were blocked by a 2 h incubation of 1% BSA-PBS. After washing, 50 μl of cell culture supernatants or Ig isotype standards (Rockland, Gilbertsville, Pa.) were added to the wells and allowed to bind for 2 h. Next, goat anti-human is coupled to alkaline phosphatase (Tago) was added to detect bound human Ig. After 2 h, the wells were washed and p-nitrophenyl phosphate was added. Absorbance was measured at 405 nm in a Molecular Devices VMAX® device (Palo Alto, Calif.). Samples were assayed in triplicate. Error bars represent calculated standard deviation from curve fit and interpolation (Delta-Soft, BioMetallics, Inc. Princeton, N.J.).

Role of CD4 in T Cell function

To study the role of CD4 in T cell functions, a CD4⁻ Jurkat clone (D1.1) was isolated from a culture that spontaneously developed a CD4⁻ subpopulation identified by a negative peak on FACS analysis. The lack of CD4 surface expression was relatively specific in that the cell surface phenotype of Jurkat D1.1 with respect to the binding of a large panel of mAb was similar to a CD4⁺ clone, Jurkat B2.7 (FIGS. 1A–H and Table 1). Although the differential expression of CD4 was the only qualitative difference between these subclones, some of the other molecular structures studied were expressed at quantitatively different levels. For example, Jurkat D1.1 expressed more CD2 and MHC class (HLA) molecules than Jurkat B2.7. However, Jurkat D1.1 expressed fewer CD28 molecules and fewer TCR-α/β(vβ8)/CD3 complexes than Jurkat B2.7 (FIGS. 1A–H and Table 1). In addition to their shared reactivity with the clonotypic anti-TCR mAb, Jurkat D1.1 and B2.7 were HILA identical (A3, 34,2, 16) and distinct from an unrelated T cell leukemic line, HPB-ALL (A9). Together, these data demonstrated that Jurkat D1.1 was a CD4⁻ subclone of Jurkat and that the absence of CD4 molecules was a relatively specific alteration in its surface phenotype.

TABLE 1

CELL SURFACE PHENOTYPES OF JURKAT CLONES D1.1 AND B2.7

| CD No. | Molecule | mAb | Mean Fluorescence Intensity[a] | |
|---|---|---|---|---|
| | | | D1.1 | B2.7 |
| | TCRα/β | BMA-031 | 10 | 40 |
| | TCRvβ8 | 16G8 | 30 | 70 |
| | TCR-vβ5 | W112 | 0 | 0 |
| | MHC-classI | W6/32 | 190 | 70 |
| | MHC-classII | 2.06 | 0 | 0 |
| CD1a | T6 | OKT6 | 10 | 10 |
| CD1c | | M241 | 10 | 10 |
| CD2 | T11 | OKT11 | 100 | 10 |
| CD3 | TCR complex | OKT3 | 30 | 80 |
| CD4 | T4 | OKT4 | 0 | 130 |
| CD5 | T1 | OKT1 | 20 | 90 |
| CD7 | | 3A1 | 200 | 190 |
| CD8 | T8 | OKT8 | 0 | 0 |
| CD11a | LFA-1α | TS1/22.1.13 | 40 | 100 |
| CD14 | | My2 | 0 | 0 |
| CD16 | FcεRII | 3G8 | 20 | 20 |
| CD18 | LFA-1β | TS1/18.1.2.11.4 | 30 | 80 |
| CD21 | CR2 | HB-5 | 0 | 0 |
| CD23 | FcγRII | leu20 | 0 | 0 |
| CD25 | tac. IL-2Rα | tac | 0 | 0 |
| CD26 | DPPIV | taq-1 | 0 | 0 |
| CD28 | 9.3. gp44 | KOLT-4 | 30 | 70 |
| CD29 | | 4B4 | 140 | 110 |
| CD38 | T10 | OKT10 | 40 | 30 |
| CDw32 | FcτRII | 32.2 | 0 | 0 |
| CD45RA | T200. LCA | 2H4 | 30 | 40 |
| CD45RO | T200. LCA | UCHL1 | 10 | 20 |
| CDw49 | VLA-1 | 1B.3 | 0 | 0 |
| CD58 | LFA-III | TS2/9.1.4.3 | 40 | 60 |
| CD64 | FcγRI | IV 3 | 0 | 0 |

[a]Numbers represent mean fluorescence intensity (arbitrary units) as determined by FACS. Background is subtracted and numbers are rounded off to the nearest ten units.

In functional studies, the ability of CD4+ (B2.7) and CD4− (D1.1) Jurkat cells to induce resting B cells to express CD23, a marker of B cell activation were compared (Crow, et al., 1986; Jover, et al., 1989; Crow, et al., 1989). Surprisingly, co-culture of B cells with CD4− Jurkat (D1.1) but not CD4+ Jurkat cells (B2.7) induced CD23 expression on greater than 60% of B cells (FIGS. 2A–F). The induction of B cell surface CD23 expression by Jurkat D1.1 was maximal at 20–24 h at a ratio of 1:1 D1.1 cells to B cells (FIGS. 3A–B). In contrast, the B2.7 Jurkat subclone did not activate B cells at high ratios (FIGS. 3A–B) or at long periods of coculture (up to 48 h, not shown). In addition, Jurkat D1.1 was unique in this ability compared with other T cell (H9, HPB-ALL, MOLT-IV, CEM) and non-T cell (U937) leukemic lines (not shown). Jurkat D1.1 induced B cell CD23 expression selectively because the levels of other B cell surface molecules such as ITM (FIGS. 2A–F), CD20 (FIGS. 2A–F), or class I MHC were not affected. The effect of Jurkat D1.1 on B cell activation was consistently observed on B cells from over 25 unrelated donors, suggesting that the effect was neither Ag nor MHC restricted.

B cell CD23 expression is an early and possibly intermediate stage in terminal B cell differentiation into Ig-secreting cells. Other stimuli, besides those contributed by activated T cell surfaces are required to mediate substantial B cell proliferation and differentiation. Because the measurements of B cell proliferation or differentiation require several days of culture, the proliferation of the Jurkat clones was inhibited by pretreatment with mitomycin-C, which did not abolish their capacity to activate B cells (Table 2).

TABLE 2

EFFECTS OF MITOMYCIN-C AND ANTIBODIES TO IL-4 ON B CELL CD23 EXPRESSION INDUCED BY JURKAT D1.1 CELLS

| B cells plus | C | rIL-4 | rIL-2 | Jurkat clones | | | |
|---|---|---|---|---|---|---|---|
| | | | | D1.1 | B2.7 | D1.1/M | B2.7/M |
| | 14 | 64 | 17 | 81 | 16 | 57 | 14 |
| Anti-IL-4 | ND | 28 | ND | 84 | ND | 64 | ND |
| Anti-IL-2 | ND | 60 | ND | 86 | ND | 60 | ND |

Shown are the percentages of CD20(Leu-16)+ B cells expressing CD23 as determined by two-color FACS analysis with anti-CD20(Leu-16)-FITC and anti-CD23 PE. High density PERCOLL®-fractionated B cells (2×10$^5$) were cultured alone or with an equal number of either Jurkat B2.7 or D1.1 cells as indicated for 20 h. Where indicated, purified polyclonal rabbit anti-IL-4 or anti-IL-2 Ig was added at the initiation of the experiment to final concentrations of 1.25 μg/ml. Where indicated, rIL-2 or rIL-4 were added to indicated cultures to final concentrations of 25 U/ml. Cells analyzed were gated by forward and side light scatter to exclude the larger D1.1 or B2.7 cells (when present) from the analysis. C: Control; D1.1/M: D1.1 cells treated with mitomycin-C; B2.7/M: B2.7 cells treated with mitomycin-C; ND: not determined.

Figure 4B:
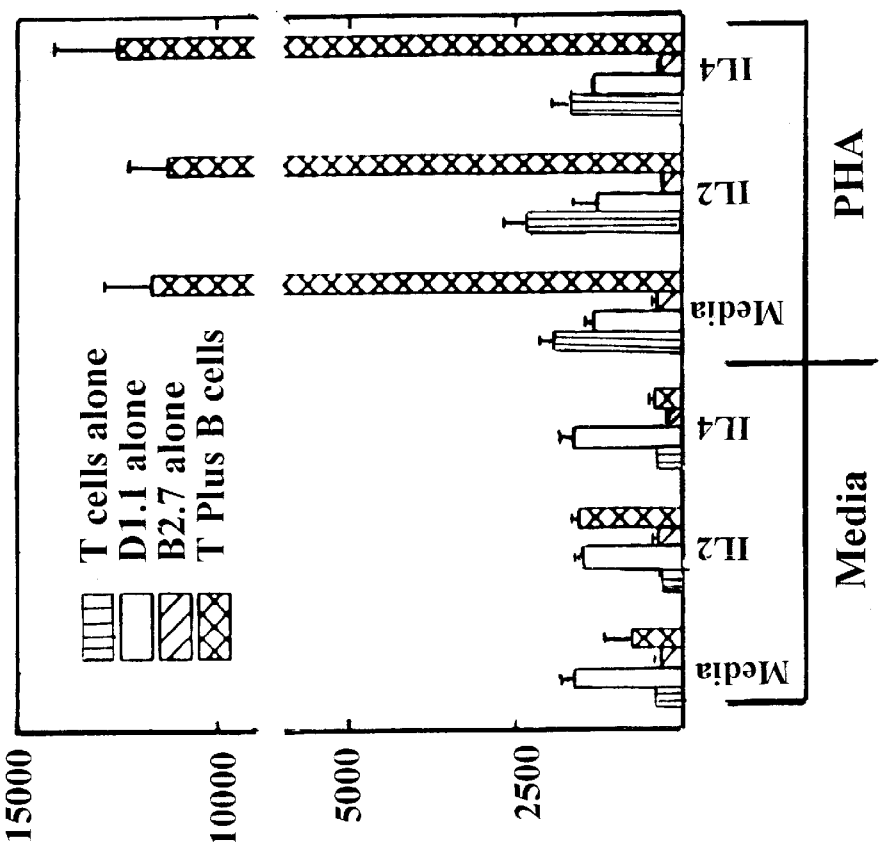
FIGS. 4A–B. Jurkat D1.1 induces B cell proliferation in the presence of PHA.
Figure 4A:
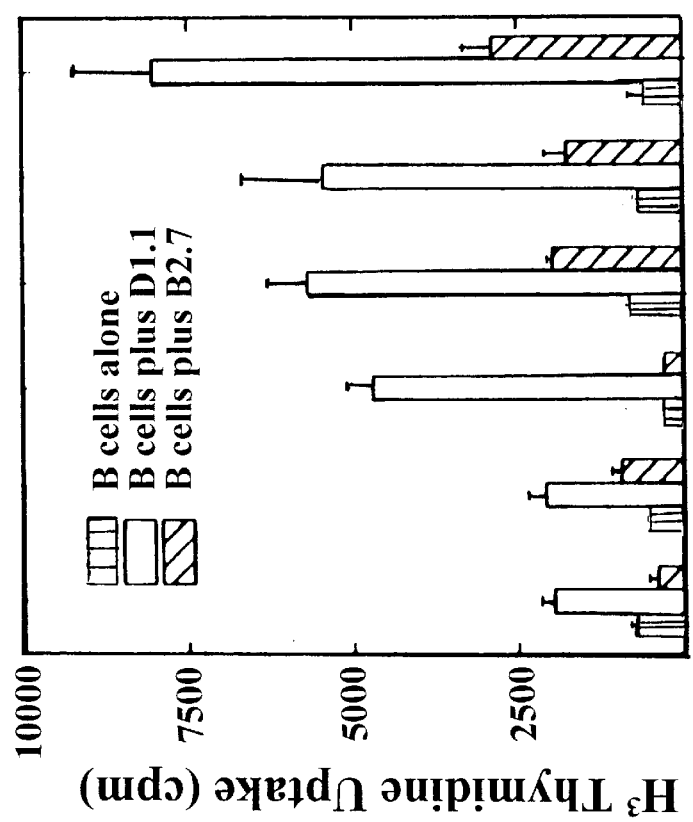
Figure 5C:
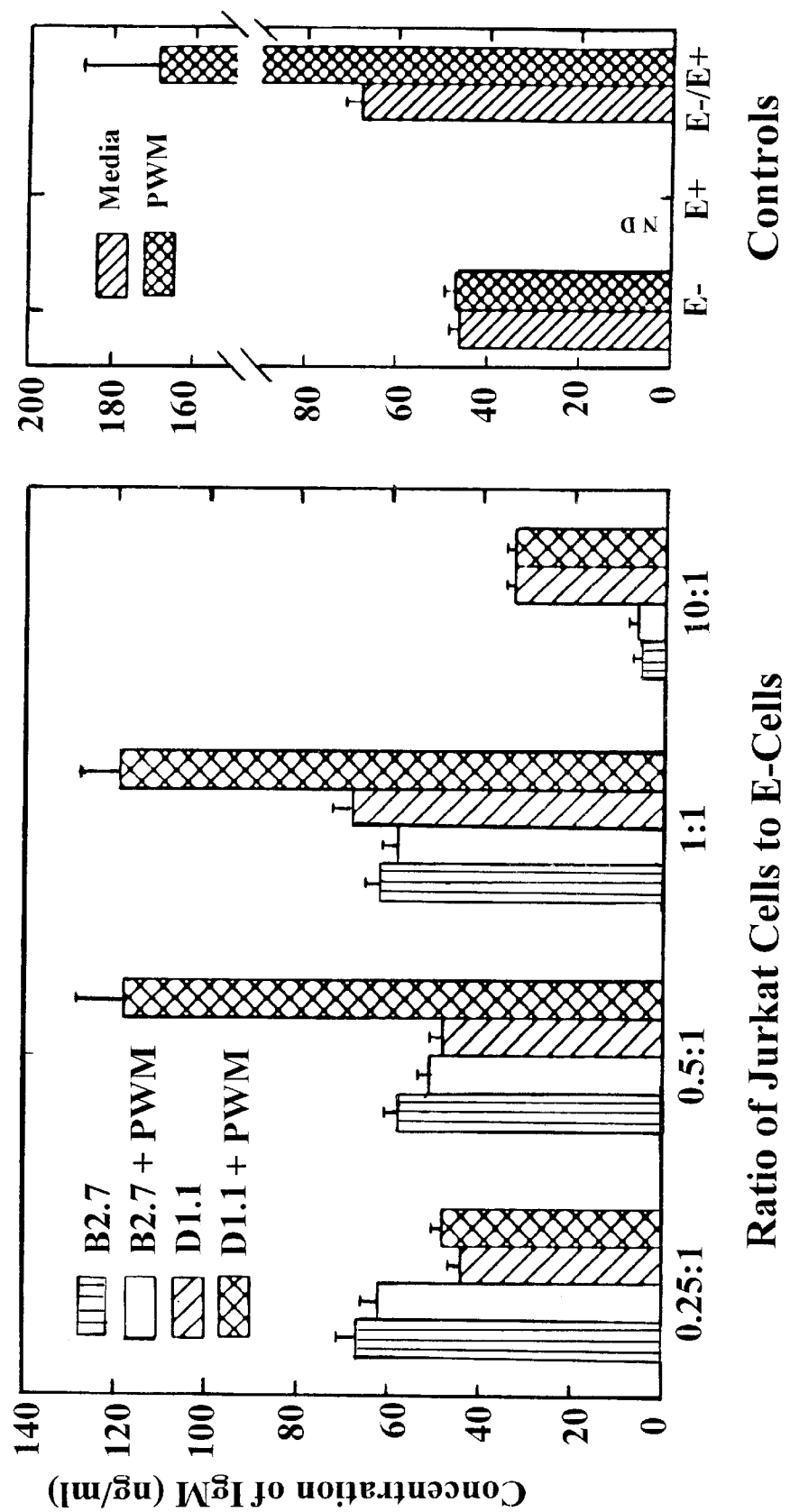
Figure 6A:
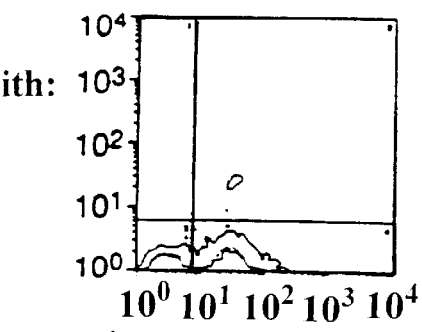
FIGS. 6A–E. rIL-4 but not D1.1 increased B cell sIgM expression. Shown are fluorescence histogram (FACS) analyses resulting from experiments similar to those in FIGS. 3A–B. The median channel fluorescence of IgM is shown on the right column.
Figure 6B:
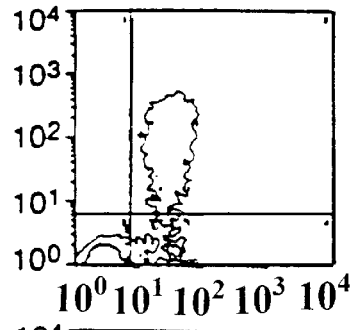
Figure 6C:
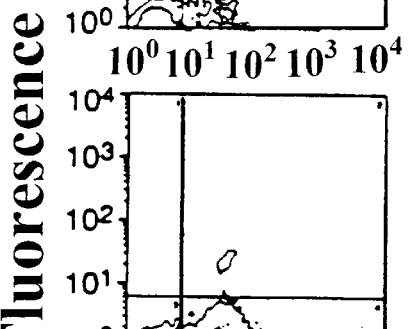
Figure 6D:
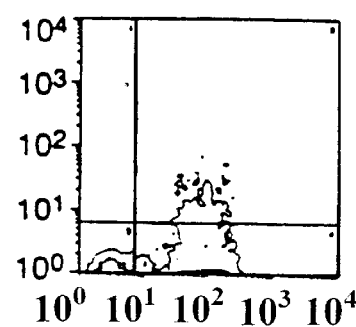
Figure 6E:
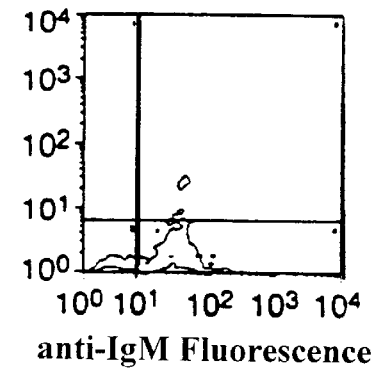
Figure 8A:
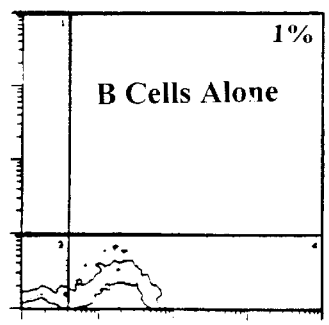
FIGS. 8A–E. Monoclonal antibody 5c8 inhibits Jurkat D1.1 induced CD23 expression by B Lymphocytes. Shown are two color FACS analyses of adherence depleted, high density B cells after 24 h of culture using anti-IgM-FITC (the X axis) and anti-CD23-PE (on the Y axis). The number in the upper right hand corner of the FACS tracings represents the percentage of IgM⁻ cells that expressed CD23.
Figure 8B:
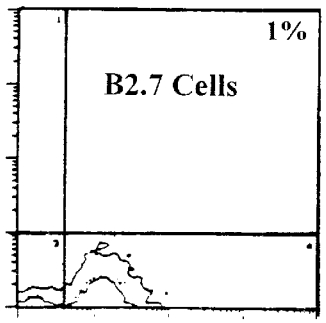
Figure 8C:
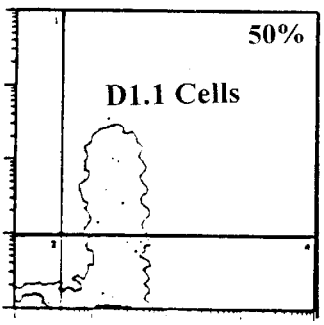
Figure 8D:
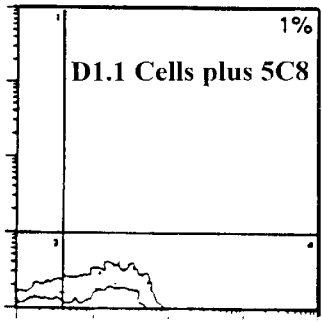
Figure 8E:
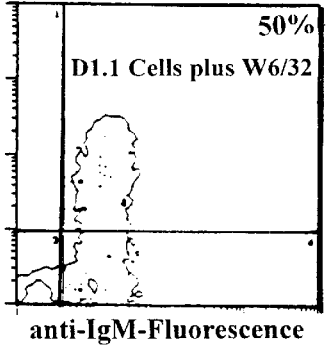

Mitomycin-C treated CD4− Jurkat D1.1 and CD4+ Jurkat B2.7 were then studied for their ability to induce B cell proliferation or terminal B cell differentiation into Ig-secreting cells. In the presence of T cell-dependent B cell mitogens (Doech, et al., 1980), Jurkat D1.1− but not B2.7− induced B cell proliferation measured by DNA synthesis (FIGS. 4A–B) and differentiation to Ig-secreting cells measured by reverse hemolytic plaque assay (FIG. 5A). In addition, the isotype of secreted antibody was characterized by quantitative ELISA. Jurkat D1.1 but not B2.7 induced the secretion of IgG and to a lesser extent, IgM into the culture supernatant (FIGS. 5B and C). Taken together, these data show that Jurkat D1.1 but not Jurkat B2.7 shared with activated T cells the functional capacity to support B cell differentiation and the secretion of IgM and IgG.

Role of Diffusible Factors in B Cell Activation

D1.1 supernatants did not induce B cell CD23 expression (FIGS. 3A–B). Two chamber experiments were performed in which resting B cells were cultured in a chamber that was separated by a permeable membranes from either lymphokine containing media or from cultures of D1.1 cells in the presence or absence of B cells. In an experiment in which B cells (66% IgM+) were cultured in a chamber with a 0.45-mμ membrane. rIL-4 (25 U/ml) induced CD23 expression on 28% of IgM+ B cells as measured by by two-color FACS analysis. In contrast, D1.1 cells did not activate B cells in the other chamber to express CD23 (4.7% for D1.1 vs 4.0% background). In addition, coculture of D1.1 cells with B cells in one chamber did not activate B cells in the other chamber to express CD23 (4.9%). However, D1.1 cells potently induced CD23 expression by the B cells with which they could establish direct contact (76% vs 8.4% for B2.7 cells). Taken together, these data failed to support a role for diffusible factors in mediating the D1.1 effect on B cells.

Because rIL-4 was known to activate B cells to express CD23 (Rabin, et al., 1985), the potential role of IL-4 in mediating this effect in addition to inducing CD23 expression on B cells was further studied. rIL was known to up-regulate B cell sIgM+ expression (Shields, et al., 1989). Whereas rIL-4 induced CD23 expression and sIgM up-regulation in a dose-dependent manner, D1.1 cells induced CD23 expression but did not up-regulate B cell sIgM (FIGS. 6A–E). The effect of D1.1 cells on B cell proliferation was also distinct from that of rIL-4 (FIGS. 4A–B). D1.1 cells, but not rIL-4 induced B cell proliferation in the presence of PHA. Interestingly, rIL-4 and D1.1 cells collaborated to induce B cell proliferation in the absence of PHA and augment D1.1 induced proliferation in the presence of PHA. Taken together these data suggest that the effect of D1.1 cells on B cells are distinct from those induced by IL-4. However, to directly examine the role of IL-4 in D1.1's effect on B cells, neutralizing antibodies to IL-4 were used. Concentrations of anti-IL-4 antibodies that inhibited both the CD23 induction and sIgM up-regulation mediated by rIL-4 (FIGS. 6A–E) did not inhibit D1.1-mediated B cell CD23 expression (Table II). These data demonstrated that IL-4 alone did not account for the effect of D1.1 on B cells. Taken together, these results strongly suggested that cell-cell contact and not secreted factors accounted for the effects of D1.1 on B cell activation.

To substantiate the idea that cell-cell contact mediated the D1.1 effect on B cells, Jurkat D1.1 and control, B2.7 cells were fixed with 1% paraformaldehyde. Although paraformaldehyde fixation decreased the potency of Jurkat D1.1 to activate B cells, fixed D1.1 cells remained competent to induce B cell CD23 expression whereas, fixed B2.7 cells did not alter CD23 expression from the background level. At a ratio of 5:1 fixed D1.1 cells:B cells, 63% of B cells were induced to express CD23 as compared with 80% for unfixed D1.1 cells. Taken together, these data suggest that surface structures on Jurkat D1.1 are sufficient to induce B cell activation.

Characterization of Cell Surface Proteins on Activated CD4+ T Cells that Mediate Helper Effector Function In order to characterize cell surface proteins on activated CD4+ T cells that mediate helper effector function, mice were immunized with the D1.1 clone of Jurkat that possess contact dependent helper effector function (Yellin, et al., 1991). Monoclonal antibodies (mAb) were generated and hybridoma supernatants were screened for differential binding to the D1.1 clone and a non-helper Jurkat clone, B2.7.

A murine IgG2a mAb, termed 5c8, was identified that bound specifically to the surface of D1.1 cells and not to the surface of the non-helper, B2.7 cells (FIGS. 7A–L). The mAb 5c8 did not bind to a variety of other cell lines including: the T cell leukemia lines, CEM, H9, Molt-4 and Peer; the B cell derived cell lines, BA, Raji or Ramos; the myelomonocytic cell line, U937; or the erythroleukemia cell line, K562 (see Table 3 below).

TABLE 3

EXPRESSION OF 5c8 Ag ON CELL POPULATIONS AND CELL LINES

|  | Resting | Activated |
| --- | --- | --- |
| Cell Lines |  |  |
| Jurkat D1.1 | + | + |
| Jurkat B2.7 | − | − |
| CEM | − | − |
| H9 | − | ND |
| Molt-4 | − | − |
| PEER | − | − |
| BA | − | ND |
| Raji | − | ND |

TABLE 3-continued

EXPRESSION OF 5c8 Ag ON CELL POPULATIONS AND CELL LINES

|  | Resting | Activated |
| --- | --- | --- |
| Ramos | − | ND |
| U937 | − | − |
| K562 | − | ND |
| Cell Populations |  |  |
| T cells | − | + |
| B cells | − | − |
| Monocytes | − | − |

These data derive from FACS analyses of mAb 5c8 binding to the indicated cell lines or cell populations. The presence of mAb 5c8 binding was determined relative to FACS staining of appropriate positive and negative control mAbs for each cell line or population. Nd: Not determined.

To assess whether mAb 5c8 reacts with a molecule that is functionally relevant to the helper capacity of the Jurkat clone D1.1, the effect of mAb 5c8 is studied in assays of D1.1 induced CD23 expression on B cells. The mAb 5c8 potently inhibited Jurkat D1.1 induced cell activation (FIGS. 8A–E). In contrast, the isotype control mAb, W6/32 did not inhibit D1.1 mediated B cell activation. The data presented here suggest that the 5c8 Ag plays a critical role in the helper effector function of D1.1 cells.

Biochemical Characterization of the Antigen Recognized by mAb 5c8

Figure 9A:
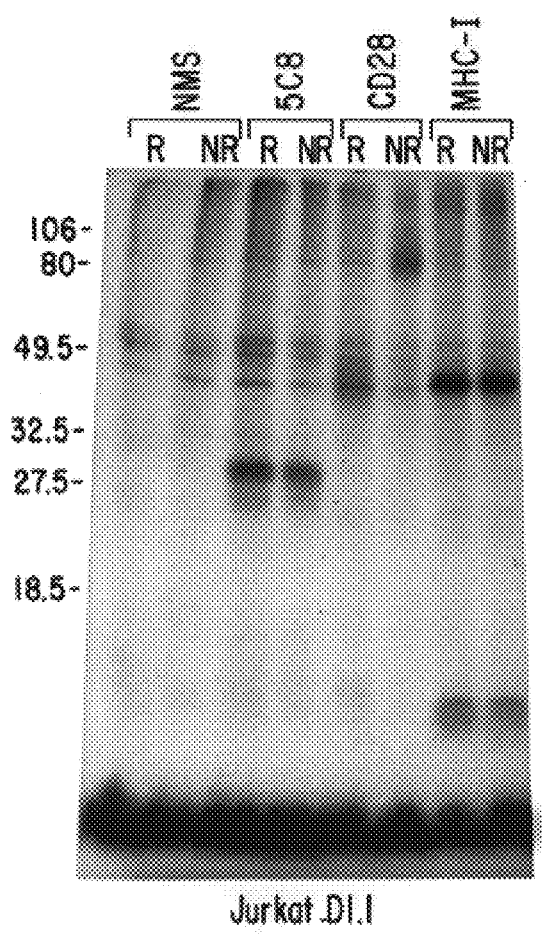
FIGS. 9A–B. SDS/PAGE analysis of surface proteins immunoprecipitated by mAb 5c8 and control mAbs.
Figure 9B:
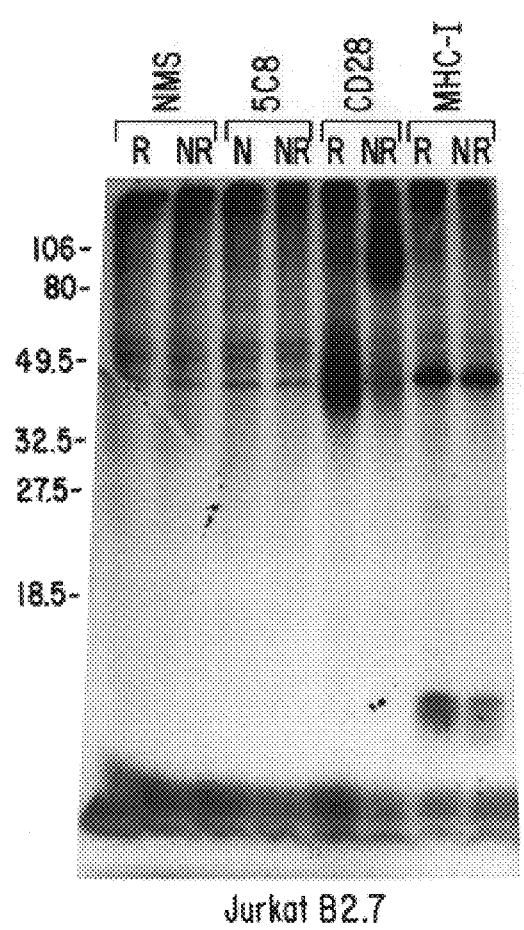
Figure 11A:
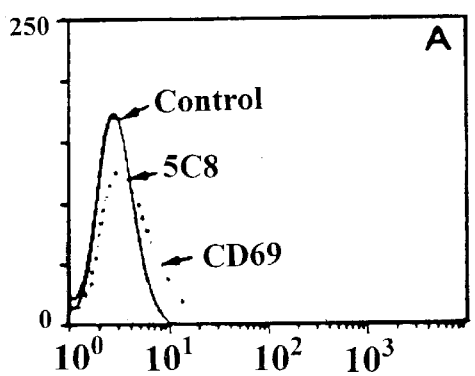
FIGS. 11A–F. Kinetics of expression of 5c8 on isolated $CD4^+$ or $CD8^+$ T cell subsets. Shown is a fluorescence histogram of $CD4^+$ or $CD8^+$ cells at the indicated time points after freshly purified T cell subsets were activated with PHA (10 µg/ml) and PMA (10 ng/ml). Solid line: 5c8 binding; dashed line: IgG2a control; and dotted line: anti-CD69.
Figure 11D:
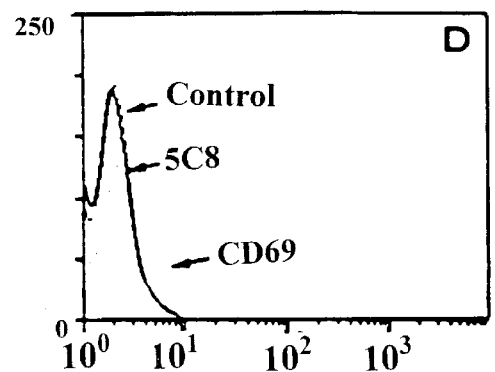
Figure 11B:
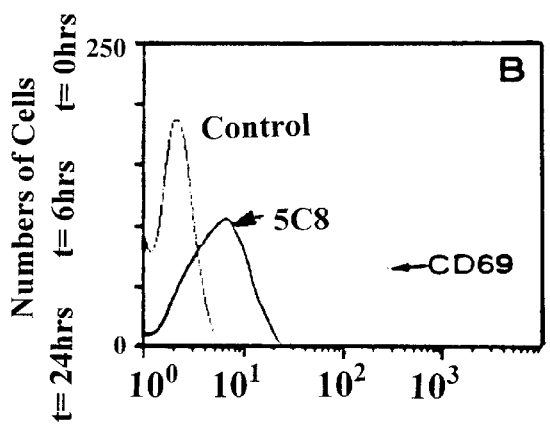
Figure 11E:
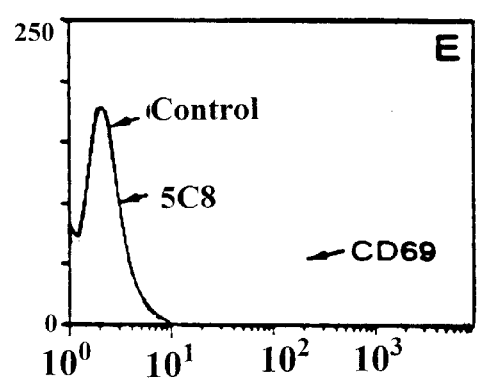
Figure 11C:
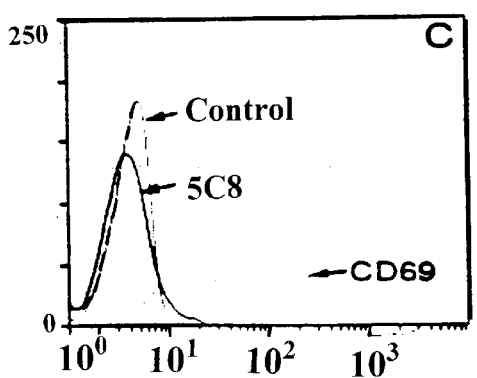
Figure 11F:
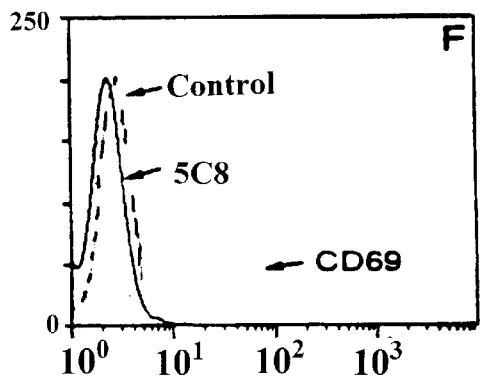

In, order to biochemically characterize The antigen recognized by mAb 5c8, immunoprecipitations were performed with mAb 5c8 or control mAbs that recognized Class I MHC (W6/32) or CD28 (Kolt-4) antigens on cell lysates of surface iodinated Jurkat D1.1 cells and control, non-helper Jurkat 22.7 cells that lack surface mAb 5c8 binding. The mAb 5c8 immunoprecipitated a protein that migrated on SDS/PACE at 30 kDa from lysates of the helper clone D1.1 but not from the control B2.7 lysates (FIGS. 9A–B).

The protein species immunoprecipitated by mAb 5c8 was not affected by reduction with 2-mercaptoethanol (2-ME) suggesting that the 30 kDa band was neither a disulfide linked homodimer nor disulfide linked to another protein that was not accessible to iodination. In contrast, the control, anti-CD28 mAb, KOLT-4 immunoprecipitated (FIGS. 9A–B) an 88 kDa band in the absence of 2-ME and a 44 kDa band in the presence of 2-ME that is consistent with published reports (Martin, et al., 1986) and with the interpretation that this structure is a disulfide linked homodimer. The control mAb W6/32 precipitated a non-disulfide linked heterodimer of 43 and 12 kDa MW proteins (FIGS. 9A–B). These data suggested that the mAb 5c8 recognized a 30 kDa MW non-disulfide linked protein species from the surface of D1.1. cells.

Characterization of the Expression of 5c8 Ag by Normal Lymphoid Cells

The binding of mAb 5c8 or a variety of control mAbs were studied by FACS on freshly isolated, T and B lymphocytes, monocytes and PMA and PHA stimulated T cells. Although, resting T or B lymphocytes or monocytes did not express 5c8 Ag (see Table 3 above and FIGS. 10A–L), a subset of activated T cells was found to express 5c8 Ag, 5 h after activation with PMA and PHA (FIGS. 10A–L).

To characterize the kinetics and cellular distribution of 5c8 Ag expression, the binding of mAb 5c8 to T cells was studied by FACS at various intervals after T cell activation. The CD69 molecule, which is a 32/28 KDa disulfide linked heterodimer, was selected as a control because it is known to be induced rapidly on virtually all T cells after T cell activation (Bjorndahl, et al., 1988). Whereas 5c8 was absent from resting T cells and was expressed on a subset of T cells following activation, in contrast, low level CD69 expression was present on resting T cells and high level CD69 expression was induced by activation on the entire T cell population (FIGS. 10A–L). The kinetics of expression further distinguished 5c8 Ag from CD69 because mAb 5c8 binding was significant 3 h after activation (Bjorndahl, et al., 1988) and persisted for over 24 h (FIGS. 11A–F). The data presented here distinguish the 5c8 Ag from CD69 both by the cellular distribution of their expression and by the kinetics of their up-regulation following activation.

To determine if mRNA or protein synthesis is required for 5c8 Ag expression, T cells were stimulated by PMA and PHA in the presence or absence of Actinomycin D or cycloheximide and the expression of 5c8 and CD69 was compared. The expression of 5c8 was inhibited by either actinomycin D or cycloheximide treatment (FIGS. 10A–L). In contrast, CD69 was up-regulated by activation despite the presence of actinomycin D or cycloheximide (FIGS. 11A–F), as has been reported previously (Bjorndahl, et al., 1988). These data suggested that the expression of the 5c8 antigen after T cell activation depends on transcription of mRNA and de novo protein synthesis.

Characterization of the Subset of T Cells that Express 5c8 Ag After Activation

In order to characterize the subset of T cells that expressed 5c8 Ag after activation, CD4$^+$CD8$^-$ or CD4$^-$CD8$^+$ T cell populations were isolated by anti-CD8 or anti-CD4 mAb treatment, respectively, followed by complement depletion. The CD4$^+$CD8$^-$ or CD4$^-$CD8$^+$ populations were activated with PHA and PMA and studied for 5c8 Ag or CD69 expression by FACS. After activation, 5c8 expression was induced exclusively on CD4$^+$ cells and not on CD8$^+$ cells, despite the fact that CD8$^+$ cells expressed similar levels of CD69 after activation (FIGS. 11A–F). Taken together, these data demonstrated that 5c8 Ag expression is restricted to activated CD4$^+$ cells.

Evaluation of the Role of 5c8 Ag in T Helper Function Mediated by Normal T Cells To evaluate the role of 5c8 Ag in T helper function mediated by normal T cells, the effect of mAb 5c8 was studied on the ability of activated T cells to induce small resting B cells to express surface CD23 molecules. T cells were cultured on surfaces that were coated with anti-CD3 (OKT3) or control, anti-CD4(OKT4) mAbs in the presence of phorbol dibutyrate (PBD) and then fixed with paraformaldehyde. These fixed T cells were studied for B cell activating capacity in the presence o soluble mAb 5c8 or OKT4. The mAb OKT4 was selected as an isotype matched control in these experiments because OKT4 reacts with T cell surface CD4 molecules but does not inhibit T-B interactions (Rogozinksi, et al., 1984). The mAb 5c8, but not OKT4 inhibited the ability of activated T cells to induce 3 cell CD23 expression (see Table 4 below).

TABLE 4

EFFECT OF mAb 5C8 TREATMENT ON B CELL SURFACE CD23 INDUCTION MEDIATED BY PARAFORMALDEHYDE FIXED, ACTIVATED T CELLS.

|  | Media | mAb 5c8 | OKT4 |
|---|---|---|---|
| No T cells | 6.8 | ND | ND |
| Jurkat D1.1 | 93.8 | 9.8 | 96.1 |
| PDB-activated T cells | 29.8 | ND | ND |
| PDB/OKT4-activated T cells | 26.0 | ND | ND |
| PDB/OKT3-activated T cells | 52.7 | 30.4 | 56.1 |

Shown are the percentages of IgM$^-$ B cells that expressed CD23 by 2-color FACS analysis after B cells were cultured alone or in the presence of equal number of Jurkat D1.1 cells or paraformaldehyde fixed T cells that had been stimulated with PBD alone or in the presence of either immobilized anti-CD3 (OKT3) or anti-CD4(OKT4) mAbs, as indicated. The IgG2a mAbs, 5c8 and OKT4 were present at 500 ng/ml which is twice the concentration of mAb 5c8 that inhibited 90% of CD23 induction in a parallel dose response experiment. ND: Not determined.

The effect of mAb 5c8 was next compared to that of OKT4 for its ability to inhibit terminal B cell differentiation driven by normal human T cells. In these experiments, CD4$^-$ T cells were cultured with autologous, column isolated B cells in the presence of PWM and the number of Ig secreting B cell plaque forming colonies (PFCS) was measured by reverse hemolytic plaque assay. The mAb 5c8, but not OKT4, inhibited the CD4$^-$ cell driven PFC response (see Table 5 below). Taken together, these data demonstrated that the 5c8 Ag mediates a contact dependent aspect of the helper effector function of activated CD4$^+$ T cells.

TABLE 5

EFFECT OF mAb 5C8 TREATMENT ON THE INDUCTION OF ANTIBODY FORMING CELLS

| T cells | B cells | PWM | mAb | PFC Exp. 1 | Exp. 2 | Exp. 3 |
|---|---|---|---|---|---|---|
|  | B |  |  | 120 | 240 | 600 |
|  | B | PWM |  | 240 | 600 | 4,800 |
| CD4$^+$ T |  |  |  | 240 | 120 | 180 |
| CD4$^+$ T | B |  |  | 2,580 | 780 | ND |
| CD4$^+$ T |  | PWM |  | 3,840 | 240 | 60 |
| CD4$^+$ T | B | PWM |  | 149,760 | 85,200 | 25,800 |
| CD4$^+$ T | B | PWM | 5c8 | 58,000 | 4,680 | 9,000 |
| CD4$^+$ T | B | PWM | OKT4 | 143,520 | 103,200 | 30,960 |

Shown are the results of three separate experiments on unrelated donors in which CD4$^+$ T cells were cultured in a 0.6:1 ratio with autologous, anti-Ig column isolated B cells in the presence or absence of PWM. The number of plaque forming colonies (PFC) per 10$^6$ B cells was measured by reverse hemolytic plaque assay. The mAbs 5C8 and OKT4 were present at 500 ng/ml except in experiment 1., in which OKT4 was present at 1 ug/ml. ND: Not determined.

Discussion

The Jurkat D1.1 clone is functionally distinct from CD4+ Jurkat and from a variety of other leukemic T cell lines in that it induced B cells from a variety of unrelated subjects to express surface CD23 molecules, a marker of B cell activation and to proliferate and terminally differentiate into ISC in the presence of T-dependent B cell mitogens. The effect of D1.1 on B cell activation required intimate cellular contact and could not be accounted for by secreted factors or by IL-4 in particular. The fact that Jurkat D1.1 was able to induce contact dependent B cell activation and differentiation suggested that Jurkat D1.1 shares surface structure(s) with activated T cells that mediate the contact-dependent, effector phase of help.

The molecular interactions between activated T cells and B cells that mediate the effector phase of T helper function is complex and a poorly understood. To dissect the mechanism of T helper effector function, several studies have measured early events in 3 cell differentiation. First, B cell synthesis of RNA, DNA and enzymes associated with cell cycle progression are induced by activated but no resting T cells (O'Brien, et al., 1988; Grusby, et al., 1991; Noelle, et al. 1991; Noelle, et al., 1990; Zinkernagle, 1976; Sprent, 1978; Sprent, 1978; Jones, et al. 1981; Julius, et al., 1982; Chestnut, et al., 1981). Second, B cell activation, measured by the induction of B cell surface CD23, is induced by activated but not resting T cells (Zinkernagle, 1976). Third, B cell activation and proliferation can be induced by activated T cells that have been fixed with paraformaldehyde (Zinkernacle, 1976; Julius, et al., 1982). Fourth, B cell proliferation is induced by membrane preparations from activated but not resting T cells (Noelle, et al. 1991; Katz, etal., 1973; Brian, 1988). Finally, the ability of activated T cells or activated T cell membranes to induce B cell activation or proliferation is abrogated by protease treatment (Katz, et al., 1973; Jones, et al., 1981). Taken together, these observations are consistent with the idea that T cell activation is associated with the induction of a surface structure that interacts with B cells and provides a contact dependent signal for B cell activation and proliferation. Similar to activated T cells, but unlike other leukemic cell lines, Jurkat D1.1 had the capacity to induce B cell CD23 expression in a manner that depended on cell-cell contact but was independent of lymphokines, Ag specificity or MHC restriction. The induction of B cell surface CD23 expression appears to be an early or intermediate stage in T-directed B cell differentiation into Ig secreting cells that can be driven by the surfaces of fixed, activated T cells (Zinkernagle, 1976; Sprent, 1978). In addition to inducing B cell CD23 expression, Jurkat D1.1 was functionally distinct from CD4+ Jurkat clones in that D1.1 induced terminal B cell differentiation in the presence of PWM. In these respects, Jurkat D1.1 appears to have acquired surface features that it shares with activated T cells and that stimulate B cells.

The nature of the structure on Jurkat D1.1 that accounts for helper function was not identified in the present work. Because CD28 molecules on T cells bind a B cell ligand (Hirohata, et al., 1988), it was of particular interest to compare the expression of CD28 on the helper D1.1 and non-helper B2.7 clones. However, the fact that both Jurkat D1.1 and B2.7 expressed CD28 molecules demonstrated that CD28 alone, could not account for the unique functional properties of Jurkat D1.1. Moreover, in antibody blocking studies using mAb specific for CD2, CD3, CD5, CD38, LFA-1a, LFA-1b and LFA-3; no mAb was able to be identified that inhibited D1.1 mediated B cell activation (not shown). In order to identify the distinctive cell surface features of D1.1 that mediate helper effector function, an attempt was initiated to generate mAbs that react with D1.1 and inhibit D1.1's ability to help B cells.

Although the surface structures that mediate helper function were not identified, the D1.1 system is instructive with respect to the role of CD4 molecules in helper effector function. It is curious that a Jurkat subclone isolated for being CD4− possessed helper function, which is normally associated with the subset of T cells that express CD4 molecules (Sprent, 1978; Jover, et al., 1989). Several lines of Investigation have suggested that CD4 molecules do not play a direct role in helper effector function (Mitchison, 1971; Grusby, etal., 1991; Noelle, et al., 1991; Vitetta, et al., 1989; Noelle, et al., 1990; Katz, et al., 1973; Zinkernagle, 1976). However, the fact that both TCR and CD4 are known to interact with MHC Class II molecules (Ia) (Whalen, et al., 1988) have suggested that ligation of Ia molecules might be a model for helper effector function. In addition, the observation that ligation of Ia molecules on B cells can signal B cells has further supported this model (Pollok, et al., 1991; Bartlett, et al., 1990; Martinez, et al., 1981). The fact that Jurkat D1.1 had helper function but was CD4− strongly suggests that CD4 molecules are not required for the effector phase of helper function. On the contrary, the finding that a CD4− clone of Jurkat has acquired helper function suggests that CD4 molecules might inhibit the helper effector function of CD4+ Jurkat cells. In order to directly determine the relationship between the lack of CD4 molecules on Jurkat D1.1 and its unique helper function, stable CD4+ transfectants of D1.1 were generated by electroporation of CD4 cDNA constructs driven by heterologous promoters. The expression of CD4 did not inhibit the ability of D1.1 transfectants to activate B cells suggesting that D1.1's helper activity is mediated by surface features other than the lack of CD4 molecules.

Recently it has been shown in the murine system that membrane preparations derived from activated, but not resting T lymphocytes are sufficient to induce B cell proliferation but not Ig secretion (Noelle, et al., 1991; Katz, et al., 1973; Brian, 1988). The relevance of these studies to the D1.1 system is presently unclear, but it will be of interest to determine if membranes isolated from D1.1 cells induce B cell CD23 expression, proliferation and terminal differentiation. In any case, it is likely that Jurkat D1.1 will be useful for the identification and characterization of surface molecules important in mediating contact dependent helper function.

A functionally unique Jurkat leukemic line (D1.1) with constitutive, contact dependent helper function was utilized to generate a murine mAb, designated 5c8, that inhibited D1.1 induced B cell activation. The mAb 5c8 recognized a unique protein species on D1.1 cells that was not disulfide linked and migrated at 30 kDa MW on SDS/PAGE. On normal lymphoid cells, the expression of 5c8 Ag was restricted to a subset of T lymphocytes after activation. The activation induced expression of 5c8 Ag on T cells required transcription of mRNA and de novo protein synthesis. The 5c8 Ag was found to be transiently expressed on activated T cells with peak expression at 6 h and loss of expression by 24 h. The expression of 5c8 Ag was restricted exclusively to activated CD4+ T cells. In functional studies on normal T cells, the mAb 5c8 inhibited the ability of fixed, activated T cells to induce B cell CD23 expression. In addition, mAb 5cB inhibited the ability of normal T cells to direct B cell differentiation. Taken together, these data demonstrate that the 5c8 Ag is a novel activation-induced surface protein expressed exclusively on activated CD4+ T cells that is involved in mediating a contact dependent element of T helper function.

The tissue distribution, kinetics of expression, metabolic requirements for induction and biochemistry of the 5c6 Ag distinguished the 5c8 Ag from other known surface proteins induced by T cell activation. First, all other known T cell activation markers (e.g. CD69, CD25, Ia) are expressed by both CD4+ and CD8+ T cells whereas the 5c8 Ag is expressed exclusively by CD4+ T cells. Second, the kinetics of 5c8 Ag expression following T cell activation were distinct from that of other T cell activation molecules. Whereas 5c8 Ag was maximally expressed 6 h after activation and absent 24 h after activation, CD25 (Doech, et al., 1980), Ia (Rabin, et al., 1985) and the 32 kD form of CD27 are induced 18 h or more after activation. In addition, CD69 is expressed more rapidly than 5c8 Ag and (unlike 5c8 Ag) persists for over 24 h. Third, 5c8 Ag was distinguished from CD69 by the metabolic requirements of their induction, because induction of 5c8 Ag but not CD69 expression depended on mRNA transcription and protein synthesis. Fourth, the 5c8 Ag was a 30 kD, non-disulfide linked species. In contrast, the early activation molecule, CD69 is a 28/32 kD disulfide linked heterodimer (Bjorndahl, et al., 1988). Taken together, these data suggest that the 5c8 Ag was distinct from other known T cell activation molecules.

The 5c8 Ag was also distinguished from other cell surface molecules that are known to play roles in T-B interactions by several aspects of their tissue distribution and biochemistry. First, 5c8 Ag was induced by T cell activation but was not expressed on resting cells In contrast, CD4, CD2, CD5, CD28, LFA-1, ICAM-1, CD45RO and 6C2, which interact with B cell surface ligands (Doyle, et al., 1987; Van de Velde, 1991; Tohma, et al., 1991; Sanders, et al., 1991; Linsley, et al., 1990; Stamenkovic, et al., 1991; Rothlein, et al., 1986; Tonimoto, et al., 1991) are expressed on resting T cells (Rothlein, et al., 1986; Tonimoto, et al., 1991; Sanchez Madrid, et al., 1982; Smith, et al., 1985; Yamada, et al., 1985). Second, the specific expression of 5c8 Ag on activated T lymphocytes and not on B cells, monocytes or the panel of cell lines (Table 1.) distinguished 5c8 Ag from ICAM-1, CD4, CD5, LFA-1, CD2 and 6C2 molecules which are also expressed on either monocytes, B cells or certain of the cell lines (not shown). Third, the expression of 5c8 Ag was restricted to CD4+ T cells whereas: CD2, CD5, CD28, LFA-1, ICAM-1, CD45RO and 6C2 are expressed on CD8+ as well as CD4+ cells (Rothlein, et al., 1986; Tonimoto, et al., 1991; Sanchez Madrid, et al., 1982; Smith, et al., 1986; Yamada, et al., 1985). Fourth, the 30 kD protein precipitated by mAb 5c8 is unlike any of these other proteins (Rothlein, et al., 1986; Tonimoto, et al., 1991; Sanchez Madrid, et al., 1982; Smith, et al., 1986; Yamada, et al., 1985). Finally, 5c8 Ag was distinct from these other molecules because the mAb 5c8 was identified by its ability to inhibit the helper effector function mediated by Jurkat D1.1.

Because the mAb 5c8 inhibits the contact dependent helper effects of Jurkat D1.1 and faxed, activated T lymphocytes, it is likely that the 5c8 Ag mediates a B cell activating function by interacing with a ligand (or "counter-receptor") on the surfaces of B cells. The interaction of 5c8 Ag with a B cell counter receptor may mediate helper function either by providing additional adhesive forces to T-B pairs, transducing a stimulatory signal to B cell cytoplasms or by a combination of these mechanisms. Regardless of the precise mechanism, the transient expression of 5c8 Ag may provide a molecular solution to limiting non-specific B cell activation. The transient expression of 5c8 Ag in the localized milieu of antigen specific cognate T-B pairs may channel the antigen/MHC unrestricted activating function of 5c8 Ag to appropriate B cell targets. The kinetics of expression and down-regulation of 5c8 Ag are shared by the endothelial cell, activation induced, cell surface mediator of leukocyte and lymphocyte binding, ELAM-1 (Bevilacqua, et al., 1987). This similarity might indicate that the strategy of utilizing transient expression to effect localized intercellular interactions may be shared by 5c8 Ag, ELAM-1 and potentially other, yet uncharacterized, surface molecules that transmit potent signals to other cells by direct contact.

The CD4 molecule identifies the population of T cells that contains precursors of T cells with helper function (Reinherz, et al., 1979). However, the CD4+ subset is functionally heterogeneous and contains cytotoxic and suppressor cells in addition to helper cells (Krensky, et al., 1982; Thomas, et al., 1981). The fact that 5c8 Ag is involved in helper function suggests that 5c8 Ag may correlate more closely with the helper phenotype than CD4 expression. The heterogeneous distribution of 5c8 expression on activated CD4+ cells suggests that functional subsets of CD4+ T cells might be distinguished by their level of 5c8 expression. For example, it will be of interest to determine the functional potential of 5c8⁻ and 5c8+ CD4+ T cells with respect to helper or cytotoxic activity.

T cell helper effector function is a complex process resulting in B cell responsiveness (Krusemeier, et al., 1988; Hodgkin, et al., 1990; Noelle, et al., 1991; Kubota, et al., 1991), regulation of isotype switching (Tesch, et al., 1984) and somatic hypermutation (Weigert, et al., 1970). The fact that T cells interact with B cells by a number of cell-cell interactions as well as by secreting various lymphokines suggests that individual signals or certain combinations of signals may regulate specific aspects of B cell differentiation. The fact that the mAb 5c8 inhibits a contact dependent aspect of T cell helper function provides a means of further dissecting the processes by which CD4+ T cells regulate the humoral immune response.

Second Series of Experiments
Molecular Interactions Mediating T-B Lymphocyte Collaboration in Human Hymphoid Follicles In a process termed T helper function CD4⁺ T lymphocytes select and induce the differentiation of antigen specific B cells that mediate the humoral (antibody-mediated) immune response (Mitchell, et al.; 1968; Mitchison, 1971; White, et al; 1978; Reinherz, et al., 1979; Janeway, et al., 1988; Rehemtulla, et al., 1991; Grusby, et al. 1991). Physiologic T-B interactions occur in lymphoid follicles, but a variety of in vitro systems have allowed a mechanistic dissection of T helper signals. Although the inductive phase of help is antigen and MHC restricted, the effector phase is non-specific and mediated by both lymphokines and contact dependent signals (Martinez, et al., 1981; Anderson, et al., 1980; Clement, et al., 1984; Crow, et al., 1986; Brian, 1988; Hirohata, et al., 1988; Noelle, et al., 1989; Whalen, et al. 1988).

Progress in the elucidation of contact dependent signals was achieved by the recent identification of a functionally unique subclone of the Jurkat T cell leukemia line, D1.1, that constitutively activates resting peripheral B cells (Yellin, 1991). The D1.1 clone has previously been shown to induce resting B cells to express surface CD23 molecules, drive B cells to proliferate, and induce B cells to differentiate into Ab forming cells (Yellin, 1991). The B cell activating capacity of D1.1 was localized to the cell surface, because paraformaldehyde fixed D1.1 retained the capacity to activate B cells, but D1.1 supernatants were inactive (Yellin, 1991). Together, these data suggested that D1.1 shared surface structures with activated T cells that mediate contact dependent helper function.

In the first series of experiments, one such structure termed 5c8 Ag was identified by screening hybridomas for mAbs which react specifically with D1.1 and which inhibit the functional activation of B cells by D1.1 (Lederman, et al., 1992). The mAb 5c8 identified a novel 30 kDa structure that was expressed on activated CD4+ T cells, but not CD8+ T cells, B cells or monocytes (Lederman, et al., 1992). The kinetics of cell surface expression of 5c8 Ag after PHA and PMA stimulation are relatively unique in that maximal expression occurs after 6 h, but is followed by down-regulation that results in baseline (no) expression by 24 h (Lederman, et al., 1992). In Functional assays, the mAb 5c8 inhibits the ability of normal CD4+ T cells to drive B cell differentiation into antibody forming cells (Lederman, et al., 1992). Taken together, these data demonstrate that the 5c8 Ag is one component of the surface structures on CD4+ T cells that mediate contact dependent helper function and therefore the 5c8 Ag is now renamed as "T cell-B cell activating molecule" (T-BAM).

Although T-BAM, is one of the T cell molecules that induces contact dependent helper function in vitro, little is known concerning its ligand or "counter-receptor" on B cells, or what the roles of other T and 3 cell molecules are in mediating contact dependent helper function in lymphoid tissues in vivo. Several interesting B cell surface molecules have been described that may play roles in receiving contact dependent signals in lymphoid tissue. Among these are the CD40 molecule, CR2 molecule and adhesion molecules. The CD40 molecule on human B cell surfaces has interesting signalling functions relevant to lymph node B cell differentiation (Clark, et al., 1986; Clark, et al., 1988; Ledbetter, et al., 1987; Ledbetter, et al., 1986) because anti-CD40 (mAb G28-5 (Clark, et al., 1986)) prevents programmed, germinal center B cell death (apoptosis) (Lim, et al., 1989) and has been shown to induce proliferation, differentiation and long term growth of human B cells (Banchereau, et al., 1991a; Banchereau, et al., 1991b). CR2 is a complement receptor on B cells that can deliver mitogenic signals to B cells after antibody triggering or in its role as cell surface receptor for Epstein Barr Virus (Nemerow, et al., 1985; Carter, 1988). Finally, the adhesion receptors LFA1, LFA3 and ICAM-1 are known to play roles in the adhesive interactions of many cellular interactions and mAbs that react with these structures inhibit T-dependent B cell processes (Tohma, et al., 1991a; Tohma, et al., 1991b). However, precise roles for these molecules in helper interactions have not been defined.

In this second series of experiments, these findings were extended in three ways. First, a B cell lymphoma clone RAMOS 266 (Siegel, et al., 1990) was identified that responds to D1.1 cell contact in a manner that is inhibited by anti-T-BAM (mAb 5c8). Second, a surface structure on B cells (CD40) was identified that participates with T-BAM in mediating contact dependent T-B activation. Third, T-BAM is shown to be expressed by T cells predominantly in the mantle and centrocytic zones of lymph nodes in vivo which are the anatomic sites of T cell interactions with CD40 expressing B cells.

Materials and Methods
Cell Lines

The Jurkat clones D1.1 and B2.7 have been described (Yellin, et al., 1991; Lederman, et al., 1992). The RAMOS 266,4CN 3F10 (RAMOS 266) clone (Siegel, et al., 1990) was the kind gift of Dr. Jay P. Siegel of the Center for Biologics Evaluation and Research, Food and Drug Administration (Bethesda, Md.). L cells expressing human FcRgII (CD32) (gift of Dr. Jacques Banchereau, Schering-Plough, (Dardilly Cedex, France) (24) or L cells expressing mouse Ia, (gift of Dr. Ned Braunstein, Columbia University).

Monoclonal Antibodies

The mAb 5c8 (IgG2a) has been described (Lederman, et al., 1992). The following mAbs were produced by hybridomas available from the American Type Culture Collection (Manassas, Va.); OKT4(anti-CD4), OKT8(anti-CD8), OKT3 (anti-CD3), W6/32(anti-MHC Class I), THB-5 (anti-CR2(CD21)), TS1/22.1.13 (anti-LFA1a(CD11a)), TS1/18.1.2.11.4 (anti-LFA1b (CD18)), and TS2/9.1.4.3 (anti-LFA3(CD58)). These mAbs were either used at saturating concentrations of hybridoma supernatants or dilutions of ascites, or purified from ascites fluid on protein A (Biorad, Rockville Center, N.Y.) or protein G columns (Pharmacia®, Upsula, Sweden). Anti-LFA3 (7A6) was a gift from Dr. Vicki Sato, Biogen (Cambridge, Mass.). Anti-CD23-PE, leu16 (anti-CD20), and leuM5 (IgG2b anti-CD11c) mAbs were purchased from Becton Dickinson (Mountainview, Calif.). The mAb G28-5 (19) was the gift of Dr. Edward A. Clark, University of Washington (Seattle, Wash.). The mAb RR1/1.1.1 (anti-ICAM-1(CD54)) was the gift of Dr. Peter Lipsky, University of Texas Southwestern Medical Center (Dallas, Tex.). The anti-CD40 mAb B-B20 (IgG1) was purchased from Biosource International (Camarillo, Calif.). The mAb 32.2 (anti-FcRgII(CD32)) was purchased from Medarex, West Lebanon, N.H. FITC labeled anti-IgM was purchased from Tago (Burlingame, Calif.). The unrelated, isotype-matched control mAbs UPC-10 (IgG2a) and MOPC141 (IgG2b) were purchased from SIGMA® St. Louis, Mo.). Anti-IL-4 and anti-SM-CSF were purchased from Genzyme (Cambridge, Mass.).

Cytofluorographic Analysis

Approximately $10^5$ cells were incubated with saturating concentrations of the indicated mAbs for 45 min at 4° C. in the presence of 80 mg/ml heat-aggregated human IgG (International Enzyme, Fallbrook, Calif.) Cells were washed to remove unbound mAb before incubation with F(ab)$_2$ goat anti-mouse Ig secondary antibody coupled to fluorescein (Cappel, Cochranville, Pa.). For two color analysis, cells were reacted with the indicated directly coupled FITC or Phycoerythrin (PE) conjugated mAb for 45 min at 4° C. in the presence of aggregated human IgG. Prior to analysis, cells were washed and resuspended in PBS. Fluorescence intensity was measured on a FACSCAN Cytofluorograph (Becton-Dickinson, Mountainview, Calif.). In experiments involving co-culture of B cells with Jurkat clones, the Jurkat cells were excluded from the analysis of B cell fluorescence by gating on the distinct population or cells with low forward and side light scatter.

Lymphokines rIL-4 was the gift of Dr. Robert Coffman, DNAX and rIL-2 was from Hoffman-LaRoche.

Isolation of Cell Populations

Peripheral blood lymphocytes were obtained from the freshly drawn blood of healthy volunteers by centrifugation on ficoll-hypaque (Sigma, St. Louis, Mo.). Spleen B cells were similarly obtained from fresh biopsy specimens from organ donors (provided by Dr. Mark Barr, Department of Surgery, Columbia University.) Tonsil B cells were obtained from fresh surgical specimens after tonsillectomy (provided by Dr. Joseph Hadad, Department of ENT, Columbia University). The lymphoid tissue B cells were obtained by mincing tissue specimens and passing them through a metal screen followed by ficoll-hypaque centrifugation.

T cells were positively selected with neuraminidase treated sheep erythrocytes. B cells were derived from the population of cells that did not pellet through ficoll-hypaque after two rounds of rosetting with neuraminidase treated sheep erythrocytes.

B cells were further purified by density centrifugation. E-cells were cultured overnight in polystyrene flasks (37° C., 5% $CO_2$) to deplete macrophages by adherence. These non-T cell, non-macrophage cells were fractionated into high and low density fractions in a discontinuous 30%/50%/100% percoll gradient by centrifugation at 2300 rpm for 12 min. High-density cells were obtained from the 50/100% interface and low-density cells from the 30/50% interface (Crow, et al., 1985). The high density (resting) cells from peripheral blood were typically 60–90% CD20-, 55–90% IgM,+ and <5% CD3+ and <5% CD23+ (background). The high density B cells from tonsil and spleen were >95% CD20+

L cell Culture Experiments

L cells expressing human FcRgII (CD32) or mouse Ia were grown to near confluence in DMEM 10% FCS in 12 well plates (Costar, Cambridge, Mass.). The monolayer was washed once with media and $2 \times 10^6$ B cells in 1 ml IMDM 10% FCS were added to the monolayer before the addition of control media or 2 mg of mAbs G28-5, B-B20 or control mAbs. After 18 hours of culture, the B cells were collected by pipetting with moderate agitation, washed once and analyzed for CD23 expression by FACS as described above.

Assays of B Cell Activation and Differentiation

In experiments measuring the induction of B cell surface CD23 expression, $1–2 \times 10^5$ high density B cells or RAMOS 266 cells were added to an equal number of Jurkat cells in 200 ml of IMDM 10% FCS in round bottom microtiter wells (Nunc) and assayed for CD23 expression after 18–24 h.

Human Tissue Specimens

Biopsy specimens were collected during the course of standard diagnostic procedures or at autopsy and promptly delivered to the laboratory. Representative portions of each tissue specimen were snap-frozen in optimal cutting temperature (OCT compound, Miles, Elkhart, Id.) on circular cork disks in a mixture of isopentane and dry ice and stored for varying periods at $-70°$ C. Representative portions of each specimen were routinely fixed in buffered formalin, B5, or Bouin's, embedded in paraffin, and hematoxylin and eosin (H&E) stained sections were prepared.

Representative portions of multiple benign tissue specimens were collected from random patients during the course of routine diagnosis and were examined by immunohistochemistry for mAb 5c8 binding. These specimens included: esophagus 2, stomach 2, small intestine 3, colon 6, pancreas 2, liver 3, kidney 3, uterus 3, ovary 2, testis 2, prostate 1, lung 4, heart 2, skin 3, breast 2, brain 2, tonsil 14, thymus 7, lymph node 4, spleen 10 and appendix 5.

Immunohistochemical Staining

Serial four micron frozen sections were cut from cryopreserved tissue blocks, fixed and stained as previously described in detail (Inghirami, et al., 1990). Briefly, sections were serially incubated with appropriately titered mAbs, with F(ab')$_2$ goat anti-mouse IgG (Fc gamma specific, 1:200, Organon Teknika, Malvern, Pa.), and alkaline phosphatase-anti-alkaline-phosphatase complex (APAAP, Dako, Santa Barbara, Calif.), and then developed with New Fuschin and B-napthol-AS-Bi-phosphate as a substrate. Alternatively, sections were incubated with primary mAb or an isotype-matched unrelated mAb, washed three times, and incubated with biotinylated horse anti-mouse IgG (Vector, San Diego, Calif.). Peroxidase conjugated avidin-biotin complex was applied and developed with diaminobenzidine (DAB) and in some cases amplified with nickel chloride. Two color immunohistochemical staining was also performed on cryostat tissue sections as previously described (Inghirami, et al., 1991). Briefly, sections were first stained with a single mAb (mAb 5c8, or an isotype-matched unrelated mAb (UPC-10, IgG$_{2a}$) using an ABC technique (Vector) and developed with DAB. Sections were then incubated with mAb (Leu M5, CD11c) or an isotype-matched unrelated mAb, washed three times, and incubated with APAAP complex and then developed as described above.

Results

Identification of a B Lymphoma Cell Line That Responds to D1.1 Triggering

We previously showed that the 5c8 Ag (T-BAM) is a protein on the surface of activated CD4+ T cells involved in contact dependent helper function (Lederman, et al., 1992). In order to further dissect this process, we sought to identify a system of homogeneous, cloned lymphoma cell lines to potentiate a molecular analysis of the roles of T-BAM and other molecules. To this end, we utilized the T-BAM expressing lymphoma cell line D1.1 to identify a B cell lymphoma that responded to D1.1 contact by upregulating CD23. A candidate cell line was the RAMOS 266 clone that expresses low levels of CD23, but is induced by IL-4 to express high levels of CD23 (Siegel, et al., 1990).

Figure 12:
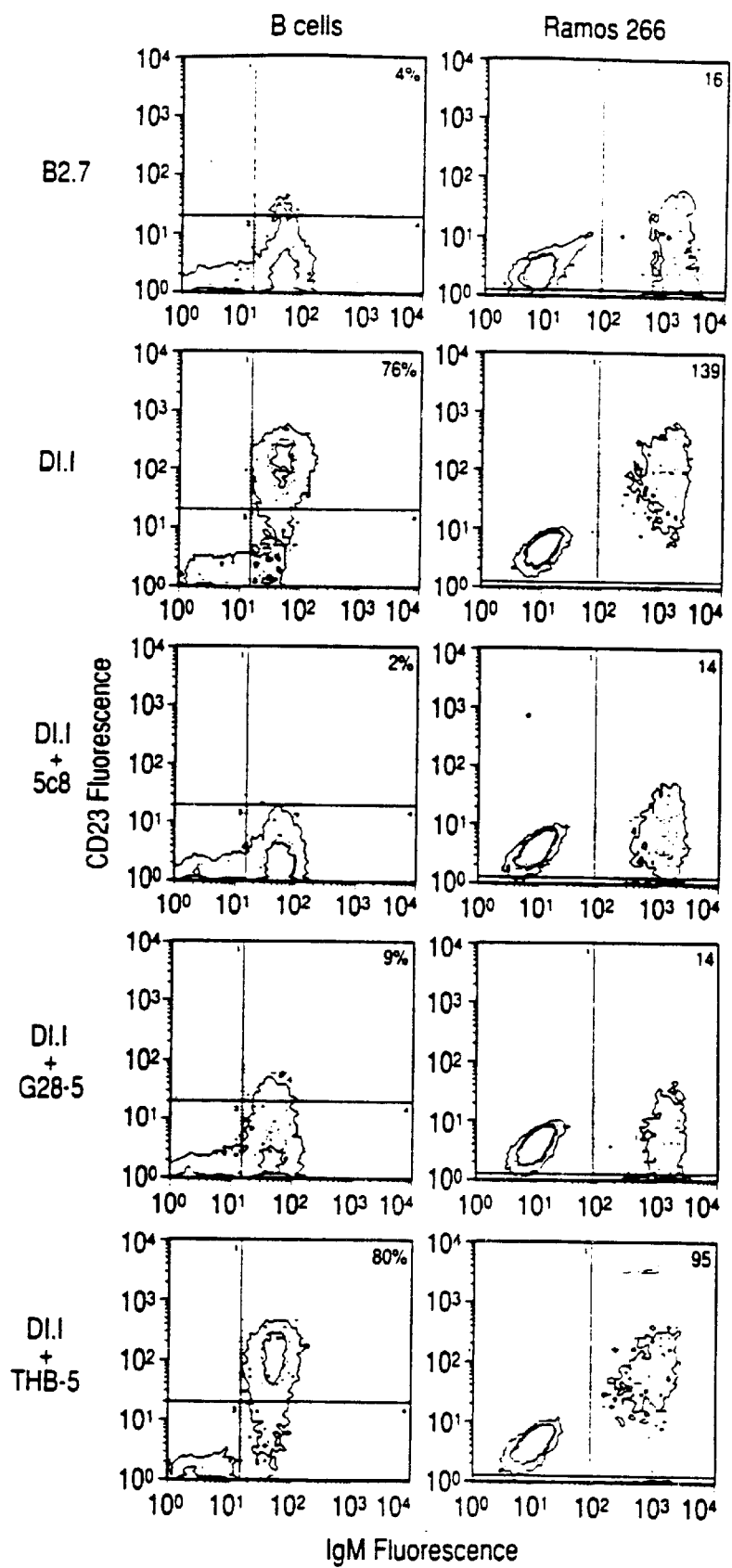
FIG. 12. D1.1 induces surface CD23 expression on B cells or RAMOS 266 in a manner that is inhibited by mAb 5c8 (anti-T-BAM) or mAb G28-5 (anti-CD40). Shown are 2-color FACS histograms of anti-IgM FITC on the x axis and anti-CD23 PE on the y axis of 3 cells (left column) or RAMOS 266 (right column) after culture with Jurkat clones D1.1 or B2.7 as indicated. The number in the upper right hand corner refers to the percentage of IgM+ B cells expressing sur ace CD23 in experiments involving B cells, or in RAMOS 266 experiments, the median fluorescence intensity of CD23 on RAMOS 266.

To ask if RAMOS 266 responds to D1.1 cell mediated contact we cultured RAMOS 266 cells with D1.1 cells and measured the cell surface expression of CD23 on RAMOS 266 by two color FACS analysis (FIG. 12). In these experiments, peripheral B cells were cultured with D1.1 as a positive control because B cells are known to respond to D1.1 contact by increasing surface CD23 (FIG. 12). As a negative control, RAMOS 266 or peripheral B cells were cultured with the B2.7 clone of Jurkat which does not express T-BAM and does not activate B cells (Lederman, et al., 1992). As expected, Jurkat D1.1 but not Jurkat B2.7 induced peripheral B cells to express surface CD23 molecules after 18 h in culture (FIG. 12). Importantly, similar to its effect on peripheral B cells, D1.1 cells, but not B2.7 cells, induced RAMOS 266 to express CD23 after 18 h of co-culture (FIG. 12). An apparent difference in the responses between RAMOS 266 and peripheral B cells was that the entire population of RAMOS 266 upregulated CD23 as a homogeneous peak, whereas peripheral B cells typically had a distinct responding population (typically 80% expressed CD23) and a distinct non-responding population (typically 20% were CD23-). Because of this distinction, it was necessary to quantitate the RAMOS 266 response as the median fluorescence intensity (MFI) of the single peak of CD23 expression and to quantitate the peripheral B cell response as the percentage of responding cells (FIG. 12). Dose response experiments, in which graded numbers of D1.1 cells were added to constant numbers of RAMOS 266 or B cells, validated these measurements because decreasing numbers of D1.1 cells resulted in decreased RAMOS 266 MFI (not shown) and decreased percent CD23+ B cells (Yellin, et al., 1991), respectively. These data demonstrate that RAMOS 266 responds to D1.1 coculture in a manner that appears to be analogous to the response of peripheral B cells.

To determine whether the D1.1 effect on RAMOS is dependent on T-BAM, the effect of the anti-T-BAM mAb 5c8 on D1.1 mediated activation was then studied. In these experiments, mAb 5c8 or an isotype control mAb were added to cultures of RAMOS 266 or peripheral B cells with D1.1 cells (FIG. 12). Similar to the known effect of mAb 5c8 on inhibiting D1.1 activation of peripheral B cells, the mAb 5c8 inhibited D1.1 activation of RAMOS 266 (FIG. 12). In contrast, the isotype control mAbs did not inhibit the D1.1 effect. Taken together, these data demonstrate that a B lymphoma cell line (RAMOS 266) possesses the cellular machinery to express CD23 after activation by D1.1 and that the D1.1-RAMOS 266 interaction is inhibitable by mAb 5c8. Further, these data suggest that the D1.1-RAMOS 266 interaction may be a valid model system to further dissect contact dependent T-B signalling in homogeneous lymphoma cell lines.

Figure 13:
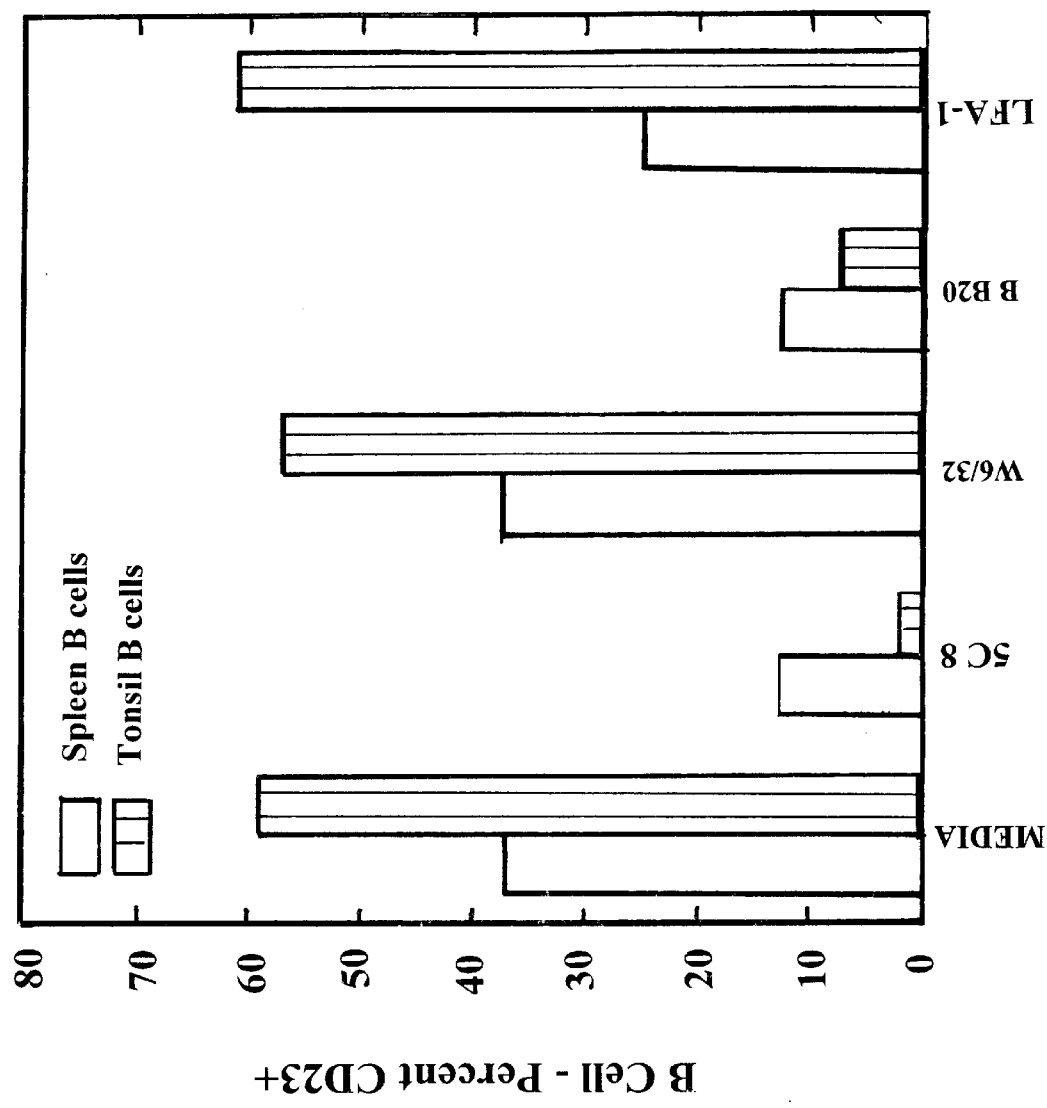
FIG. 13. Effect of D1.1 on tonsil B cells. Shown are the percentage of IgM+ B cells expressing CD23 by 2-color FACS analyses after D1.1 or B2.7 cells were cultured with tonsil B cells for 18 h in the presence of mAb 5c8 (IgG2a anti-T-BAM), W6/32 (IgG2a anti-Class I MHC), anti-LFA1a (IgG1) and B-B20 (IgG1 anti-CD40).

Because, ultimately, our interest in these studies was to define the role of T-BAM in lymphoid B cell differentiation, we next studied the D1.1 effect on B cells isolated from lymphoid organs. Therefore, in experiments similar to those described above, we cultured B cells isolated from lymphoid organs with D1.1 cells in the presence and absence of mAB 5c8 and control antibodies. Similar to the effect of D1.1 on peripheral 3 cells and on the lymphoma clone (RAMOS 266), we found that D1.1 cells activate B cells from either tonsil (FIG. 13) or spleen (not shown) to express CD23 molecules. Further, the effect of D1.1 cells on lymphoid B cells was inhibited by mAb 5c8 and not by control mAbs (FIG. 13). These data demonstrate that the molecular interactions between D1.1 cells and RAMOS 266 parallels those between T and B cells in lymphoid organs.

Figure 14A:
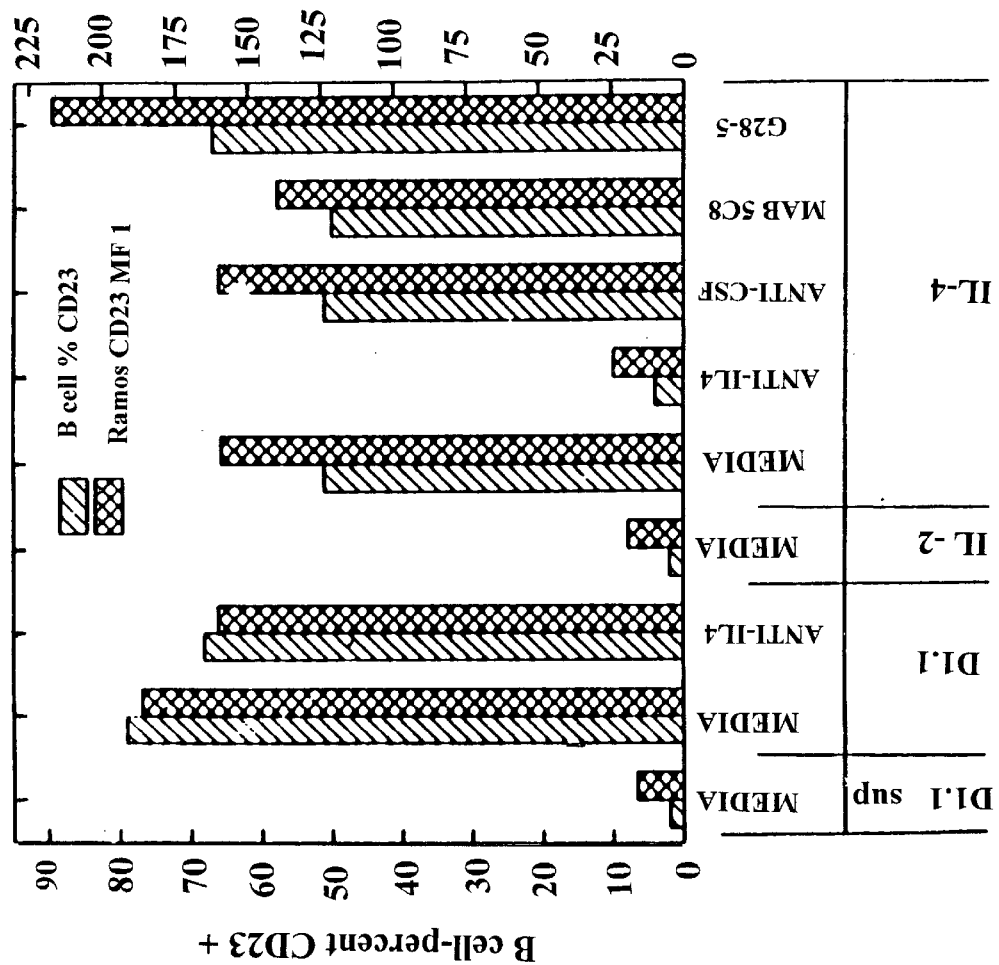
FIGS. 14A–B. Roles of T-BAM and CD40 in D1.1-B cell activation. Shown are bar charts depicting 2-color FACS data of the percentage of IgM+ B cells expressing surface CD23 (left y axis, striped bars) or the CD23 median fluorescence intensity (right y axis, cross-hatched bars) of RAMOS 266 after 18 h in culture with Jurkat clones D1.1 or B2.7, or in the presence of lymphokines as indicated.

It was previously demonstrated that the potentiating effects of D1.1 on B cells is independent of secreted factors. To determine how D1.1 cells activate RAMOS 266, the next series of experiments studied the D1.1 effect on RAMOS with respect to lymphokine release and particularly the role of IL-4. In these experiments, RAMOS 266 was cultured with either D1.1 supernatants, D1.1 cells, rIL-2 or rIL-4 and the level of surface CD23 expression was measured by FACS after 18 h. As shown in FIG. 14a., D1.1 cells or IL-4 induced CD23 on RAMOS 266 or peripheral B cells. In contrast, D1.1 supernatant or rIL-2 had no effect (FIG. 14a.). In addition, the effect of rIL-4 but not that of D1.1 was inhibited by anti-IL4 (FIG. 14a.). Finally, mAb 5c8 did not inhibit the rIL-4 effect (FIG. 14a.). Taken together, these data suggest that the effect of D1.1 on RAMOS 266 is independent of lymphokine release and confirm previous observations that D1.1does not secrete bioactive IL-4 (FIG. 14a.).

Identification of B Cell Surface Molecules Involved in T-BAM Triggering

The D1.1-RAMOS 266 system was then exploited to identify B cell surface molecules that play roles in conract-dependent T-B interactions. Of the characterized B cell surface molecules, we considered CD40, CR2, and adhesion receptors as candidates for roles in contact dependent signalling because of their known roles in B cell activation and particularly with respect to contact dependent interactions (Banchereau, et al., 1991a; Nemerow, et al., 1985; Carter, et al., 1988; Tohma, et al., 1991a; Tohma, et al., 1991b; Emilie, et al., 1988; Sen, et al., 1992). Therefore, we studied the effect of mAbs to these B cell molecules on D1.1 mediated activation of RAMOS 266 and peripheral B cells.

Figure 14B:
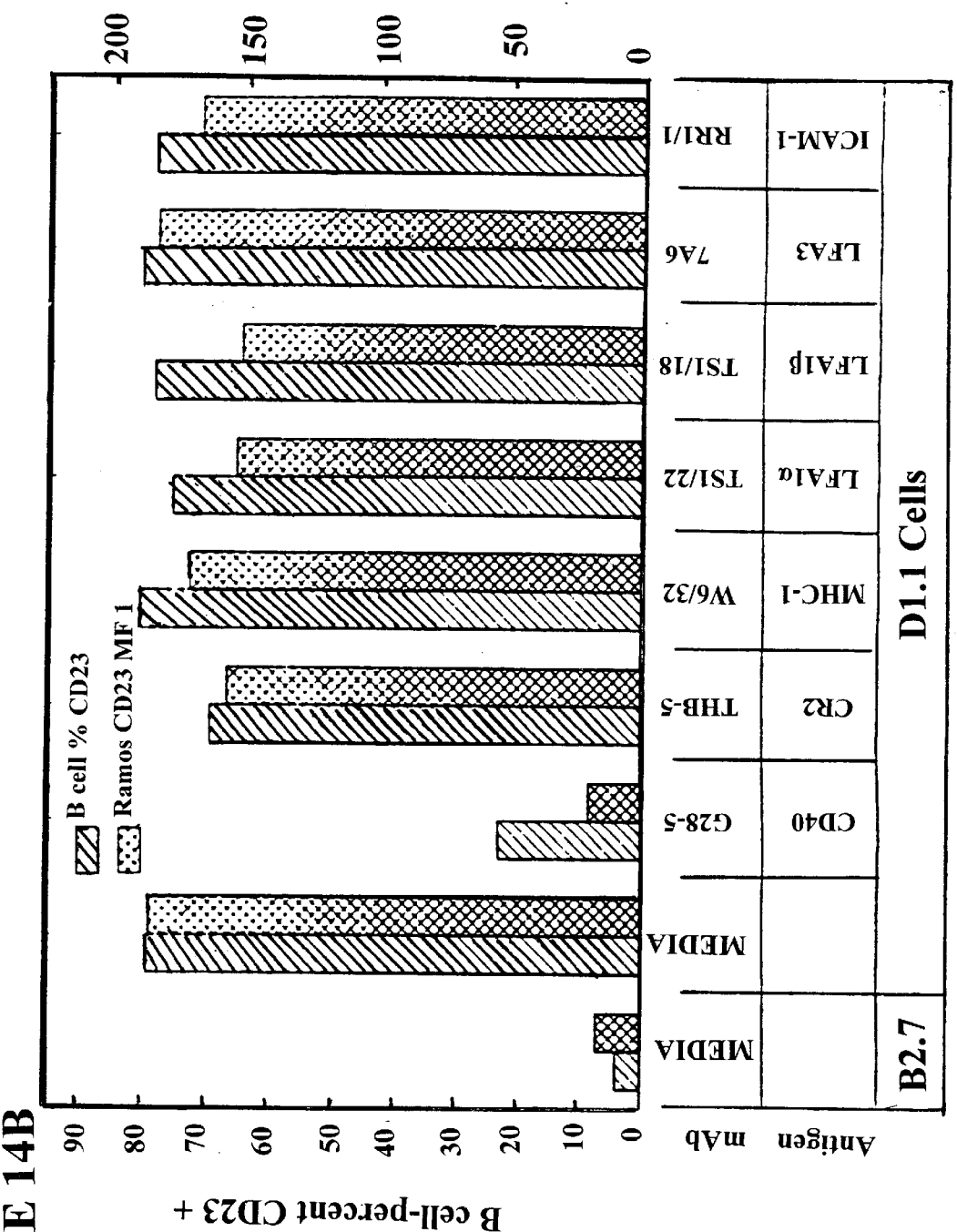
Figure 15:
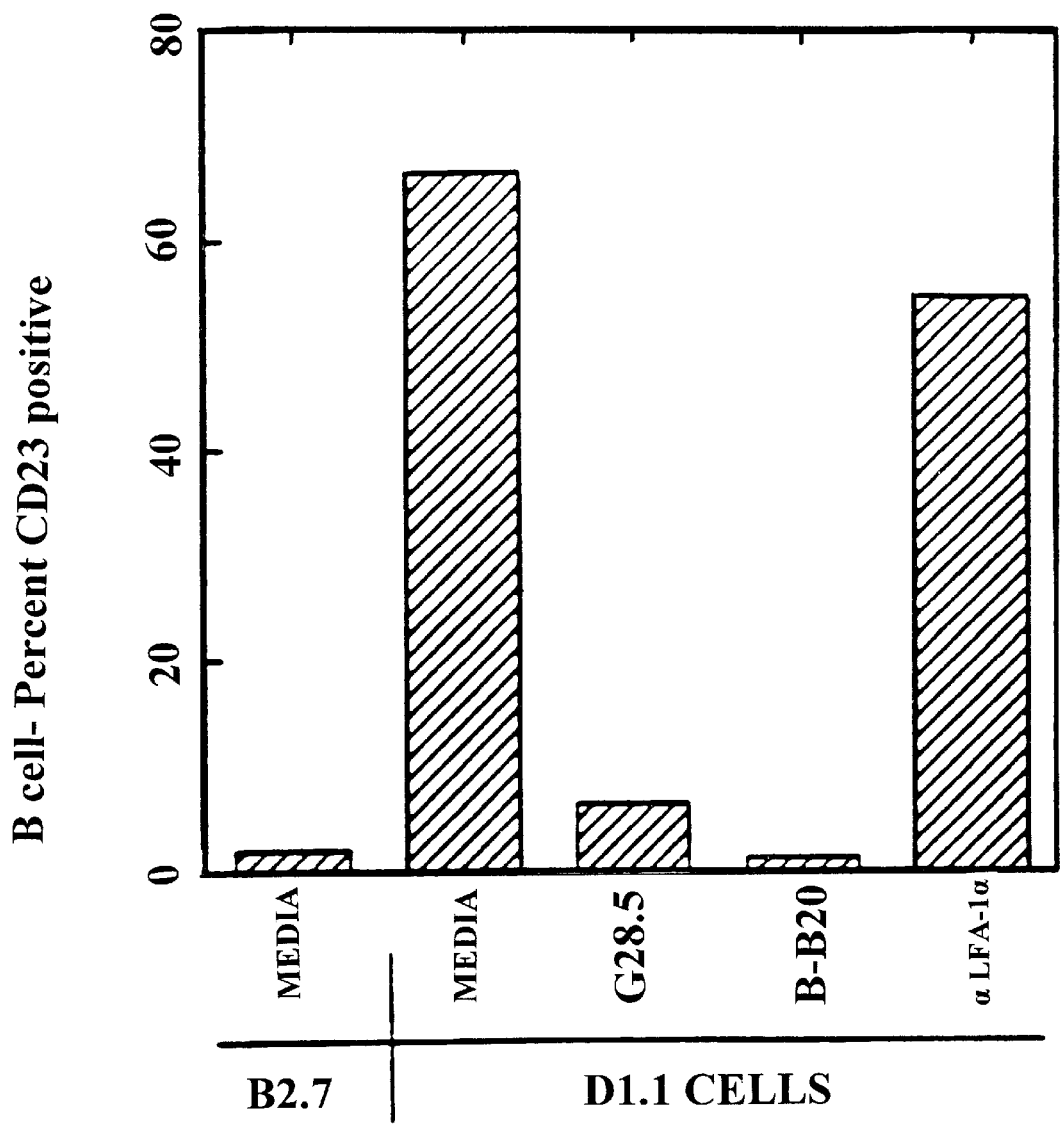
FIG. 15. Effect of anti-CD40 mAbs on D1.1 activation of peripheral B cells. Shown are the results of 2-color FACS analysis of IgM+ B cells cultured with D1.1 cells in the presence of the indicated mAbs for 18 h.

In these experiments, D1.1 cells were cultured with RAMOS 266 or peripheral B cells in the presence of a panel of mAbs that react with B cell surface molecules and the expression of RAMOS 266 or B cell CD23 was measured after 18 h. The mAb 5c8 served as a positive control for inhibition in these experiments (FIG. 12). Importantly, the anti-CD40 mAb, G28-5 (Clark, et al., 1986), inhibited D1.1 mediated RAMOS 266 or B cell activation (FIGS. 12, 14b) whereas mAbs to CR2, LFA-1, LFA-3 and ICAM-1 had little effect (FIGS. 12, 14b). In addition to G28-5 (IgG1), the anti-CD40 mAb B-B20 (IgG1) also inhibited the D1.1 effect (FIG. 15). In these experiments, the anti-LFA1a mAb TS1/22 (IgG1), which reacts with the surface of both B cells and RAMOS 266, served as an isotype matched negative control (FIGS. 14b, 15). In similar experiments, we found that anti-CD40 inhibited the D1.1 effect on B cells isolated from lymphoid organs (FIG. 13). Taken together, these data show that anti-CD40 mAbs are unique among the anti-B cell antibodies tested, in that they inhibit D1.1 mediated upregulation of B cell CD23.

It was somewhat of a surprise that anti-CD40 mAbs inhibit CD23 expression because anti-CD40 mAbs are known to augment rIL4 induced B cell CD23 expression (Clark, et al., 1989). This issue was therefore readdressed and found that in contrast to the inhibitory effect of G28-5 on D1.1 induced CD23 expression, G28-5 augments the rIL-4 induced upregulation of CD23 on both B cells and the RAMOS 266 indicator clone (FIG. 14a). Taken together, these data demonstrate that while anti-CD40 mAbs inhibit the D1.1 effect on B cells, the effect of these mAbs on B cells is not a general inhibition of activation because anti-CD40 potentiates the rIL-4 effect.

Figure 16A:
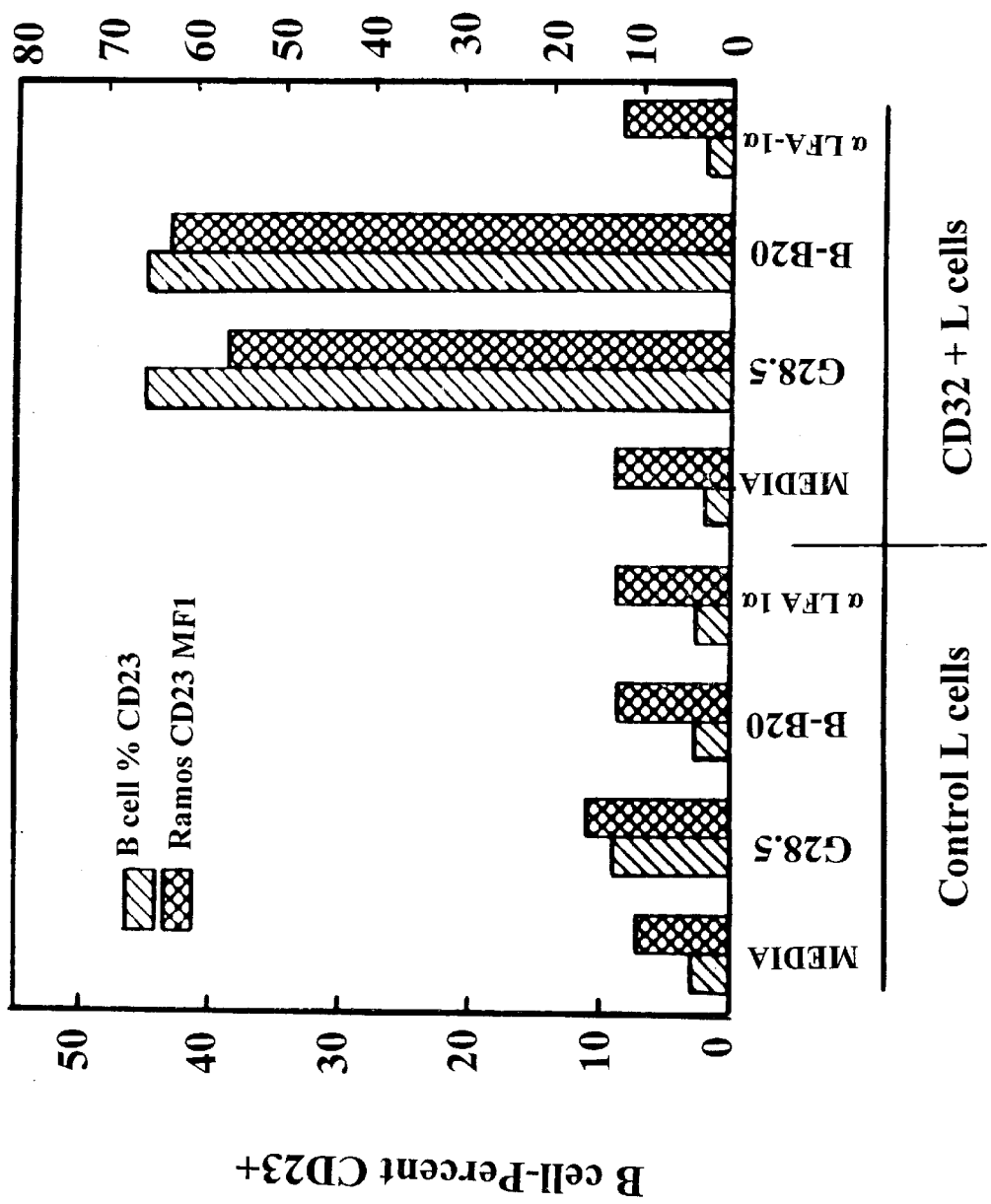
FIGS. 16A–B. Effect of anti-CD40 on CD32+ L cells on B cell CD23 expression. Shown are the results of 2-color FACS analysis of cultures of (FIG. 16A) peripheral B cells or RAMOS 266 and (FIG. 16B) tonsil and spleen B cells after 18 h of culture with monolayers of I-A+ L cells (L cells) or FcRgII+ L cells (CD32+ L cells) in the presence of the indicated mAbs or control media. In (FIG. 16A) the left y axis shows percentage of IgM+ B cells expressing CD23 and the right y axis shows MFI of CD23 on RAMOS (described in legend to FIG. 1.). In (FIG. 16B) "control" refers to anti-LFA1a for tonsil experiment and anti-CR2 (THB-5) for spleen experiment.
Figure 16B:
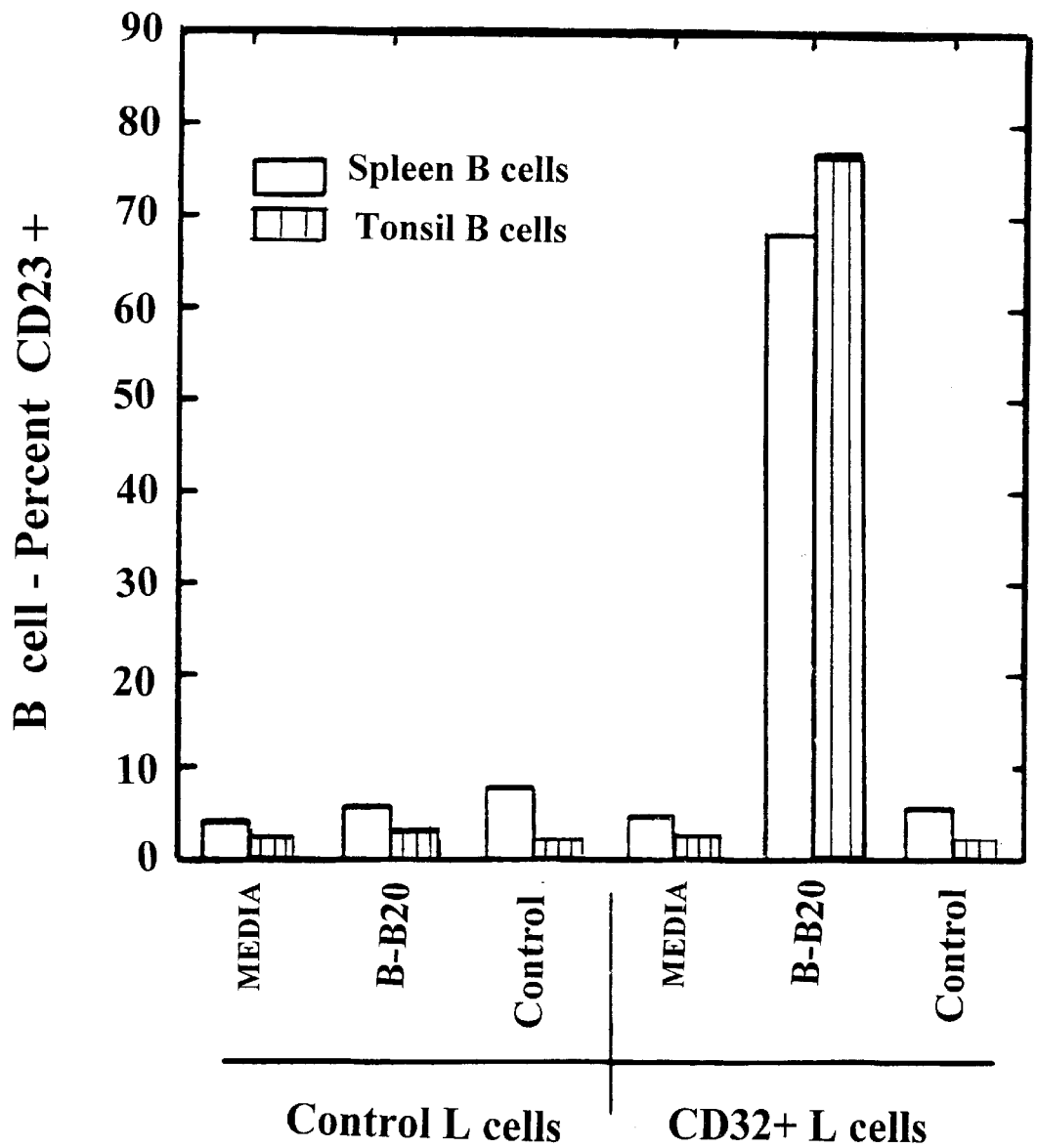
Figure 17A:
FIGS. 17A–E. T-BAM expression in human normal lymphoid tissues. T-BAM expression was evaluated in frozen tissue section of (FIGS. 17A–B) normal tonsil A. x25, B. x40 and (FIG. 17C) normal lymph node (x25) and normal spleen (FIG. 17D x25.
Figure 17B:
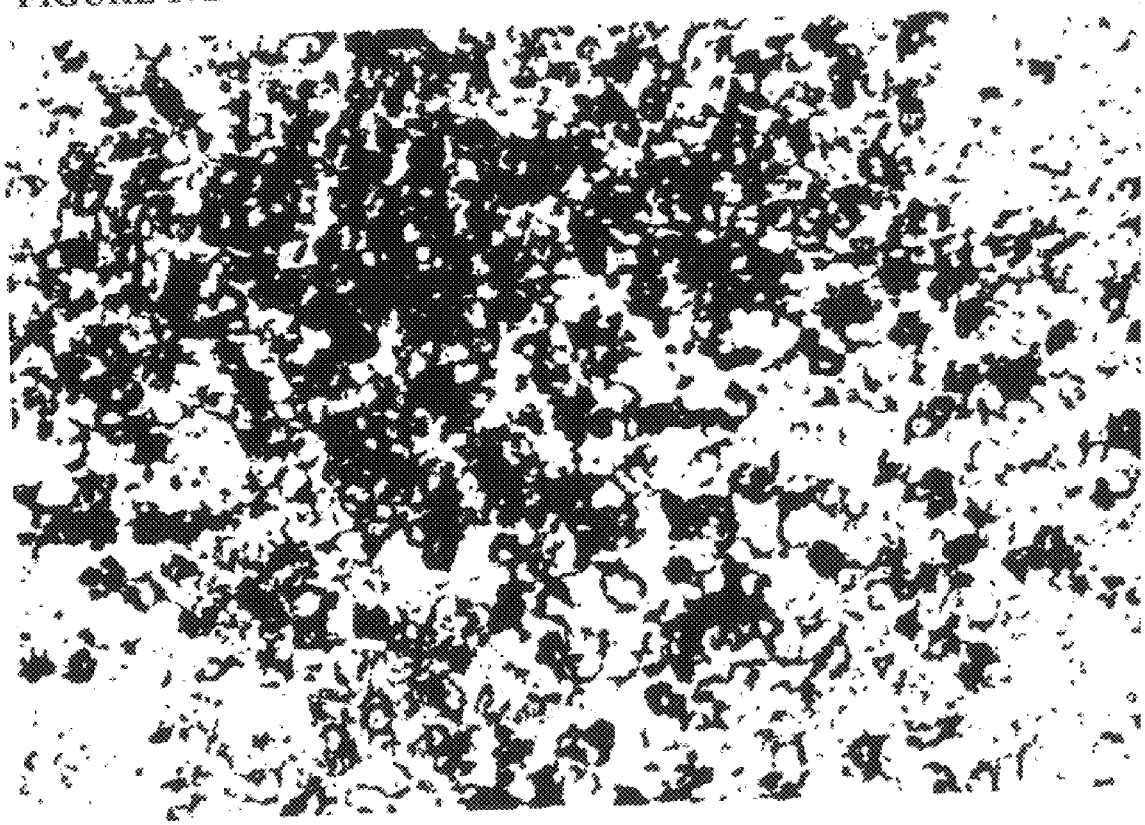
Figure 17C:
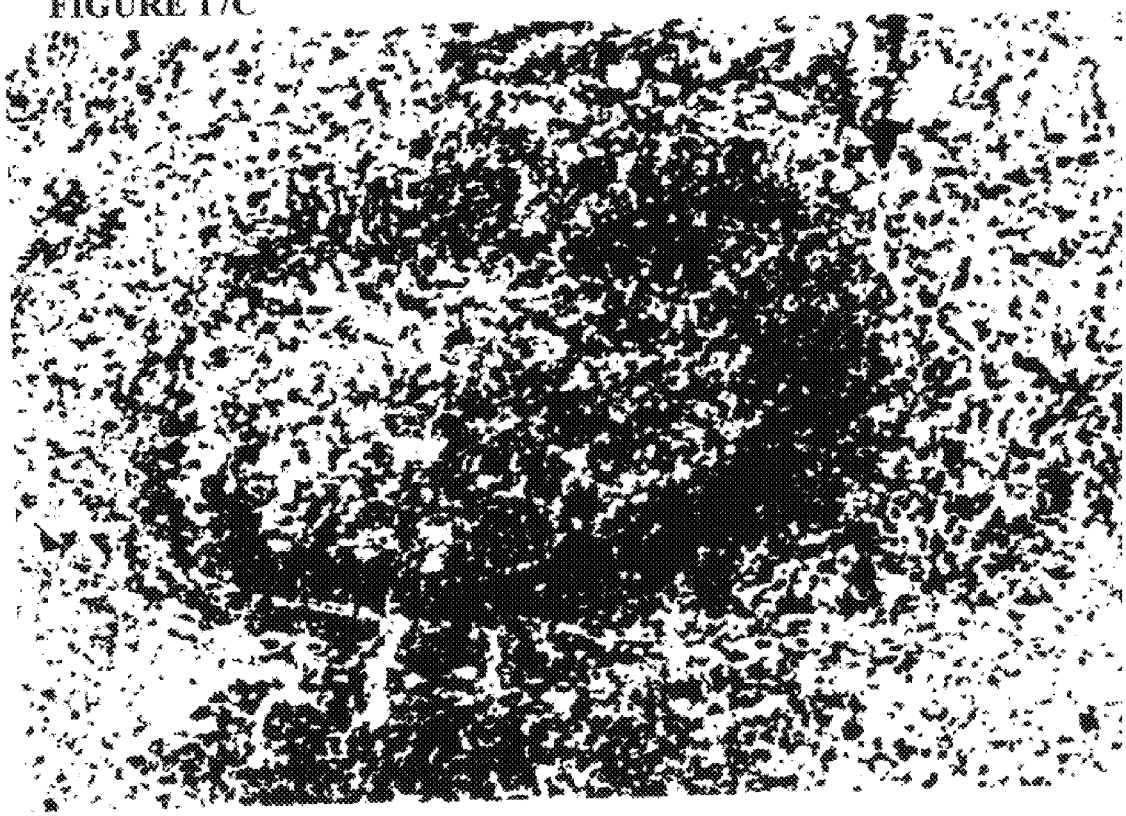
Figure 17D:
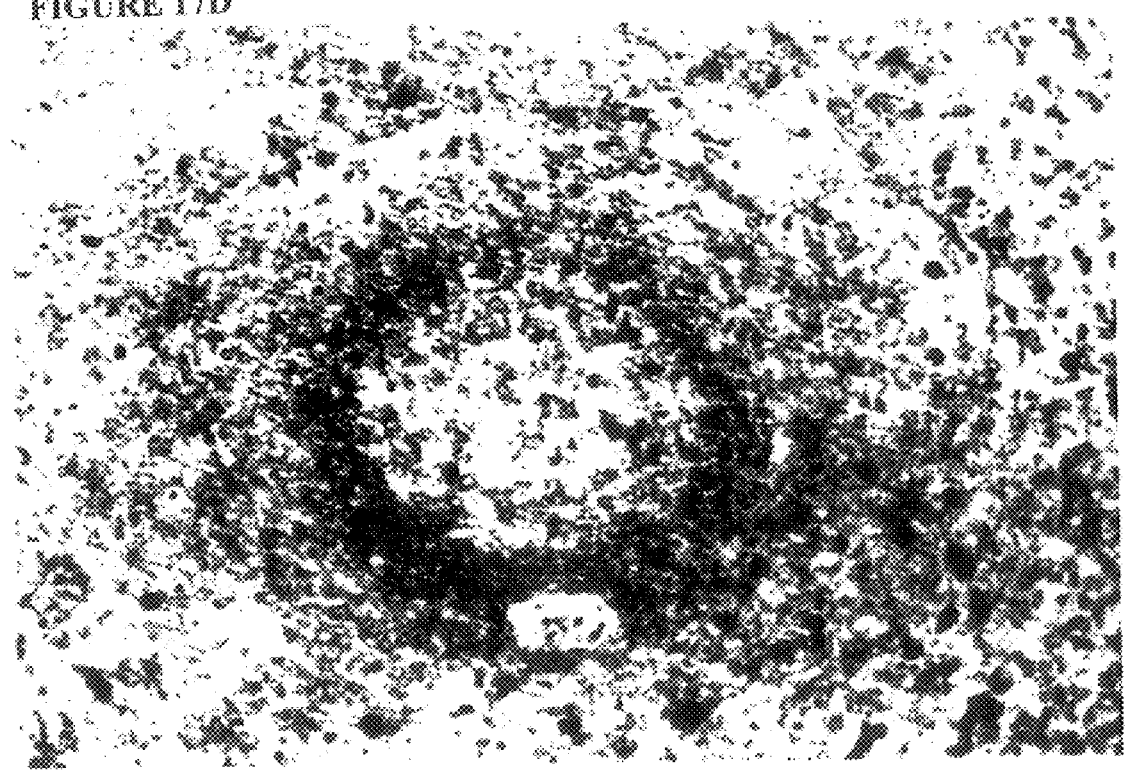
Figure 17E:
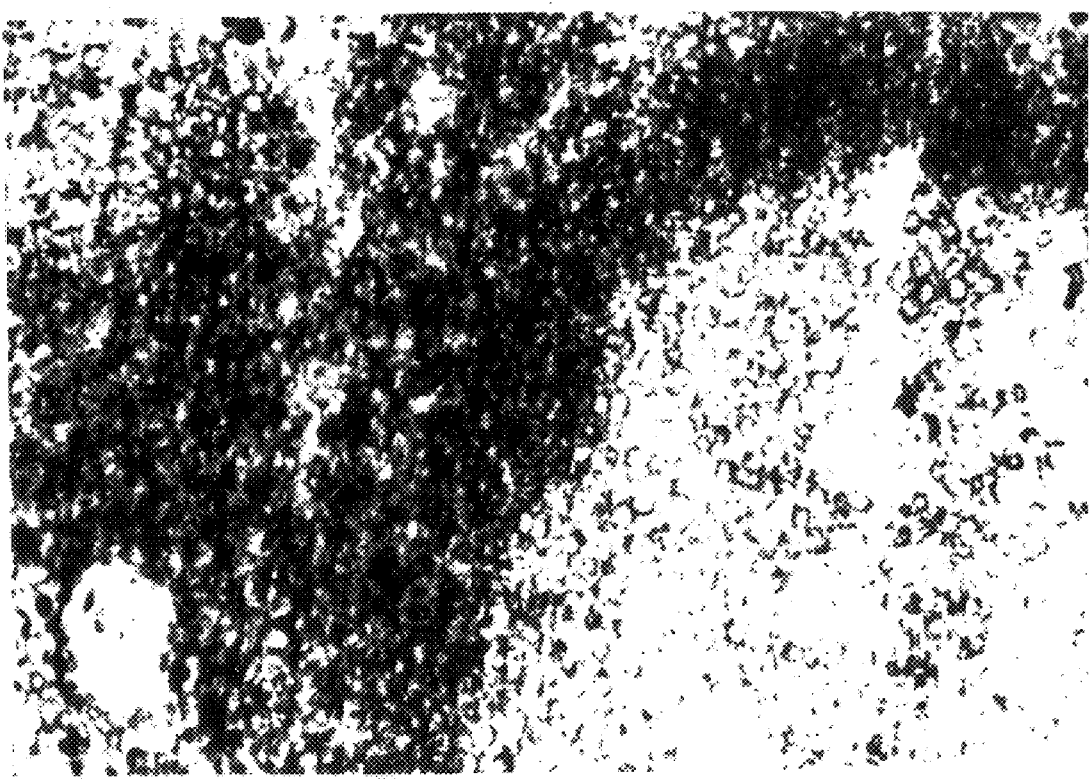
Figures 1, 19A:
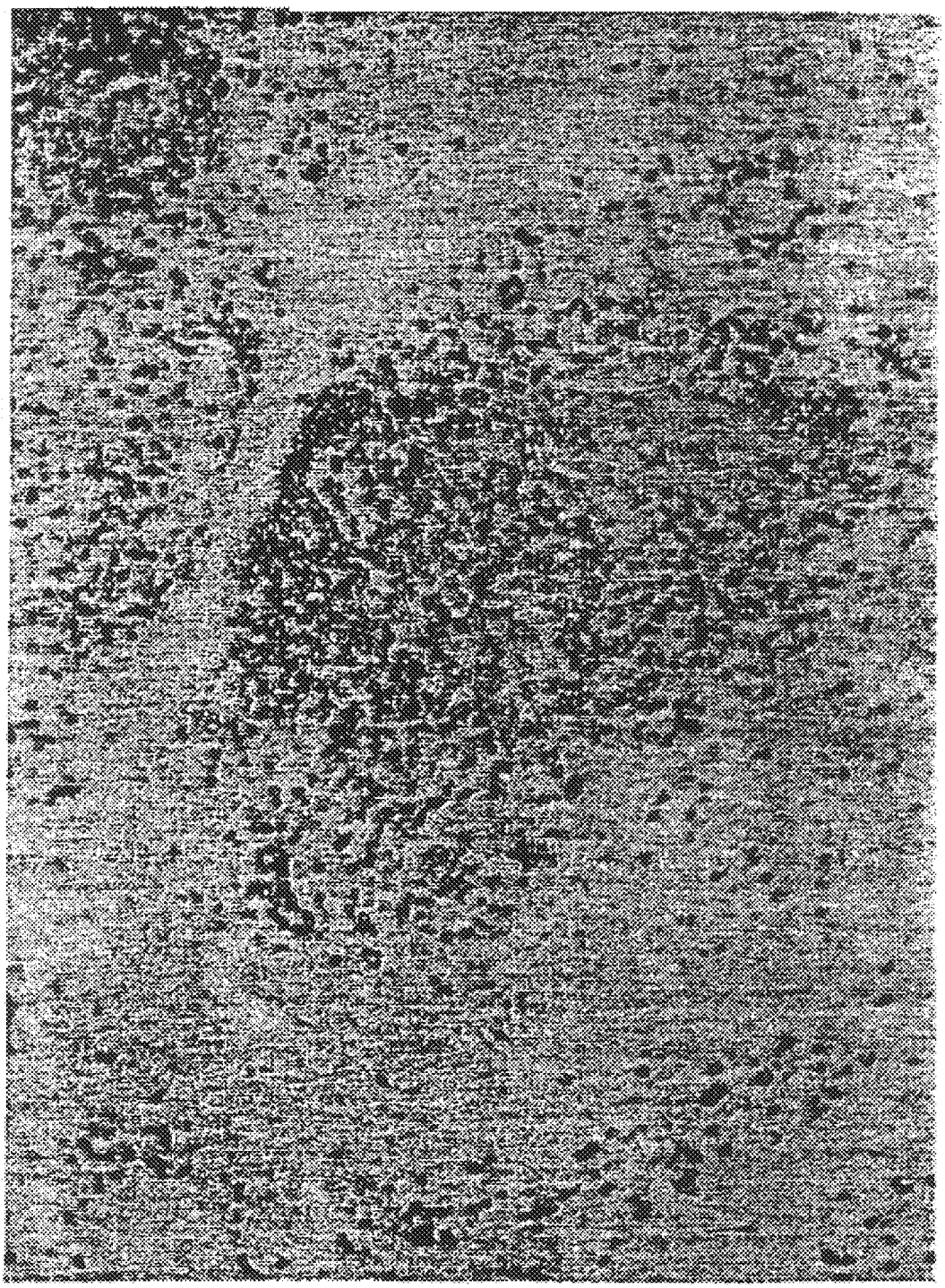
FIGS. 19A–D. Expression of T-BAM on CD4+ T lymphocytes in synovial pannus of Rheumatoid Arthritis. Shown are immunohistochemically stained sections of a lymphoid follicle in syrovial pannus from a patient with active, cellular rheumatoid arthritis.
Figures 2, 19A:
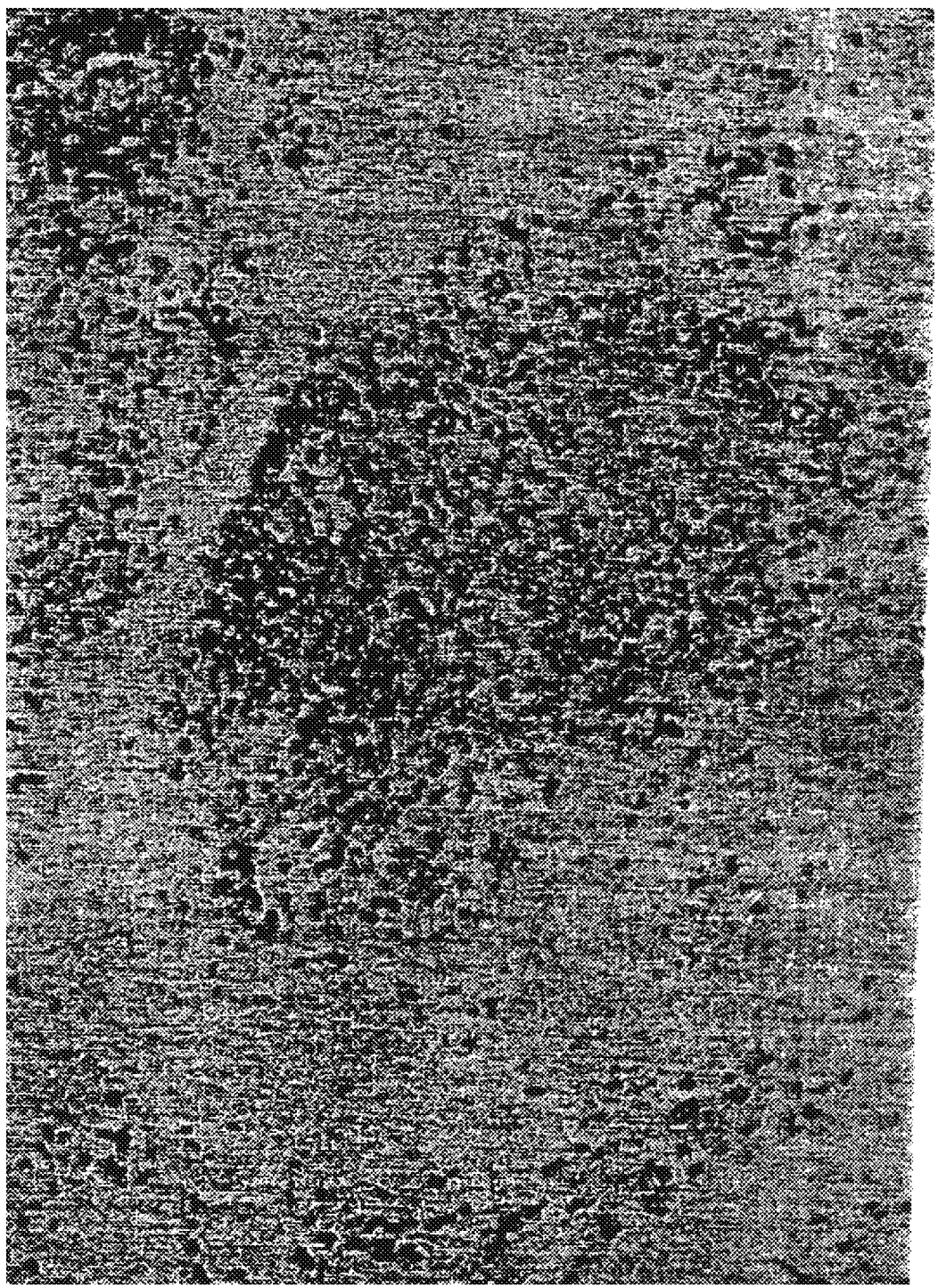
Figures 1, 19B:
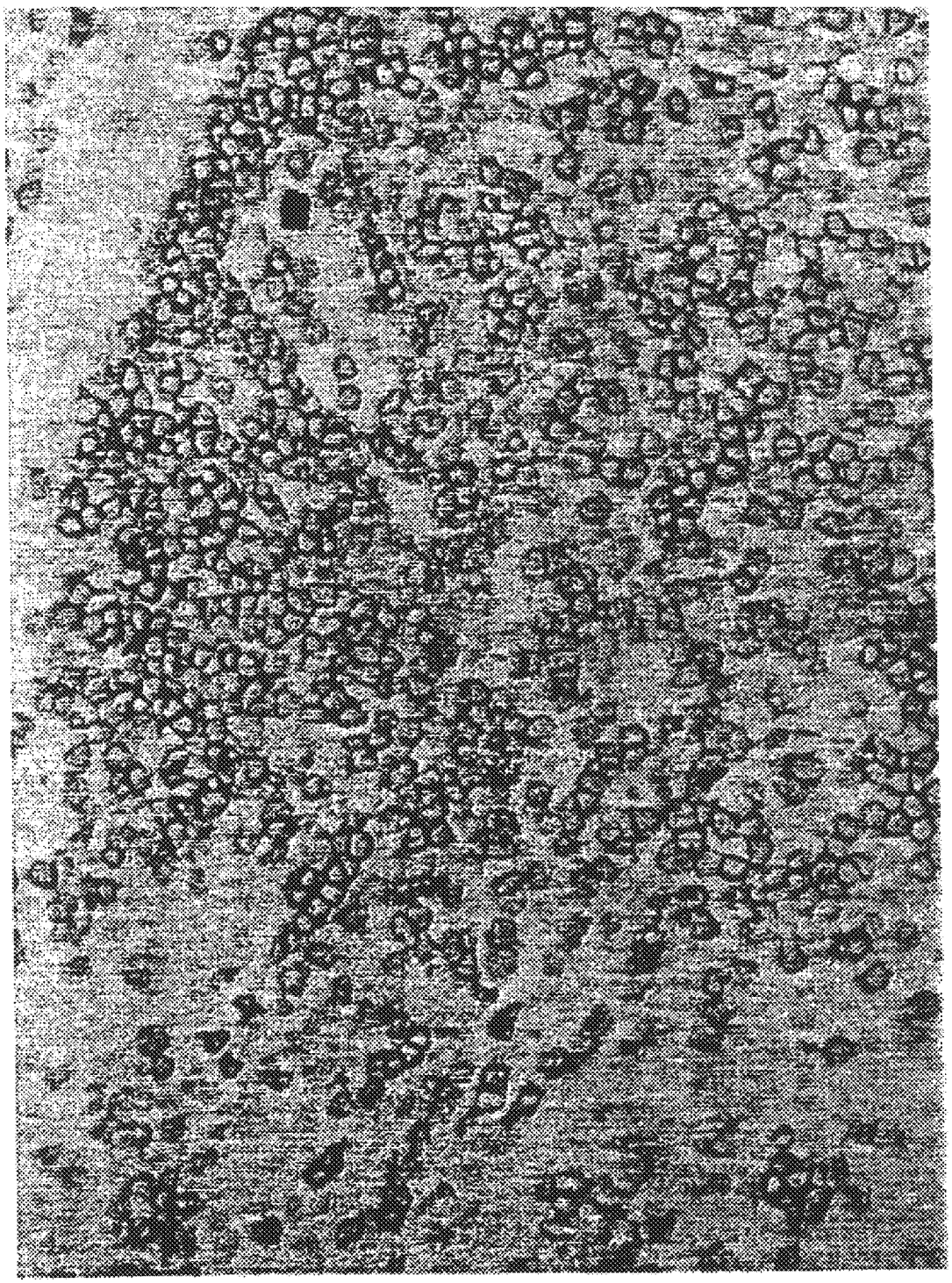
Figures 2, 19B:
Figures 1, 19C:
Figures 2, 19C:
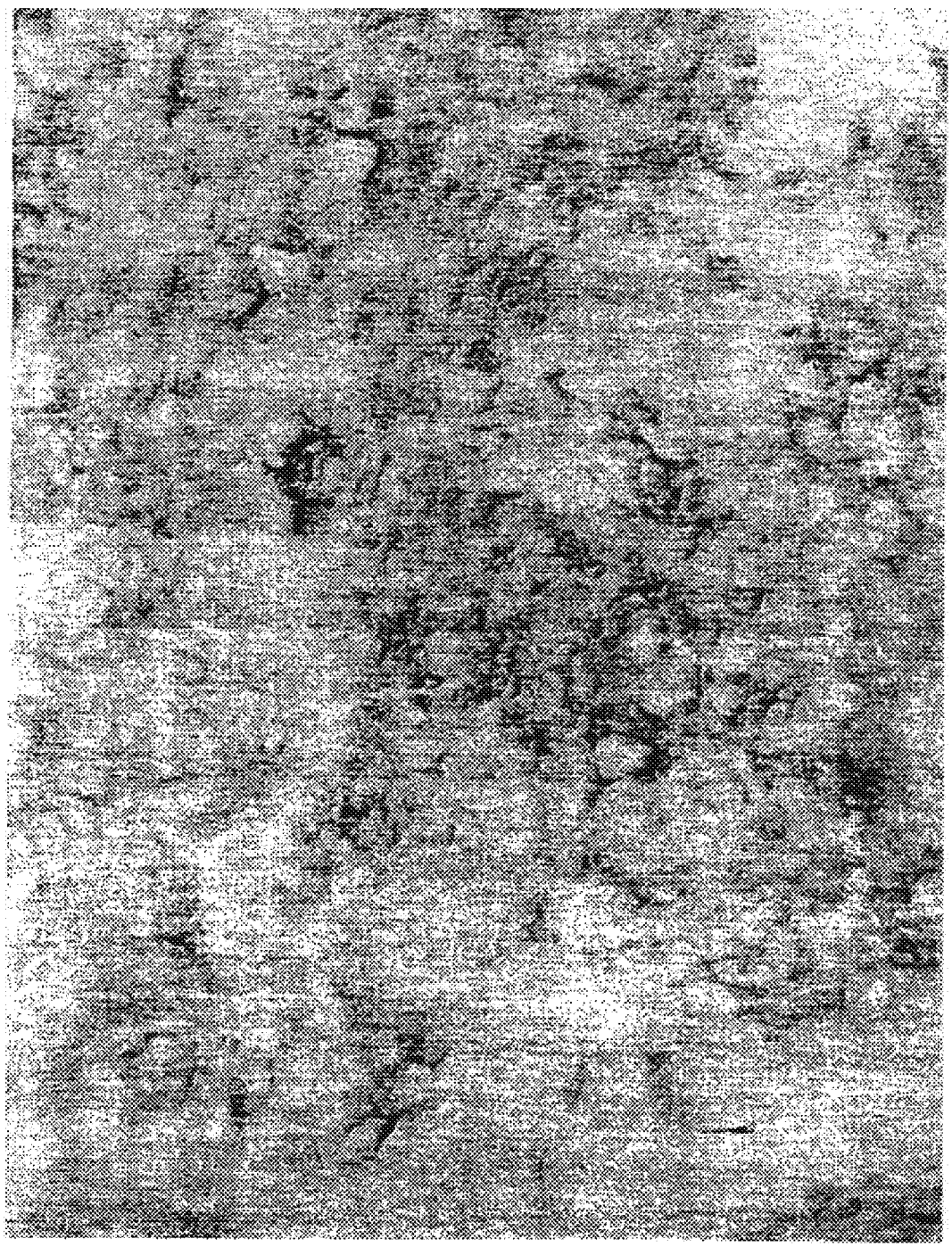
Figures 1, 19D:
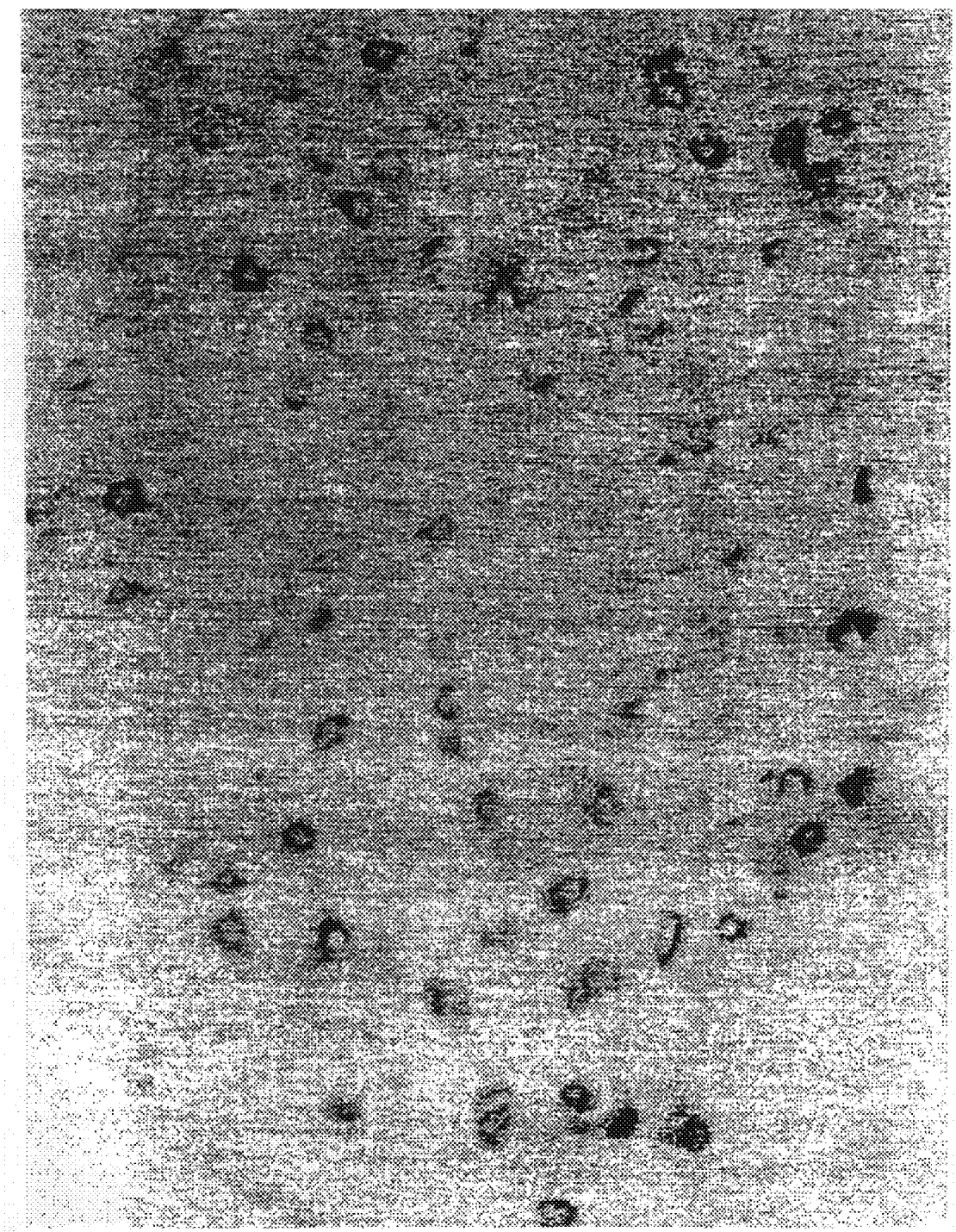
Figures 2, 19D:
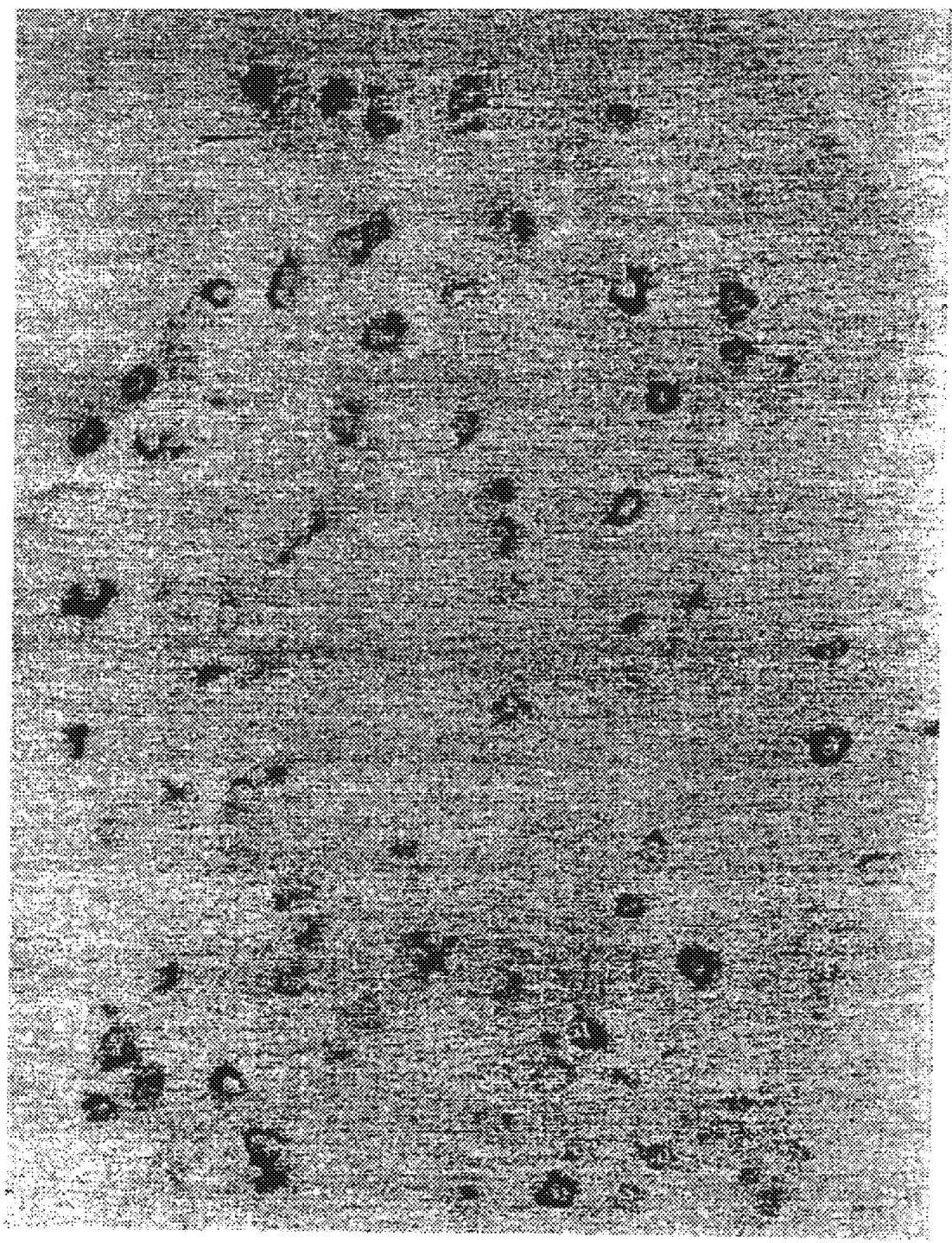
Figures 1, 20A:
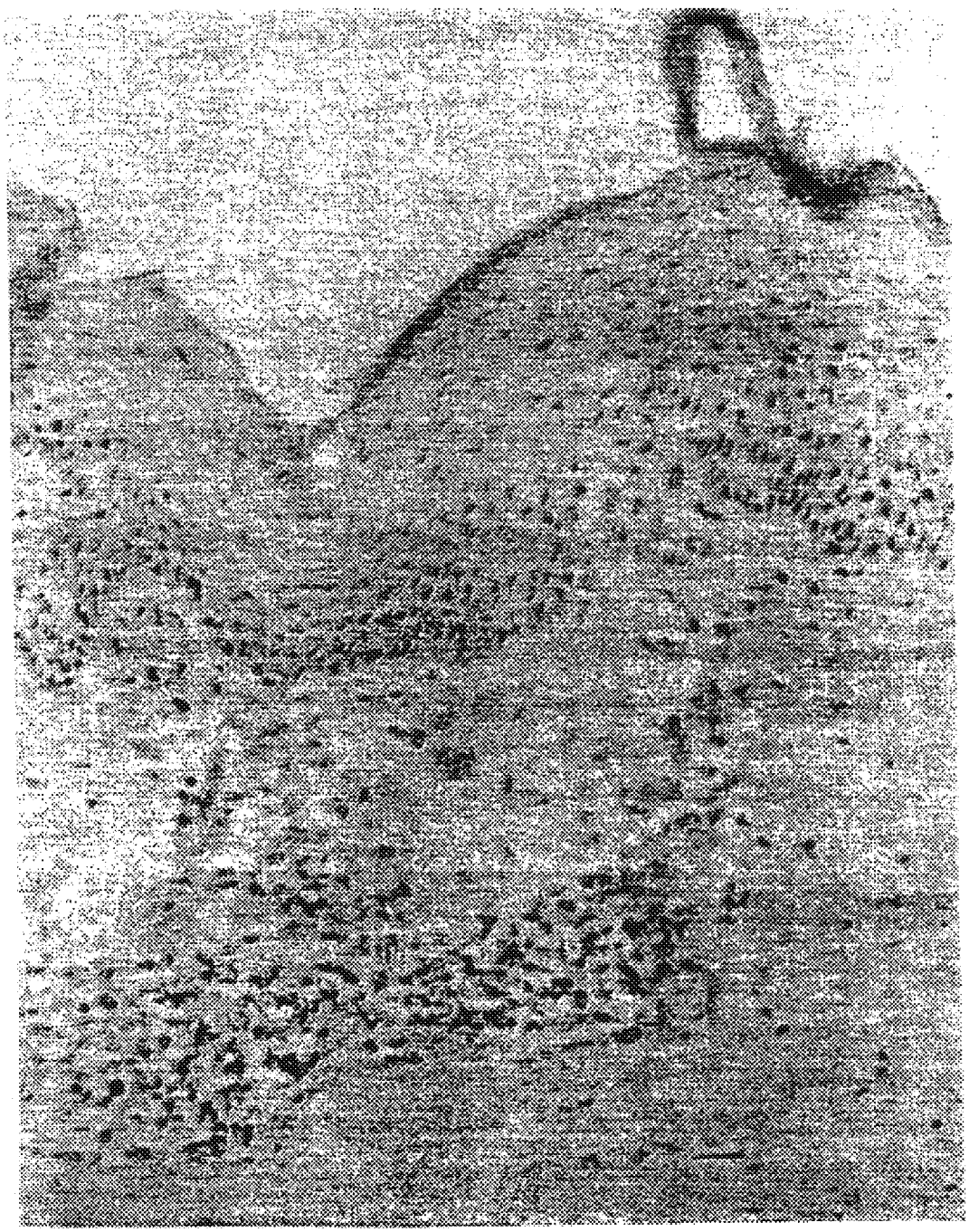
FIGS. 20A–B. Expression of T-BAM on T lymphocytes infiltrating psoriatic lesions. Shown are immunohistochemical staining of a skin biopsy specimen from a psoriatic lesion (FIG. 20A low power), (FIG. 20B high power)—infiltration of T cells in dermis. T-BAM expression detected by mAb 5c8 and diaminobenzidine (DAB) (brown).
Figures 2, 20A:
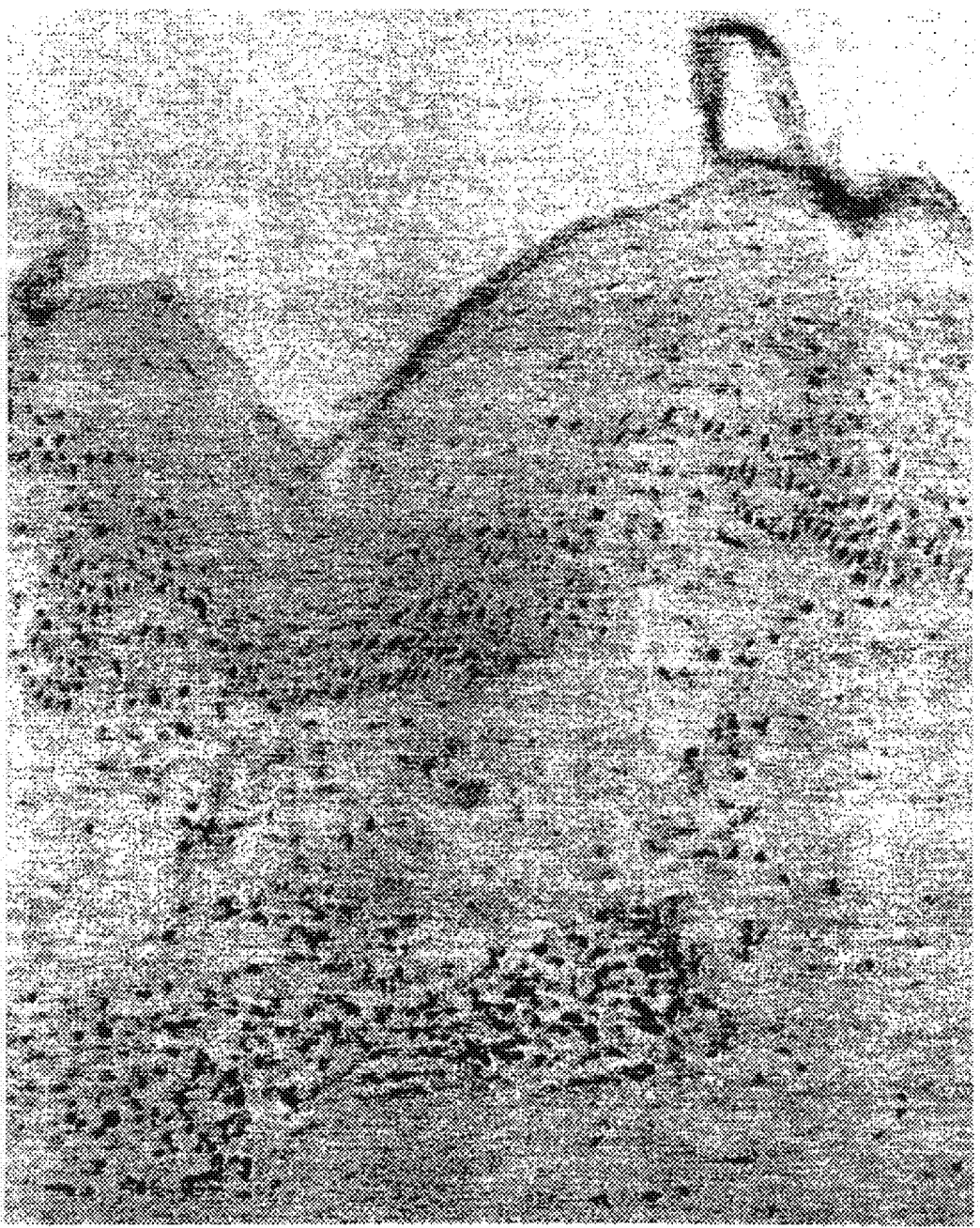
Figures 1, 20B:
Figures 2, 20B:
Figures 1, 21A:
FIGS. 21A–B. Expression of T-BAM on non-Hodgkins' lyphoma cells. Shown are immunohistorchemical specimens from lymph nodes of two patients with non-Hodgkin's lymphoma demonstrating T-BAM+ T cells (brown, DAB) (FIG. 21A 530x and FIG. 21B 400x).
Figures 2, 21A:
Figures 1, 21B:
Figures 2, 21B:
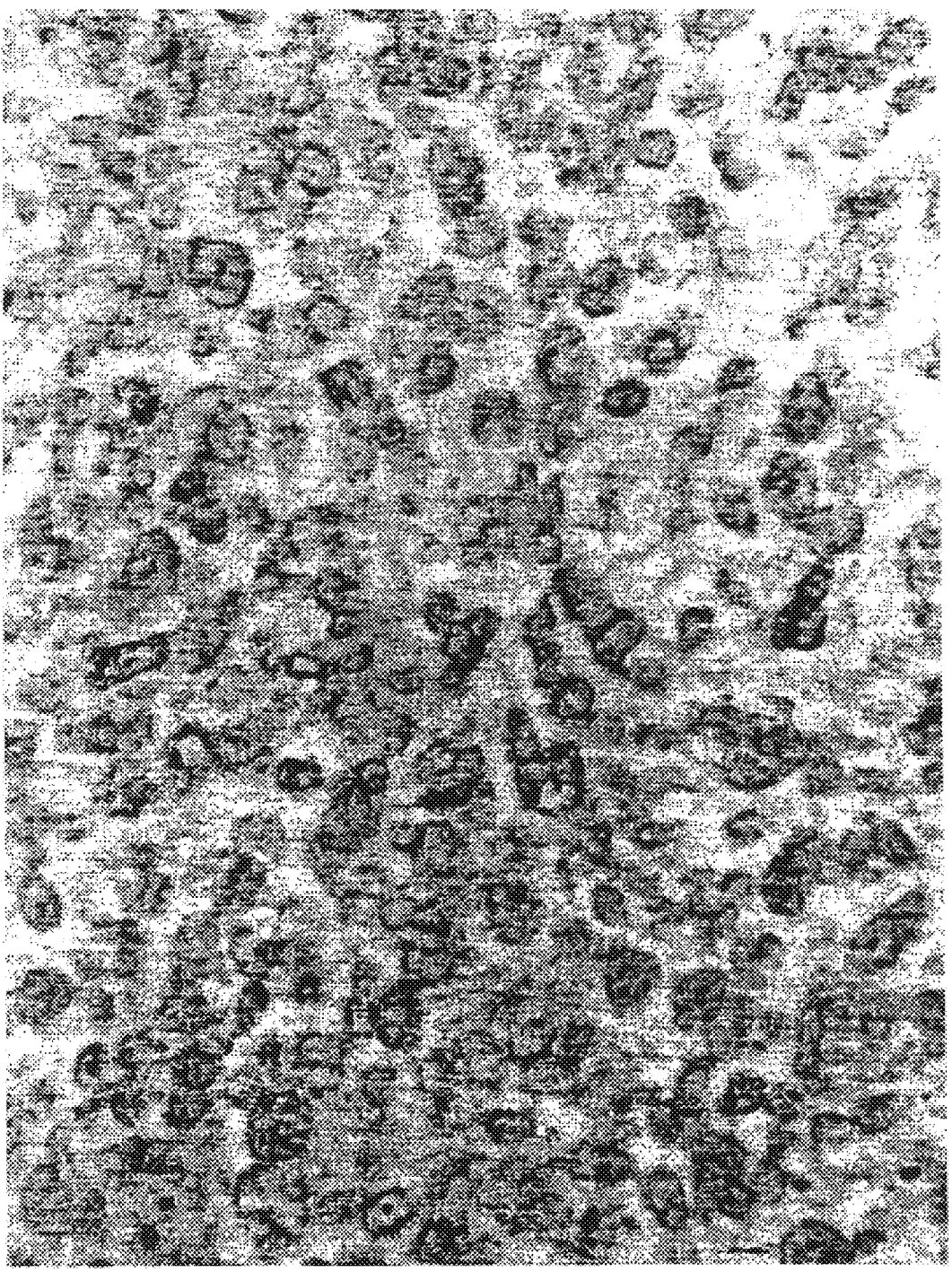

It is currently unknown how anti-CD40 inhibits contact help interactions but potentiates other B cell activating signals. One possibility is that D1.1 expresses a surface molecule that interacts with CD40. We reasoned that if surface molecules on D1.1 cells are interacting with CD40 to stimulate B cells, then anti-CD40 antibodies in a multimeric configuration may mimic the D1.1 effect and upregulate B cell CD23. Therefore, the effect of G28-5 on RAMOS 266 and B cell CD23 was studied in the presence of FcgRII expressing L cells, which is a configuration that has been shown to induce peripheral B cells to proliferate (Banchereau, et al., 1991a). Therefore, we cultured B cells in the presence of G28-5, B-B20 or control mAbs in the presence of FcgRII expressing and control L cells and studied the expression of B cell CD23 after 18 h. It was found that polyvalent, but not monovalent, anti-CD40 induced CD23 expression on peripheral B cells and RAMOS (FIG. 16a) as well as on tonsil and spleen B cells (FIG. 16b). Taken together, these data show that multimeric anti-CD40 mAbs activate B cells to express CD23 and suggest that the inhibitory effect of anti-CD40 mAbs in the D1.1 system may be the result of monomeric anti-CD40 mAb inhibiting the interaction of CD40 molecules with a crosslinking ligand on the surface of D1.1.

Expression of T-BAM in Areas of Lymphoid Tissue Involved in T-B Interactions

Because CD4+ T cells mediate helper function in transient, antigen induced structures in lymphoid tissues termed follicles or germinal centers, the tissue distribution of T-BAM was investigated by immunohistochemistry to examine if T-BAM is expressed on T cells in lymphoid follicles. Frozen tissue sections prepared from normal human tissues were fixed with acetone and stained with mAb 5c8 and a variety of control mAbs by immunohistochemistry. The expression of T-BAM was restricted to relatively small mononuclear cells in lymphoid tissue (FIG. 16) and was not observed in any other tissues, including muscle, brain, kidney, intestine, ovary, uterus, testes, skin, lung or liver (see Materials and Methods).

In order to characterize the precise localization of T-BAM bearing cells in lymphoid tissue, tonsils, lymph nodes, GI associated lymphoid tissue, spleen and thymus were analyzed. T-BAM expressing cells are preferentially localized in the mantle zone and terminal center light zone of secondary follicles of all peripheral lymphoid tissues in a pattern that strongly parallels the distribution of CD4+ T lymphocytes in these sites (FIG. 17). In tonsil, two color immunohistochemical analysis with mAb 5c8 and either anti-CD4 or anti-CD8 demonstrated that T-BAM expression is restricted to CD3+CD4+ T lymphocytes and is not observed on CD8+ T cells (not shown). Furthermore, dual staining suggested that a large majority (>50%) of CD4+ T lymphocytes within secondary follicles express T-BAM.

Because the in vitro data show that T-BAM and CD40 both participate in a contact dependent interaction, we were interested in studying the relationship of T-BAM and CD40 expressing cells in vivo. Using anti-CD40 mAbs in single and two color immunohistochemical analysis, the known observation that both B cells and follicular dendritic cells highly express CD40 was confirmed (Clark, et al., 1986; Hart, et al., 1988) (data not shown). Because T-BAM expressing T cells are surrounded by abundant CD40+ B cells, we were unable to determine the relationship of T-BAM expressing T cells with follicular dendritic cells because of the high concentration of B cells. In order to precisely identify the relationship of T-BAM expressing cells with the dendritic cells within the follicular germinal center, we performed two color immunohistochemical analysis using mAb 5c8 and anti-CD11c mAbs, which are known to recognize follicular dendritic cells. Using this approach we demonstrated that T-BAM cells are often in proximity or in direct contact with follicular dendritic cells and/or their cytoplasmic projections, indicating perhaps, that in addition to interactions with CD40+ B cells, T-BAM expressing T cells may interact with follicular dendritic cells that also express CD40 (data not shown).

In addition to the distinctive localization of T-BAM expressing cells in follicles, relatively rare (<1%) T-BAM expressing cells can also be identified within the interfollicular areas of peripheral lymphoid tissues, splenic T cell areas and the cortex of normal thymus. The scarcity of T-BAM expressing T cells in thymus was of interest given the high number of CD4 expressing cells in this tissue. Taken together, the in vitro functional data and the localization of T-BAM bearing cells in anatomic areas of physiologically relevant T-B interactions, strongly support the notion that T-BAM is important in T cell help in vivo.

Discussion

The interactions between T and B cells that result in specific antibody responses involve critical contact dependent interactions during the effector phase of T helper function. The CD4+ T cell-restricted surface activation protein, T-BAM, has recently been shown to be a component of the contact dependent helper signal to B cells (Lederman, et al., 1992). The molecular interactions that mediate T-B contact dependent signalling were further studied using a T-BAM expressing cell line (D1.1) and an anti-T-BAM mAb (5c8) that blocks T-BAM mediated B cell activation (Lederman, et al., 1992). In this second series of experiments, it was shown: 1) that in addition to B cells from peripheral blood, lymphoid B cells and a B lymphoma clone (RAMOS 266) respond to D1.1 cell contact in a manner that is inhibited by anti-T-BAM (mAb 5c8); 2) that CD40 is a surface structure on B cells (CD40) that participates with T-BAM in mediating contact dependent T-B activation; and 3) that T-BAM is expressed by T cells located predominantly in the mantle and centrocytic zones of lymph nodes in vivo which are the anatomic sites of T cell interactions with CD40 expressing B cells. These data strengthen the idea that T-BAM is a potentially relevant signal delivered by T cells to B cells in the process of lymph node B cell differentiation.

Further, the availability to RAMOS 266, which appears to express the T-BAM ligand, will be useful in the generation and screening of antibodies to other B cell surface structures that play roles in contact dependent helper signalling as well as to biochemically characterize the molecular messengers that mediate T-dependent B cell differentiation.

Utilizing the D1.1-RAMOS 266 system, in the present report, we analyzed the role of certain B cell surface molecules in contact dependent help. We observed that the anti-CD40 mAbs G28-5 and B-B20 inhibit the effect of D1.1 cells on RAMOS 266 and B cells from both peripheral blood and lymphoid organs in contrast, mAbs to CR2, LFA1, LFA3 and ICAM-1 do not inhibit the D1.1 effect on B cells. These data suggest a precise role for CD40 in receiving a T cell signal that is coincidant and highly associated with T-B cell contact. However, our system does not address the precise roles of LFA1 and ICAM-1 in T-B interactions. Although the mAb anti-ICAM-1 (RR1/1.1.1) does not inhibit the D1.1 mediated activation of RAMOS 266 or B cells, this mAb is known to partially inhibit contact dependent B cell proliferation by fixed activated T cells (Tohma, et al., 1991a). It is tempting to speculate that the T-BAM and CD40 dependent interaction that we have described may induce subsequent interactions that depend on LFA1-ICAM1 interactions, since it is known that anti-CD40 triggering stimulates T-B adhesion that depends on LFA1-ICAM-1 interactions (Barrett, et al., 1991).

The inhibitory effect of anti-CD40 mAbs for D1.1 triggering was in contrast to their potentiating effect on rIL-4 induced CD23 expression. These data suggest that inhibition of the D1.1 effect by anti-CD40 mAb was not the result of a generalized inhibition of B cell responsiveness. In addition, anti-CD40 mAbs G28.5 and B-B20 induced CD23 expression on RAMOS 266, and on peripheral and lymphoid B cells when presented in crosslinked form on the surfaces of FcrgII+ L cells. Taken together, these studies suggest that polyvalent anti-CD40 may mimic the effect of D1.1 cells and are consistant with the notion that the ligand for CD40 may be a D1.1 surface structure.

The inhibitory effects of mAb 5c8 and the anti-CD40 mAbs in the D1.1 system suggest that both T-BAM and CD40 play roles in T-directed, contact dependent signalling of B cells which occurs in lymph nodes in vivo. To address the role of T-BAM in physiological T-B interactions, the expression of T-BAM in vivo was studied by immunohistochemristry. T-BAM expression was found to be restricted to CD4+ T lymphocytes in lymphoid tissues. These data show that in vivo, as well as in vitro, T-BAM expression is restricted to CD4+ T cells and is not expressed on CD8+ T cells. Taken together, these data suggest that the CD4+ and CDB+ T cell populations represent distinct T cell lineages that differ not only with respect to their expression of CD4 and CD8, but with respect to at least one other molecule (T-BAM) and suggest that the restriction of T-BAM expression to CD4+ cells is a molecular basis for the restriction of helper function to the CD4+ subset.

In addition to its restriction to CD4+ T cells, T-BAM appears to be unique among known human surface T cell activation molecules in that its expression is restricted to T cells in lymphoid organs in vivo. In the rat, a 50 kDa MW protein termed OX-40 is expressed exclusively by CD4+ T cells after in vitro activation, but the reported pattern of OX-40 expression in spleen (Paterson, et al., 1987) appears to be distinct from the mantle and centrocytic zone expression of T-BAM that we observed. However, understanding the relationship, if any, between these molecules will require identification of relevant homologies of these structures in both species. Taken together, the in vitro functional data and the immunohistochemical analysis suggest that T-BAM expressing CD4+ T cells are involved in helper function, which is known to occur in lymph node germinal centers.

The new data, presented in this study may help to elucidate the role that T cells play in the process of lymphoid follicle B cell differentiation (reviewed in (Liu, et al., 1992; Nossal, 1992)). In lymphoid follicles, antigen stimulated B lymphocytes undergo extensive cell proliferation and somatic mutation within the centroblastic (dark) zone of germinal centers. The centroblastic B cells then enter the centrocytic (light) zone where B cells are selected by T cells either for survival or death (apoptosis) based on the affinity of their antigen receptors. The B cells that are positively selected are then directed by T cells to differentiate either into memory B cells or into antibody forming plasmablastoid cells that in some cases are further directed to undergo gene rearrangements to form the functionally distinct Ig isotypes. Therefore, although the signals that direct B cell differentiation are not completely understood, it appears that T cells participate in at least three distinct decisions in lymph node B cell differentiation: survival or death, memory or plasmablastoid lineage, and the selection of antibody isotype. The observation that T cells in the centrocytic zone express T-BAM suggests that T-BAM may play a role in determining the fate of B cells with respect to certain of these decisions. Future studies will address the specific roles that T-BAM plays in these T cell dependent processes in lymph node B cell differentiation.

The observation that anti-CD40 mAbs inhibit a discreet, T contact-mediated interaction with D1.1 cells suggests that a similar CD40 dependent interaction may underlie certain of the reported effects of anti-CD40 on more complex, physiological responses. Anti-CD40 (G28-5) potently inhibits programmed cell death (apoptosis) of cultured germinal center B cells (Liu, et al., 1989). In addition, G28.5 inhibits the generation of plasmablastoid and switched germinal center B cells induced in vitro by soluble rCD23 and IL-1a (Liu, et al., 1991). Although the role of T cell contact in these CD40 dependent phenomena is currently unknown, the data presented here demonstrate that CD40 plays a specific role in T-B contact interactions and provides an avenue for identifying the CD40 ligand and for more precisely defining the signalling functions of CD40.

Because these studies have identified important roles for T-BAM on T cells and CD40 on B cells in T-B collaboration, it is relevant to explore the possible relationships of these molecules. We propose two models that can account for the data. The possibility that T-BAM interacts directly with CD40 is the simplest model that accounts for all the data (FIG. 7, Model #1.). However, in the absence of definitive biochemical binding data that shows T-BAM-CD40 interaction, it is important to note that another possibility is that T-BAM and CD40 interact with distinct ligands (FIG. 7., Model #2). If T-BAM and CD40 interact with different ligands, the functional data suggest that both the CD40-x and the T-BAM-y interactions are necessary but not sufficient for B cell CD23 induction.

Although the "counter-receptors" for T-BAM("x") and CD40 ("y") appear to be B and T cell surface molecules, respectively (FIG. 7., Model #2.a.), our data do not exclude the possibility that CD40 is the receptor for a B cell secreted (autocrine) factor (FIG. 7., Model 2b.). Although CD40 was previously thought to be a cytokine receptor, based on its structural homology to the NGF receptor (Stamenkovic, et al., 1989; Clark, 1990), the possibility that it is a counter-receptor for a T cell surface protein involved in helper function is consistant with the fact that crosslinked anti-CD40d mAb on FcRgII+ L cells mimics the activating surface features of D1.1 cells.

In addition to B cells, follicular dendritic cells express CD40 and we have found T-BAM expressing T cells in close proximity and possibly associated with follicular dendritic cells. A T cell-CD40 interaction could be important in the function interaction of T cells with follicular dendritic cells which are known to play a role in Ag processing in lymph nodes (Gray, et al., 1988; Askonas, et al., 1972; Gray, et al., 1991). In addition, an interaction of CD4+ T cells with CD40+ follicular dendritic cells may have special pathogenic significance in AIDS where follicular dendritic cells are known to be a reservoir of HIV (Spiegel, et al., 1992).

If Model #2. is correct, and T-BAM interacts with a ligand other than CD40, then T-BAM may have signalling roles on cells that do not express CD40. In this regard, CD4+ T cells interact with other T cells (CD4+ and CD8+) to mediate the induction of cytotoxicity (Bennink, et al., 1978; Ashman, et al., 1979; Kast, et al., 1986; Zinkernagle, et al., 1978; Leist, et al., 1989) and suppression (Thomas, et al., 1980; Thomas, et al., 1982). In addition, CD4+ T cells interact with macrophages to mediate activating signals (Zimecki, et al., 1988; Zimecki, et al., 1989; Weaver, et al., 1989; Wasik, et al., 1988; Fau, et al., 1990; Fau, et al., 1988). An important goal of future research will be to determine if T-BAM is involved in activating other cells, or whether other, possibly related, molecules play such roles.

Third Series of Experiments

Pre-clinical studies on the monoclonal antibody 5c8; a murine monoclonal antibody directed against T-BAM The overall goal of the studies is to evaluate the utility of a novel monoclonal antibody (mAb) in the diagnoses and treatment of inflammatory and neoplastic diseases. Central to these studies is the recent generation and characterization of a murine mAb, termed 5c8, that recognizes a novel surface protein (T-BAM) on activated human CD4+ T helper lymphocytes.

Importantly, the mAb 5c8 blocks effector functions of CD4+ T cells including the process by which B cells are driven to produce specific antibodies. In healthy human tissue, T-BAM is exclusively expressed on CD4+ T cells in transient, antigen induced structures in lymphoid organs termed germinal centers. However, preliminary studies on tissues from a variety of inflammatory diseases have revealed that T-BAM is expressed by CD4+ T lymphocytes infiltrating the diseased tissues. To date, infiltration of T-BAM expressing CD4+ T cells was observed in joint tissue affected by rheumatoid and osteo-arthritis and in the skin affected by psoriasis, contact dermatitis and a hyper-IgE syndrome. Because T-BAM appears to play a key role in CD4+ T cell effector functions in vitro, the presence of T-BAM expressing CD4+ T cells at sites of inflammation in vivo suggests that T-BAM may participate in the immune pathogenesis of these diseases. The availability of the anti-T-BAM mAb, 5c8, affords us the opportunity to ask whether T-BAM bearing CD4+ T cells, or the T-BAM molecule, itself, have critical roles in these processes. If T-BAM+ CD4+ T cells are found to have critical roles in certain diseases, it might be possible to specifically target the offending, pathogenic CD4+ T cells using the mAb 5c8 either to lyse or poison T-BAM+CD4+ T cells or to block their functions. In addition, aberrent expression of the T-BAM molecule was observed on a number of lymphoid malignancies, suggesting that the mAb 5c8 may have applications in the diagnosis and treatment of lymphoid tumors. Taken together, these observations suggest the utility of the mAb 5c8 in the diagnosis and treatment of inflammatory diseases and lymphoid neoplasia.

The following areas will be investigated or evaluated:

1. The expression of T-BAM in affected tissues from patients with inflammatory, autoimmune, allergic and neoplastic diseases and determine whether expression of T-BAM, correlates with extent of disease.
2. The effects of mAb 5c8 on in vitro systems of lymphocyte function using cells from individuals with inflammatory, autoimmune or allergic diseases.

3. The effect of mAb 5c8 on the function of T lymphocytes from non-human primates (rhesus macaques) in order to eventually conduct safety and pharmacokinetic studies in such animals.
4. The potential use of 5c8 mAb as a diagnostic modality in the clinical evaluation of inflammatory diseases and leukemia/lymphoma.

Rationale

CD4+ T lymphocytes play a central role in the inflammatory response because activation of CD4+ T cells is required for the generation of both humoral (antibody-mediated) immune responses as well as for cytotoxic (killer) CD8 T cell responses. Commensurate with this pivotal role, CD4+ T cells are the earliest infiltrating cell in tissues during the inflammatory response in normal immune responses and in several idiopatho inflammatory diseases.

In addition to directing the inflammatory response in tissues, CD4+ T cells play a critical role (termed "helper function") in directing both the specificity and the effector functions (isotypes) of the humoral (antibody) mediated immune response. Helper function is mediated by CD4+ T cells which migrate to lymphoid organs and seed transient structures termed germinal centers which become populated with antigen specific (cognate) B cells. In rheumatoid arthritis and certain other autoimmune diseases (systemic lupus) characterized by autoantibody production, CD4+ T cells play pathogenic roles in the generation of autoantibodies. In allergy, CD4+ cells have a critical role in the elaboration of IgE antibodies and therefore in the maintenance of the allergic state.

CD4+ T cells have clonally distributed antigen receptors that recognize foreign, degraded peptide antigens presented to them by B cells and macrophages on self Class II MHC molecules. A CD4+ T cell clone that recognizes its specific antigen/MHC Class II ligand responds to such recognition by undergoing a transformation termed "activation" that includes the de nova expression of several surface molecules and the secretion of lymphokines.

A monoclonal antibody, termed mAb 5c8, was recently developed that identifies a novel 30 kDa structure (termed 5c8 Ag or T-BAM) that is expressed exclusively on activated, but not resting CD4+ T cells, but is not expressed by CD8+ T cells (Yellin, et al., 1991; Lederman, et al. 1991). Importantly, by the nature of its interaction with T-BAM, the mAb 5c8 blocks the ability of CD4+ T cells to drive B cells to produce antibodies (Lederman, et al., 1992). We therefore investigated the expression of T-BAM in vivo and found that in normal human tissues, T-BAM is expressed by exclusively by CD4+ T cells predominantly in the mantle and centrocytic zones of lymph nodes in vivo which are the anatomic sizes of physiologic T cell interactions with B cells Lederman, et al., 1992b). The discovery that the 5c8 Ag is a component of the surface structures on CD4+ T cells that mediate contact dependent activation of B lymphocytes led us to rename 5c8 Ag "T cell-B cell activating molecule" (T-BAM). The fact that T-BAM is expressed only by CD4+ T cells that have been activated suggested that the mAb 5c8 may be specific for CD4+ T cells that are involved in inflammatory responses.

Therefore, in preliminary studies, the expression of 5c8 Ag in inflamed tissues from patients with autoimmune and inflammatory diseases was examined. In rheumatoid arthritis T-BAM expressing CD4+ T cells were localized in rheumatoid synovial joint pannus, both in the germinal centers that characterize this condition as well as in the surrounding inflammatory tissue. In cases of inflammatory osteoarthritis, T-BAM expressing cells were found to be a significant component of the infiltrating inflammatory cells. In psoriasis, atopic dermatitis and hyper-IgE syndrome, T-BAM expressing T cells were prominent in the infiltrating lymphocytes in the dermis. In contrast to these specimens from individuals with inflammatory diseases, T-BAM expressing cells were not present in normal tissues outside of primary lymphoid follicles.

The finding that T-BAM expressing cells are infiltrating diseased tissue and are present in transient, regenerating anatomic structures in normals suggests that mAb 5c8 therapy may be useful therapeutically because 1.) mAb 5c8 may target pathogenic T lymphocytes while leaving resting, circulation T cells unaffected and 2.) depletion of 5c8 bearing T cells may not result in prolonged, systemic depletion of T-BAM expressing T cells because the activated pool of cells may be replenished by the circulating, resting pool. The possibility that mAb 5c8 therapy may remove or immobilize pathogenic CD4+ T cells and result in a transient episode of immune compromise (from depletion of germinal center T cells) suggests that such therapy may have significant benefits over existing immunosuppressive that are in widespread use or under development.

Immunosuppressive agents that are currently used in treating autoimmune diseases, idiopathic inflammatory diseases, and allergic disorders have their primary therapeutic effect by inhibiting the function of CD4+ T cells. However, these existing therapies, such as, cyclosporin A (sandimmune), azathoprine (immuran) and cyclophosphamide (cytoxan), inhibit CD4+ T cell functions globally and result in systemic immunosupression. Therefore, because of the limitations of such agents, it is the goal of many laboratories, including our own, to develop agents that specifically effect CD4+ T cells. For example, clinical trials are currently underway in Europe and the U.S. using murine monoclonal antibodies directed against the CD4 molecule that mediate systemic depletion of CD4+ T cells. In the majority of cases the depletion of CD4+ T cells is transient, however, a worrisome side effect that has been observed is the prolonged depletion of CD4+ T cells several months after therapy. Although clinical effects of such CD4+ cell depletion have not been observed, it is known that the absence of CD4+ T cells is the principal pathophysiological event in AIDS. Taken together, these considerations suggest that mAb 5c8, anti-T-BAM may have significant therapeutic advantages in diseases mediated by infiltrating CD4+ T cells over agents that inhibit the activation of all lymphocytes (e.g. immunosuppressive drugs) or mAbs that target either all CD4+ T cells (e.g. anti-CD4 mAbs), or activated T cells (e.g. activation molecules such as IL-2R).

In contrast to such systemic immunosuppression, a large effort is being directed towards developing specific immunological therapies for specific diseases in individuals with specific ethnic backgrounds. Specific MHC class II haplotypes are known to confer genetic susceptibilities to rheumatoid arthritis and insulin dependent diabetes mellitus. These findings have led many investigators to pursue diagnostic and therapeutic strategies for these diseases by studying the Class II MHC molecules and/or peptide antigens involved. Even in these relatively homogeneous conditions, it may ultimately be necessary to devise unique therapies for individual patients. Further, in contrast to diseases that may be due to common CD4+ T cell-MHC Class II/Antigen interactions, several important idiopathic inflammatory diseases such as psoriasis, systemic lupus and inflammatory osteoarthritis have less clear associations with MHC Class II haplotypes yet share with RA and diabetes the key pathogenic feature of early CD4+ T cell infiltration. The advantage of pursuing therapeutic strategies that target the CD4+ T cell, such as anti-T-BAM therapy, is largely due to the fact that it would not necessary to identify the relevant MHC molecules or antigens in order to modulate the inflammatory response. Indeed strategies, such as mAb 5c8 therapy, that target exclusively those activated CD4+ T cells in diseased tissues, may harness the cognitive functions of each individual's immune system to select T cells for elimination or functional modulation. To examine these questions, we propose the following studies:

Methods

The proposed research aims rely heavily on the ability of the investigators to obtain clinical specimens from patients with a wide variety of immunologic diseases undergoing surgery or biopsy. The P.I.'s are in an ideal position to obtain such specimens, in fact, our preliminary studies demonstrate this ability. The P.I.'s are members of the division of Rheumatology in the Department of Medicine and both the investigators actively care for patients with autoimmune diseases in the Edward Daniels Arthritis Clinic at Presbyterian hospital. In addition, we have ongoing collaborative interactions with several members of the Department of Orthopedic Surgery who provide us with joint specimens. Therefore, the P.I.'s are well positioned to obtain relevant clinical specimens to pursue the evaluation of mAb 5c8 on in vitro functions of lymphocytes from the peripheral blood and joint tissues from individuals with autoimmune disease and osteoarthritis. Further, Dr. Alessandra Pernis is a member of our research team and in addition is an active clinical fellow in the Division of Allergy and Immunology. Dr. Pernis will assist us in the identification and accession of clinical specimens from individuals suffering from allergic disorders. In addition, we are investigators on Dr. Leonard Chess's Institutional Review Board Approved Protocol, "Immunological studies in man" which permits us to obtain lymphocytes from such individuals. In addition to our studies on arthritic diseases, in association with Dr. Janet Prystowsky, Department of Dermatology, we have recently won approval of a protocol to study psoriasis, "Analysis of Cutaneous T Lymphocytes in Psoriasis and Other Dermatologic Diseases".

1. Characterization of T-BAM Expression in Diseased Tissues

To further analyze the role of T-BAM in inflammatory, autoimmune and allergic conditions, the immunohistochemistic analysis of diseased tissue will be extended to study the localization of T-BAM on snap-frozen tissue specimens in additional cases of rheumatoid and osteoarthritis and psoriasis at various stages of disease activity and progression. In addition, these analyses will be extended to cases of systemic lupus, allergic asthma, diabetic pancreas, inflammatory bowel disease and transplanted organs. These analyses will attempt to correlate patterns of expression of particular surface structures, such as T-BAM, CD4 and a variety of other lymphocyte surface molecules with diseases and disease activity.

2. Evaluate the Effects of mAb 5c8 on in Vitro Systems of Lymphocyte Function Using Cells from Individuals with Inflammatory, Autoimmune and Allergic Disorders It is currently unclear If the T-BAM+CD4+ T cells infiltrating the tissues from inflammatory disease patients play roles in mediating key pathophysiological events in these diseases. Certain diseases have pathological immunological activity that can be studied in vitro. Therefore, lymphocytes from the peripheral blood and inflamed tissues from individuals with rheumatoid arthritis, systemic lupus and allergic conditions such as allergic asthma will be isolated. The in vitro studies will address whether the mAb 5c8 inhibits rheumatoid factor (IgM ant-TgG) in rheumatoid arthritis, anti-DNA antibody production in systemic lupus, or IgE production in allergy. In these studies T and B cells from peripheral blood or affected tissues will be isolated, co-cultured in the presence of growth factors and in the presence of 5c8 or control mAbs and the production of autoantibodies or IgE will be measured by specific ELISAs.

3. Evaluate the Effect of mAb 5c8 on the Function of T Lymphocytes from Non-human Primates (rhesus macaques) in Order to Eventually Conduct Safely and Pharmacokinetic Studies in Such Animals The interaction of mAb 5c8 with rhesus macaque lymphocytes was studied (under the protocol of Dr. Michael Ferin of the Department of Reproductive Biology and OB/GYN) and it was found that mAb 5c8 reacts with the T-BAM homologue on Rhesus macaques. Future studies will address whether mAb 5c8 blocks the functions of CD4+ T cells from macaques in order to determine if rhesus is a suitable animal model to ultimately study in vivo administration of mAb 5c8 (which is outside of the present proposal) The functional studies of rhesus lymphocytes and the effect of 7ib 5c8 on these functions will closely parallel functional studies that we have already performed on human lymphocyte subpopulations.

4. Evaluate the Potential Use of mAb 5c8 as a Diagnostic Modality in the Clinical Evaluation of Leukemia/lymphoma In collaboration with Dr. Giorgio Inghiram and Dr. Daniel Knowles, Department of Pathology, the expression of T-BAM on over 100 cases of leukemia/lymphoma was studied. Approximately 30% of T cell lymphomas express T-BAM in frozen sections of lymph nodes. It is currently unknown if leukemic T cells in peripheral blood express T-BAM in such cases. Therefore, we will study peripheral blood of leukemia cases to determine if T-BAM expression is present and what relationship peripheral T-BAM expression has with lymph node T-BAM expression. These studies may reveal that mAb 5c8 is a useful diagnostic antibody in the evaluation of individuals with leukemia. In addition, these studies may justify therapeutic trials with mAb 5c8 in the treatment of such neoplasms.

Future Extensions

Future studies will depend on the results of the proposed preliminary pre-clinical research. The results of the immunohistochemical studies will focus our attention on a certain set of diseases. The in vitro studies may justify clinical studies on certain subset of such diseases. In the event that the preliminary studies justify clinical trials we will perform animal studies on non-human primates because it is known that mAb 5c8 reacts wish T-BAM homologue on Rhesus macaque activated T cells (see above). The animal studies will be designed to determine toxicity and pharmacokinetic profiles of mAb 5c8, as well as to test the hypothesis that depletion of T-BAM expressing cells will be transient and that T-BAM expressing cells will be replaced from the circulating pool of resting T cells. This question will specifically be tested by studying lymph node biopsies of normal animals by immunohistochemistry before and after mAb 5c8 treatment. Finally the role of 5c8 in inhibiting immune responses in vivo will be tested by immunizing animals in the presence and absence of 5c8 treatment and evaluation of the antibody and skin test responses of study animals. To perform such experiments we will need separate IRB approval for these studies because they are not addressed in our current protocols. However, to obtain such approval it will be important to obtain 5c8 in a form that is suitable for such studies and the expense of obtaining such a reagent is part of the current proposal's budget.

These studies may indicate that the current form of the mAb 5c8 (murine IgG2a-human complement fixing) is not optimal to obtain the desired specific modulation of CD4+ T cell function. In this event, it may be necessary to genetically modify the mAb 5c8 in order to alter the Fc region of the antibody that determines its complement binding function and/or tissue targeting. This could take the form of changing the Fc region of the antibody to a human Fc region, or to alter the combining site of the antibody to closely resemble human antibodies, a process termed, "humanization" which is a technology that the principal investigator has significant experience, having radically altered human antibodies to contain amino acid sequences of the CD4 molecule (unpublished). In addition to altering the functional properties of the antibody to contain different effector functions of normal antibodies, it may be desirable to genetically affix a toxin to the Fc region of the mAb 5c8, which is a relatively common approach that has been utilized by several of the companies with which we are currently negotiating.

The successful completion of animal studies will be followed by clinical phase I studies of human subjects to determine the safety and pharmacokinetic profiles of mAb 5c8 in humans.

Fourth Series of Experiments

Isolation of a cDNA Encoding T-BAM, a Surface Glycoprotein on CD4+ T Cells Mediating Contact-dependent Helper Function for B Cells: a New Member of the TNFα Gene Superfamily T-BAM is an activation-induced surface protein on CD4+ T cells that mediates a contact dependent signal for B cell differentiation and IgG secretion. T-BAM was identified by the mAb 5c8 which binds T-BAM on a functionally unique Jurkat subclone D1.1 that constitutively expresses surface T-BAM. In this series of experiments, T-BAM's structure is defined. T-BAM protein was purified from D1.1 cell lysates by affinity chromatography using the mAb 5c8. he $NH_2$-terminal amino acid sequence of isolated T-BAM protein was determined by automated microsequencing and this sequence was used to design a degenerate oligonucleotide probe (T-BAM.2). In the antisense orientation, the oligonucleotide probe recognized a 2 kB mRNA species isolated from T-BAM expressing D1.1 cells, but not mRNA isolated from control, non-helper Jurkat cells, B2.7 that do not express T-BAM. The $NH_2$-terminal sequence was found to be related to that of a type-II murine T cell surface molecule of related function, CD40-L. RNA-PCR of D1.1 mRNA amplified a fragment of DNA that is homologous in size and sequence to the corresponding region of murine CD40-L, a region that encodes the cytoplasmic and membrane proximal portions of the molecule. This fragment which is about 330 bp was subcloned and used to probe a D1.1 cDNA library in λgt-11. Nine clones containing a 1.8–2.2 kB inserts were obtained.

Sequence analysis of the clone revealed a type II surface membrane glycoprotein with homology to the murine CD40-L, a molecule on activated murine T cells that drives IgE secretion. Both of these proteins are members of a TNFα superfamily that includes cytokines and cell surface effector molecules of a wide variety of immunological and other functions. In addition to T-BAM and CD40-L, the existence of at least one other related molecule is suggested by Southern analysis of human DNA using a T-BAM probe. Although they are functional distinct, it is still a possibility that CD40-L and T-BAM may be homologue, in which case, two novel molecules that relate to T-BAM then exist.

Introduction

Progress in the elucidation of contact dependent signals was achieved by the recent identification of a functionally unique subclone of the Jurkat T cell leukemia line, D1.1, that constitutively activates resting peripheral B cells (Yellin, et al., 1991). The D1.1 clone has previously been shown to induce resting B cells to express surface CD23 molecules, drive B cells to proliferate, and induce B cells to differentiate into Ab forming cells (Yellin, et al., 1991). The B cell activating capacity of D1.1 was localized to the cell surface, because paraformaldehyde fixed D1.1 retained the capacity to activate B cells, but D1.1 supernatants were inactive (Yellin, et al., 1991). Together, these data, suggested that D1.1 shared surface structures with activated T cells that mediate contact dependent helper function.

In a previous series of experiments, one such structure termed T-BAM (5c8 Ag) was identified by screening hybridomas for mAbs which react specifically with D1.1 and which inhibit the functional activation of B cells by D1.1 (Lederman, et al., 1992). The mAb 5c8 identified a novel 30 kDa structure that was expressed on activated CD4+ T cells, but not CD8+ T cells, B cells or monocytes (Lederman, et al., 1992). The kinetics of cell surface expression of T-BAM after PHA and PMA stimulation are relatively unique in that maximal expression occurs after 6 h, but is followed by down-regulation that results in baseline (no) expression by 24 h (Lederman, et al., 1992). In functional assays, the anti-T-BAM mAb 5c8 inhibits the ability of normal CD4+ T cells to drive B cell differentiation into antibody forming cells (Lederman, et al., 1992). In addition, the T-BAM expressing lymphoma T cell, Jurkat D1.1, activates B cells from lymphoid organs, as well as a B cell lymphoma clone, RAMOS 266 (Siegel, et al., 1990), in a manner that is inhibited by anti-T-BAM (mAb 5c8) and is similar to the effect we have previously described for peripheral B cells. In vivo, T-BAM is expressed by T cells predominantly in the mantle and centrocytic zones of lymph nodes which are the anatomic sites of T cell interactions with B cells (Lederman, et al. 1992). Taken together, these data demonstrate that the T-BAM is one component of the surface structures on CD4+ T cells that mediate contact dependent helper function.

The T-BAM-specific effect on B cells was found to be blocked by mAbs against CD40 and not several other B cell molecules thought to play roles in receiving contact dependent signals in lymphoid tissue. The CD40 molecule on human B cell surfaces has interesting signalling functions relevant to lymph node B cell differentiation (Clark, et al., 1986; Clark, et al., 1988; Ledbetter, et al., 1987; Ledbetter, et al., 1986) because anti-CD40 (mAb G28-5 (Clark, et al., 1986)) prevents programmed, germinal center B cell death (apoptosis) (Liu, et al., 1989) and has been shown to induce proliferation, differentiation and long term growth of human B cells (Banchereau, et al., 1991a; Banchereau, et al., 1991b). The effect of anti-CD40 mAbs on T-BAM specific help did not result from a general inhibition of B cell responsiveness, because the effect of anti-CD40 on CD23 expression was found to be additive with submaximal doses of rIL-4. In addition, mAbs to CD40 appeared to mimic the effect of D1.1 when presented on Fc receptors on a layer of transfected murine fibroblasts. Taken together these findings were consistent with the notion that T-BAM and CD40 may interact with each other, possibly an a receptor-counter-receptor relationship.

Subsequently a murine ligand for the CD40 molecule has been identified by expression cloning of a murine cDNA library using a chimeric human-CD40-Ig chain molecule. The CD40-L cDNA encodes a 33 kDa type-II surface membrane protein (Armitage, et al., 1992). Although initially reported as a novel gene, subsequent analysis by our lab (unpublished) and by the authors revealed that CD40-L is related to tnfα (Farrah, et al., 1992). The idea that Ct40-L is homologous to tnfα gas of interest, given that their receptors, tnfα RI and II are related to CD40. The binding interaction of CD40-L with CD40, taken together with the functional evidence linking T-BAM with CD40 specific signalling suggests that T-BAM and CD40-L may be related molecules. Further, the relatedness of 0D40-L and T-BAM is suggested both by their related functions in 3 cell triggering and by their similar apparent molecular weights. However, the precise relationship of CD40-L to T-BAM remains unknown.

Therefore in this series of experiments, the structure of T-BAM was examined and a PCR fragment and a partial cDNA were isolated and found to encode a type-II surface membrane protein with significant homology to CD40-L (Armitage, et al., 1992). Although the functional evidence suggest that T-BAM and CD40-L are distinct. The possibility still exist that T-BAM is the human homologue of CD40-L. In addition to T-BAM and CD40-L, the existence of at one other related member of this family is suggested by Southern blot analysis of human genomic DNA using a T-BAM probe. In the event that T-BAM and CD40-L are found to be homologue, the Southern data suggest that two other members of such form may exist. The structural information sheds light on several molecular aspects of T-helper function and suggests that at least two molecules on T cells direct different B cell responses in interactions that both involve the signalling via the CD40 molecule.

Materials and Methods
Cell Lines

The Jurkat clones D1.1 L and B2.7 have been described (Yellin, et al., 1991; Lederman, et al., 1992).

Isolation of T-BAM Peptide

To obtain purified T-BAM protein, Jurkat D1.1 cells were grown in Iscove's Modified Dulbecco Medium (GIBCO®) in 10% Fetal Bovine Serum (Hyclone) in both a "cell factory" (NUNC) and 10 flasks (600 ml flasks). Combined, these cultures harvested $14 \times 10^9$ cells. Cell pellets were lysed in 125 ml of ice cold lysis buffer (1% NP40, 15 mM tris, 15 mM NaCl, 10 µg/ml phenylmethyl sulfonyl fluoride (PMSF), 5 mM EDTA, 10 µg/ml iodoacetamide (IAA)). The lysates were vortexed and mixed for 1 hr on a rotary shaker before centriguation at 7000 rpm for 20 min to pellet insoluble material. The lysate supernatant was then filtered sequentially through 0.45 and 0.2 m filters (Nalgene). The filtered lysate (80 ml) was diluted 1:1 with 0.1 M bicarbonate buffer (0.5 M NaCl, pH 8.3) before affinity chromatography.

Purification of T-BAM by Affinity Chromatography

The mAbs 5c8 and OKT4 were purified on protein G columns (Pharmacia). The purified mAbs were covalently linked to CNBr activated sepharose 4B beads (Pharmacia, Uppsala, Sweden) by incubation of mAb (3.88 mg/2 ml of 5c8 and 3.0 mg/1.5 ml of OKT4) in binding buffer (0.25 M bicarb buffer, 0.5 M NaCl, pH 8.75) with 0.142 gram of beads for each mAb. The mAb solutions were reacted with beads for 3 h at r.t. and quenched in 0.2 M Tris, pH 8.0 for 3 h. The mAb coated bead were used to make 0.5 ml gel in short columns (Schleicher and Schuell) and washed alternatively with bicarb binding buffer and elution buffer (0.1 M acetate buffer, 0.5 M NaCl, pF 4.0).

To purify T-BAM, D1.1 lysates were pre-cleared by passage through the OKT4 column, before passage through the 5c8 column. After the lysate had passed through both columns, the mAb 5c8 column was washed with 200 ml of bicarb buffer before elution with 0.1 M acetate, pH 4.0 into 0.5 ml fractions in 15 ml conical polypropylene tubes (Sarstadt, Princeton, N.J.). The protein in each fraction was precipitated with approximately 5 ml of $-20°$ acetone overnight. The precipitate was then collected by centrifugation at 3000 G and air-dried.

$NH_2$-terminal Sequencing of T-BAM Peptide

The acetone precipitates from each column fraction was resuspended in 60 ml of gel loading buffer (BioRad instructions), loaded onto a 20 cm 12.5% SDS-PAGE gel in a BioRad vertical electrophoresis apparatus and subjected to 100 V for approximately 6 h and then transferred to Problott PVDF paper (Advanced Biosystems, Seattle Wash.) in CAPS buffer for 90 minutes at 70 volts in a Biorad Trans-Blot apparatus. Transfer was optimized using the prestained protein standards (Low M.W. and High M.W. standards (Biorad, Rockville Center, N.Y.).

After transfer, protein bands were stained with comassie blue R-450 and the membrane was air dried. A 31 kD band (p31K), corresponding to the relative migration of T-BAM was excised with a razor blade and subjected to 20 cycles of sequencing on an Applied Biosystems 470A gas phase sequencer/120A PTH analyzer by Dr. Mary-Ann Gavinovitch, of the Protein Core Facility, Howard Hughes Medical Institute, Columbia University (Sequence #S01220, Apr. 28, 1992). The $NH_2$-terminal sequence determined was (M)IE(T)YNQ(Q)SP(PXAAS) (SEQ ID No. 11).

cDNA Library Construction and Screening

D1.1 poly A RNA was isolated by FAST-TRACK (Invitrogen) and an oligo-dT primed λ-gt11 library was generated containing approximately $4 \times 10^6$ independent clones using λ arms from Strategene (San Diego, Calif.) by the Pharmacia protocol.

From an amplified library, approximately $1 \times 10^6$ plaques were screened, 8 independent clones were identified and each plaque was purified 4 rounds of cloning on YT1090 (Invitrogen, San Diego, Calif.).

Oligo Synthesis

The following oligodeoxynuclotides were synthesized on an Applied Biosystems DNA Synthesizer Model 380B by the Protein Chemistry Core Facility of the Howard Hughes Medical Institute/Columbia University.

TBAM.1 (17mer) 5'-AT(A/C/T) GA(A/G) AC(A/G/C/T) TA(C/T) AA(C/T) CA-3' (SEQ ID No. 1)
TBAM.2 (20 mer) 5'-ATG AT(A/C/T) GA(A/G) AC(A/G/C/T) TA(C/T) AA(C/T) CA-3' (SEQ ID No. 2)
TBAM.2 antisense (20 mer) 5'-TG(G/A) TT(G/A) TAI GT(C/T) TC(T/G/A) ATC AT-3' (SEQ ID No. 3)
CD40L(11–31) 5'-GCA TGA TAG AAA CAT ACA GCC AAC-3' (SEQ ID No. 4)
CD40L(54–75) 5'-AAC TGG ACT TCC AGC GAG CAT G-3' (SEQ ID No. 5)
CD40L(369–348) 5'-GGA TCC TCA TCA CCT CTT TGC-3' (SEQ ID No. 6)
CD40L(389–368) 5'-ACA ACG TGT GCT GCA ATT TGA GG-3' (SEQ ID No. 7)
λ gt11-rev (24 mer) 5'-TGA CAC CAG ACC AAC TGG TAA TGG-3' (SEQ ID No. 8)
Mu12/T-BAM.2 5'-CTT TCA GTC AGC .T-BAM-3' (SEQ ID No. 12)

RNA Polymerase Chain Reaction

Poly-$A^+$ RNA was isolated from $5 \times 10^8$ D1.1 cells and cDNA was prepared by reverse transcription of approximately 1.0 µg of total RNA using 200 units of moloney murine leukemia virus (MMLV) reverse transcriptase (Bethesda Research Labs (BRL®), Bethesda, Md.) for 30 min at 42° C. in a reaction containing 5 pM of the primer CD40L (369–348) in 20 ml of a buffer containing 50 mM Tris-HCL, pH 8.3, 75 mM KCl, 3 mM $MgCl_2$, 10 mM DTT and 20 units of RNAsin (Pharmacia®). The reaction was heated to 95° C. for 5 min to inactivate the enzyme. The first strand was amplified by PCR under the following conditions: the initial template denatureing step (8 min at 94° C.) followed by 30-fold repetitive cycle of 2 min at 55° C. (annealing), 2 min at 72° C. (denaturation) using 2.5 units DNA Taq-polymerase (Perkin-Elmer Cetus, Norwalk, Conn.), 200 mM each of DATP, dCTP, TTP and dGTD (Perkin-Elmer Cetus and 50 pM of the primers CD40L (11–31) and CD40L (369–348) in a final volume of 100 ml PCR buffer (10 mM Tris-HCL, pH 8.3, 50 mM KCL, 1.5 mM MgCl2, 0.001% gelatin). After amplification, the samples were analyzed by electrophoresis or a 1.0% agarose gel and were stained with ethidium bromide.

Subcloning

Bluescript/p3.1 was generated by blunt end ligation of PCR products into EcoR5 digested Bluescript (Promega). Bluescript/p5-1 was generated by ligation of overnight EcoR1 digests of the λgt-11 phage DNA maxipreps into EcoR1 digested Bluescript 11 SK+ (Promega), that had been previously treated with calf-intestinal phosphatase. Ligations into Bluescript were performed with T4 DNA ligase into competent *E. Coli* and grown on ampicillin (25 µg/ml) plates.

Screening of λgt-11 Libraries

PCR generated probes were radiolabelled by the random hexamer method and used to screen λgt-11 plaques.

DNA Sequencing

DNA sequencing was performed on an automated DNA sequencer, Applied Biosystems by the Columbia University Comprehensive Cancer Center Core Facility.

Transfection of 293 Cells $2 \times 10^6$ 293 cells will be plated on 100 mm Petri dishes 48 hr prior to transfection. The cells will be fed with fresh medium 1 hr prior to transfection. Calcium phosphate precipitates will be prepared using 20 mg of plasmid DNA per dish. After 15 hr at 37° C. in 5% $CO_2$ the cells will be fed with fresh media. Thirty six hours after transfection, the cells will be harvested by treating with trypsin-EDTA (Gibco, Grand Island, N.Y.) for 30 sec and examined by FACS.

Monoclonal Antibodies

The mAb 5c8 (IgG2a) has been described (Lederman, et al., 1992). The mAb 5c8 has been described. The mAb OKT4(anti-CD4) is available from the American Type Culture Collection (Manassas, Va.). All mAbs were purified from ascites fluid on protein A (Biorad, Rockville Center, N.Y.) or protein G columns (Pharmacia, Upsula, Sweden).

Results

T-BAM is an activation-induced surface protein on CD4+ T cells that mediates a contact dependent signal for B cell differentiation and IgG secretion. T-BAM was identified by the mAb 5c8 which binds T-BAM on a functionally unique Jurkat subclone D1.1 that constitutively expresses T-BAM. In the present report, the T-BAM's structure was studies by protein chemistry and by isolation of cDNA that encodes T-BAM.

T-BAM protein was purified by affinity chromatography using the mAb 5c8 to affinity purify T-BAM protein from D1.1 cell lysates. The $NH_2$-terminal amino acid sequence of isolated T-BAM protein was determined by automated microsequencing and this sequence was used to design a degenerate oligonucleotide probe (T-BAM.2). In the antisense orientation, the end-labelled degenerate oligonucleotide probe was used to probe Northern blots from T-BAM+ D1.1 cells as well a the control, T-BAM− Jurkat B2.7 cell line. The anti-sense probe hybridized with an approximately 2 kB mRNA species specifically in the T-BAM expressing D1.1 cells, but not mRNA isolated from T-BAM− control, non-helper Jurkat cells, B2.7.

At this time the sequence of a ligand for the murine CD40 molecules was published by Armitage et. al (1992). It is noted that this molecule had related function and interestingly had a highly homologous $NH_2$-terminal sequence. The comparison of the two sequences are shown below:

```
T-BAM    (M)IE(T)YNQ(Q)SP(PXAAS)    (SEQ ID No. 9)
          *  ** *  *  **    *
          *  ** *  ***     **    ***
CD40-L    M  IE T  YSQ P  SP RSVAT    (SEQ ID No. 10)
```

Although initial approach to cloning T-BAM involved the use of a degenerate oligonuclotide (T-BAM.2) to screen a D1.1 cDNA library in λgt-11, the sequence relationship of T-BAM and CD40-L suggested the possibility that their sequence relationship could be utilized to generate a longer, double stranded DNA probe. In support of this notion that the $NH_2$-terminus of CD40-L encodes the cytoplasmic tail of a type-II integral membrane protein, and that by analogy, the highly homologous $NH_2$-terminus of T-BAM might be a cytoplasmic tail that is highly conserved between isoforms of related proteins.

Therefore, the next series of experiments addressed if a pair of oligonucleotide probes derived from the murine sequence of CD40L cDNA (from the cytoplasmic and membrane proximal regions) might amplify a homologous sequence of T-BAM cDNA. Therefore, RNA-PCR of mRNA from D1.1 was performed by first synthesizing cDNA primed with CD40L (369–348) and then amplified with the primers; CD40L(11–31) and CD40L(369–348). This reaction amplified an approximately 330 bp fragment from D1.1 RNA. The PCR product was subcloned by blunt end ligation into Bluescript and of four inserts sequenced in one direction, a clone, p3-1/Bluescript SK+ was identified that was a 330 kB insert, which was approximately 85% homologous to the murine CD40-L.

Plasmid p3-1/Bluescript II SK+ was deposited on Nov. 16, 1992 with the American Type Culture Collection (ATCC), 10801 University Blvd., Manassas, Va. 20110-2209, U.S.A. under the provisions of the Budapest Treaty for the International Recognition of the Deposit of Microorganisms for the Purposes of Patent Procedure. Plasmid p3-1/Bluescript II SK+ was accorded ATCC Accession Number ( ).

The comparison of the CD40-L sequence and the amplified PCR product, p3-1, is shown below:

```
CD40-L    57  TGGACTTCC.AGCGAGCAT.GAAGATTTTA.TGTATTTACTTAC..TGT  101
              |||||||||| | |||||| | ||| ||||||| |||||||||||| | |||
p3-1     436  TGGACTTCCAACCGANCTTGGAAAATTTTTATTGTATTTACNTTCCTTGT  387
```

-continued

```
102 TTTCCTTAT...CACCCAAATGATTGGATC.TGTGCTTTTTGCTGTGTAT 147
    |||||||||   | || | ||||||||||| |  |||||||||||||||
386 TTTTCTTATCCACCCCAAGATGATTGGGTCAAGCACTTTTTNCTGTGTAT 337

148 CTTCATA..GAAGATTGGATAAGGTCGAAGAGGAAGTAAACCTTCA.TGA 194
    |||||||   || |||||| ||| | |||||| |||   || |||||| |||
336 CTTCATAAGAAGGGTTGGACAAGATAGAAGATGAAAGGAATCTTCATTGA 287

195 AGATTTTGTATTCATAAAAAAGCTAAAGAGATGCAACAAAGGAGAAGGAT 244
    ||||||||||||||| |||| | || ||||||||||||| |||||||| |||
286 AGATTTTGTATTCATGAAAACGATACAGAGATGCAACACAGGAGAAAGAT 237

245 .CTTTATCCTTGCTGAACTGTGAGGAGATGAGAAGGCAATTTGAAGACCT 293
     | ||||||||| |||||||||||||||||| | ||| || ||||||||| | |
236 CCCTTATCCTTACTGAACTGTGAGGAGATTAAAAGCCAGTTTGAAGGCTT 187

294 TGTCAAGGATATAACGTTAAACAAAGAAGA...GAAAAAAGAAAACAGCT 340
    ||| |||||||||||| |||||||||||||| ||   ||| ||||||||||||||
186 TGTGAAGGATATAATGTTAAACAAAGAGGAGACGAAGAAAGAAAACAGCT 137

341 TTGAAATGCAAAGAGGTGATGAGGATCC.TCAAATTGCAGCA 381 (SEQ ID No.13)
    |||||||| |||||||||||||||||||||||| ||||||||| | |||
136 TTGAAATNCAAAGAGGTGATGAGGATCCATCGAATTCCTGCA  95 (SEQ ID No.14)
```

Furthermore, on Northern analysts comparing RNA from D1.1, the T-BAM− Jurkat clone, B2.7 and control RNA from the RAMOS B cell line, the p3.1 probe hybridized to a 2 kB mRNA species exclusively in the D1.1 cell line. Taken together with the Northern analysis of the anti-sense T-BAM.2 probe and with the protein data that T-BAM is expressed exclusively in D1.1, but not B2.7 Jurkat cells, these data suggested that the 330 bp insert might be derived from T-BAM cDNA.

Therefore, this approximately 330 bp insert was used as a probe to screen λgt-11 clones from D1.1 cDNA library. Such screening with the 330 bp insert as a random hexamer labelled probe identified 9 independent λgt-11 clones containing inserts that ranged in size from 1.8 to 2.4 kB.

PCR of the phage DNA were performed using probes that hybridize to regions of the phage DNA that flank the insert were performed and revealed that the clones contained inserts in the range of 1.8–2.1 kB in size. Given the observation that the size of the mRNA of T-BAM, using the anti-sense oligo derived from the $NH_2$-terminal sequence by Northern analysis was approximately 2 kB, it is likely that the largest of these clones represents either a full length cDNA or a nearly full length cDNA of the mRNA that encodes T-BAM.

In each of the nine clones, liberating the EcoR1 insert (by digestion with EcoR1) revealed that all eight inserts contained an internal EcoR1 site, because two fragments were obtained in all cases. In the case of λgt-11 clone 1-1b (which had the longest, 2.1 kB insert by PCR), the two EcoR1 fragments generated were 1.3 kB and 0.8 kB. These two fragments were cloned into EcoR1 digested. Calf intestinal phosphatase treated-Bluescript II SK+, generating p1-1b(1.3 kB)/Bluescript II SK+ and p1-1b (0.8 kB)/Bluescript II SK+.

Plasmids p1-1b (1.3 kB)/Bluescript II SK+ and p1-1b (0.8 kB)/Bluescript II SK+ were deposited on Nov. 13, 1992 with the American Type Culture Collection (ATCC); 10801 University Blvd., Manassas, Va. 20110-2209, U.S.A. under the provisions of the Budapest Treaty for the International Recognition of the Deposit of Microorganisms for the Purposes of Patent Procedure. Plasmid p1-1b (1.3 kB)/Bluescript II SK+ was accorded ATCC Accession Number ( ) and plasmid p1-1b (0.8 kB)/Bluescript II SK+ was accorded with ATCC Accession Number ( ).

Partial DNA sequence of the 0.8 kB insert revealed it has significant overlap approximately, 150 bp with the cloned PCR product p3-1. The comparison is shown below:

```
p1-1b(0.8 kB)    2 tgcaacacaggagaaagat.ccttatccttactgcaactgtgaggagatt   50
                   |||||||||||||||||||| |||||||||||||| |||||||||||||||
p3-1           546 TGCAACACAGGAGAAAGATCCCTTATCCTTACTG.AACTGTGAGGAGATT  594 p1-1b(0.8 kB)   51 aaaa 54 (SEQ ID No. 15)
                   ||||
p3-1           595 AAAA 598 (SEQ ID No. 16)
```

In addition, the 5'-terminus of p1-1b(0.8)kB is approximately 200 bp 3'- to the first codon of the mature protein. This gives the orientations of the clones with respect to the full length cDNA as shown below:

```
***********T-BAM cDNA* (bp)*****************************
-- 200 --400 --600 --  800 --1000 --1200 -------/ / --2300
/*p3-1***/
     /******p1-1b (0.8 kB)*****/
                              /**p1-1b(1.3 kB)*/ /*****/
           /                    /
         BstYI                EcoR1
         /***/
    approximately,
    150 bp overlap
/************************/
probable coding sequence for
30 kDa protein (T-BAM)
                    >>>>>>>>>>>>>>
```

This map is based on the assumption that the p1-1b(1.3 kB) is derived from sequences in the 3'-UT (untranslated region) of T-BAM because it is relatively uncommon for messages to have such a long 5'UT region. In additional support of this assumption is the observation that the related cDNA for CD40-L has a similarly sized 3'UT (approximately 1 kB).

Therefore, the full length cDNA may be obtained by the combination of the cloned PCR product (p3-1) and the cloned cDNA (p1-1b(0.8 kB)) which together probably contain the entire coding region of the T-BAM cDNA, given the size of the mature protein (30 kDa) and since the PCR product was derived from the $NH_2$-terminal sequence. In addition, the cloned DNA that we have provided are likely to encode all of the amino acids that would be used in a soluble, recombinant form of the molecule.

For expression of T-BAM, p1-1b(1.3 kB) is probably not necessary since it encodes the 3'-UT region of the dDNA. However, the 3'-UT region of the cDNA is likely to be involved in regulation of T-BAM expression, in analogy to other 3'-UT regions and therefore, p1-1b(1.3) will be important to establish in future studies the role of the 3'UT region in regulatory functions.

In order to generate a clone that directs T-BAM expression, a cloned PCR fragment, similar to p3-1, but in addition, having the murine leader sequence of muCD40-L annealed to by PCR with the primers mul2/T-BAM.2 and 3'T-BAM sequence will be generated. It is expected that the leader sequence to murine CD40-L will be sufficient to permit expression of the T-BAM clone. Such a fragment would encode the NH2-terminal approximately 60 aa which include the (5'-200 bp) fragment missing from p1-1b(0.8) and flank a BstYI site (at about 220) in the overlapping region of p1-1b(0.8) and the PCR product. If this BstYI site does not appear to be unique after restriction mapping (and sequencing) of the both fragments, then other sites exist nearby.

Once the full length clone is ligated into such an expression vector, it can be transiently transfected into a fibroblast cell line (such as 293 cells) and then assayed for T-BAM expression by FACS. Further, T-BAM expressing fibroblasts can e cultured with resting human B lymphocytes, or the RAMOS 266 clone and then the B cells can be studied for the induction of surface CD23 expression.

To determine the full length cDNA sequence of T-BAM, ultimately, a new λgt-11 library will be constructed using D1.1 mRNA. The T-BAM cDNA library is primed with an oligonucleotide specific for T-BAM sequence derived from p1-1b(0.8 kB) fragment. This library will be screened with the insert from p3-1 to obtain λgt11 clone that encodes the 5' region of the T-BAM cDNA. The DNA sequences of this new insert plus those from p1-1b(0.8 kB) and p1-1b(1.3 kB) will be determined. Analysis of the new sequence 5' cDNA should reveal that the $NH_2$-terminal peptide sequence.

The structure of the full length insert including p1-1b(1.3) kB can also be determined by performing PCR of the λgt-11 DNA of clone 1-1b, following by blunt end cloning of this fragment into Bluescript. The DNA sequence of the full length sequence of this cloned PCR fragment will be determined. Comparison of this sequence to that of the 1.3 and 0.8 kB inserts of p1-1b(1.3 kB) and p1-1b(0.8 kB) will facilitate the determination of their correct 5'-3' orientation of p1-1b (1.3 kB). In order to generate a full length cDNA clone from these fragments, the 1.3 kB insert will be liberated by EcoR1 digestion of the p1-1b (1.3kB)/Bluescript II SK+ clone and gel purified. Next, partial EcoR1 digestion of the p1-1b (0.8 kB)/Bluescript II SK+ plasmid will be performed and the linearized forms will be gel purified. Then the 1.3 kB EcoR1 insert will be ligated into the partially digested (linearized) p1-1b (0.8 kB)/Bluescript SK+ plasmid and transform competent bacteria. The detailed restriction maps of clones from this transformation will allow identification of a full length cDNA insert that has ligated the 1.3 and 0.8 kB inserts together in the

```
******************T-BAM cDNA (bp)**********************
-15 -- 0 --+15 -- 30 --/ /----------------220-------260
***************                         /     ********
12 bp - T-BAM.2                         /  PCR primer#2
mul2/T-BAM.2 leader                        BstYI
```

This fragment will then be ligated to p1-1b(0.8 kB) by digestion of p1-1b(0.8 kB) with BstyI and digestion of the PCR fragment with BstYI and EcoR5 for directional (blunt end) cloning. The resulting insert (containing the 15 bp murine leader-200 bp PCR fragment—and 600 bp BstYI/p1-1b(0.8 kB) fragment will be directionally cloned from an intermediate vector into an expression vector to drive T-BAM protein synthesis.

correct orientations. This full length insert (pT-BAM/Bluescript II SK+) will then be sequenced that confirm that it contains the two inserts in the correct orientation. The poly-linker on Bluescript will then allow us to directionally clone these fragments into a eukaryotic expression vector, such as pCDNA-1. This pCDNA-1/pT-BAM, will then be transfected into fibroblasts, such as 293 cells and which can be studied for expression of surface T-BAM protein.

There may be unforeseen problems in expressing this clone. There are cases in which some of the 5' or 3' untranslated sequences will be removed to permit expression. These can be readily accomplished using the sequence information obtained. In addition, there are rare cases in which a cDNA clone such as pT-BAM/pCDNA-1 may have errors in sequence stemming from the original generation of the library (typically the reverse transcriptase reaction). In this case, the other eight λgt-11 clones will be studied in a fashion analogous to what described hereinabove and these clones will be reconstructed to generate expression plasmids for T-BAM.

Sequence analysis of the clone has so far revealed a type II surface membrane glycoprotein with homology to the murine CD40-L, a molecule on activated murine T cells that drives IgE secretion. Both of these proteins are members of a TNFα superfamily that includes cyokines and cell surface effector molecules of a wide variety of immunological and other functions.

In order to determine if other, related genes exist, the 330 bp insert of clone p3-1/BluescriptsII SK+ was used to probe a Southern Blot of human DNA (from Hela Cells). Interestingly, three bands were observed. Taken together with the notion that T-BAM and CD40-L are likely to account for two of these bands, these data suggest that at least one other member of this family of "T-helper-effector" molecules exists. Or alternatively, though the functional properties of T-BAM and CD40-L are distinct, the possibility still exist that T-BAM is the human homologue of CD40-L. If T-BAM and CD40-L turn out to be homologues, the Southern data suggest that two other members of such form of helper molecule may exist.

Discussion

In the present work, a PCR product and cDNA clones that together encode T-BAM a cell surface protein on CD4+ T lymphocytes that directs B cell differentiation.

T-BAM was found to be a member of the tnfα gene superfamily. Very significantly, T-BAM is related to the recently identified CD40-L in mouse (Armage, et al., 1992), particularly in the cytoplasmic, transmembrane and stalk regions in which the sequence identity between human T-BAM and murine CD40-L was approximately 85%. These new data suggest that T-BAM and CD40-L are structurally distinct isoforms of B cell-inducing T cell surface molecules, although direct confirmation of such a notion will require the identification of murine and human homologues of both isoforms and in particular sequencing of the coding region in the remainder of the p1-1b (0.8 kB) clone.

Previous data has suggested that T-BAM and CD40-L are related, but functionally distinct. Whereas T-BAM directs IgG synthesis, CD40-L directs the synthesis of IgE (Armitage, et al., 1992). The restriction of T-BAM helper function for IgG has recently been strengthened by the observation that D1.1 in the presence of rIL4 induces an IgM+ clone of the RAMOS B cell lymphoma line to undergo class switching to IgGl, exclusively and not IgE or other isotypes (unpublished). In these experiments, Ramos cells (30 cells per well) were cultured on a feeder layer of 100 mitomycin-C-treated D1.1 cells for two to three weeks and cultured supernatants were studied for Ig secretion by isotype and subclass specific ELISA. Only in the presence of D1.1 cells and rIL-4, Ramos cells differentiated into IgGl secreting cell lines (4/15 in experiment 1 and 19/59 clones in experiment 2). In contrast, B2.7 cell did not induce difffferentiation and isotype switching. Furthermore, recombinant IL-4 was necessary for isotype switching. In addition, no Ramos cells were induced to switch to IgE. These data suggest that T-BAM and CD40 are isoforms of B cell-inducing T cell surface molecules that direct the expression of distinct isotypes of Ig.

It is interesting, in this regard, that mAb anti-CD40 has been shown to induce proliferation, differentiation and polyclonal Ig production that includes all Ig isotypes (Banchereau, et al., 1991a; Banchereau, et al., 1991b). It is further interesting that both molecules appear to have important interactions that involved CD40 molecule on B cells. In the case of CD40-L, CD40-L and CD40 appear to have receptor-co-receptor relationships (Armitage, et al., 1992). In the case of T-BAM, such a relationship is suggested by the reciprocal blockade of their functions by mAbs to the two different structures, however, no direct evidence for a receptor ligand relationship exists. Taken together with their functional differences, these data suggest that CD40-L and T-BAM have distinct functional consequences, despite that fact that both appear to interact with the CD40 molecule on B cells.

In addition to their distinct effects on antibody isotypes, T-BAM and CD40-L have distinctive patterns of expression and requirements for B cell proliferation. The kinetics of cell surface expression of 5c8 Ag after PHA and PMA stimulation are relatively unique in that maximal expression occurs after 6 h, but is followed by down-regulation that results in baseline (no) expression by 24 h (Lederman, et al., 1992). In contrast, CD40-L appears to be prolonged for >72 hours by similar stimuli. Further, T-BAM+ D1.1 cells induce B cell expression only in the context of rIL4 or PHA, whereas CD40-L+ transfectomas induce B cell proliferation in the absence of added cytokines or lectins (Armitage, et al., 1992). Taken together, these data suggested that the signals provided by CD40-L and T-BAM to B cells are distinct, and therefore are consistant with the structural suggestion that these molecules are distinct isoforms with related, but distinct functions.

The CD40 molecule on human B cell surfaces has interesting signalling functions relevant to lymph node B cell differentiation (Clark, et al., 1986; Clark, et al., 1988; Ledbetter, et al., 1987; Ledbetter, et al., 1986) because anti-CD40 (mAb G28-5 (Clark, et al., 1986)) prevents programmed, germinal center B cell death (apoptosis) (Liu, et al., 1989). In this regard, it is interesting that CD40 is homologous to FAS (Itoh, et al., 1991), the T and B cell surface receptor for apoptosis signals. To the extent that T-B interactions in lymphoid organs involve apoptosis, these data suggest that in addition to interacting with CD40 molecules, T-BAM may interact with FAS (Itoh, et al., 1991). In fact, we have recently observed that mAb anti-FAS (Apo-1) (Oehm, et al., 1992; Itoh, et al., 1991) partially inhibits the D1.1 effect on RAMOS 266 and B cell induction of CD23 (unpublished observations). The idea that T-BAM may interact with both CD40 and FAS suggests the idea that CD40 and FAS may be distinct receptor structures, or may form a heterodimeric receptor. Certain of the TNFαR-like molecules are known to exist as multimers—possibly homodimers in the case of CD27 (Camerini, et al., 1991). The interaction of tnfα-like molecules with multimeric receptors is also suggested by the shared trimeric structures of tnf (Hakoshima, et al., 1988; Smith, et al., 1987), and ngf (McDonald, et al., 1991), the only crystallized members of this family. There is evidence that FAS and TNFαR may form heterodimers, because these molecules are co-modulated by anti-FAS antibodies on lymphocyte surfaces (Yonehara, et al., 1989). The fact that a single tnfα-like ligand (CD40) can interact with multiple ligands, including mixed heterodimers of TNFαR-like molecules is also suggested by other examples of tnfα-like molecules. For example, tnfα and tnfβ (lymphotoxin) both react with two distinct chains of TNFαR (I and II) (Goodwin, et al., 1991; Rothe, et al., 1991; Nophar, et al., 1990; Engelmann, et al., 1990; Lewis, et al., 1991; Himmler, et al., 1990; Umtel, et al., 1987; Heller, et al., 1990; Gray, et al., 1990; Smith, et al., 1990; Loetscher, et al., 1990; Dembic, et al., 1990) and in addition, a heterodimeric combination of these chains has been suggested by biochemical analysis (Nophar, et al., 1990; Engelmann, et al., 1990). Together, these observations suggest that members of the tnfα and TNFαR families, may generally interact with combinations of related receptors in order to signal B cells in distinctive ways. Another property that seems to be a shared feature of members of the tnfα family is that TNFαR, CD40 and FAS (Watanabe, et al., 1992) are all receptors for apoptosis signals.

The many examples of tnfα-like and TFNαR-like interactions that operate between T and B cells are shown in the below Table 6. With respect to the properties and functions of tnfα-like molecules, the precise function CD38 (Jackson, et al., 1990) is not known and although ngf has effects on B cell differentiation (Kimata, et al., 1991; Otten, et al., 1989) has been reported, the role of ngf-NGFR (Sehgal, et al., 1989; Chao, et al., 1986; Johnson, et al., 1986) interactions in B cell physiology are not currently understood. Among the TNFαR-like molecules, the functions of CD27 and Ox40 are currently unknown, but it is of interest that CD27 (Camerini, et al., 1991) is expressed as two forms and Ox40 (Mallett, et al., 1990) expression is restricted to CD4+ and not CD8+ T cells. Both of these molecules are induced by T cell activation. The physiological roles of the "Hodgkin's antigen" CD30 (Durkop, et al., 1992) are currently unknown.

TABLE 6

Cell Surface Interactions Involving Members of the tnfα - tnfαR families on T and B cells

| T cells | B cells |
|---|---|
| "help receptors" | |
| T-BAM (help IgG) | CD40/"x" |
| CD40-L (help IgE) | CD40/"y" |
| "apoptosis mediators/receptors" | |
| tnfα (cell surface) | TNFαRI/TNFαRI |
| tnfα (soluble) | TNFαRII/TNFαRII |
|  | TNFαRI/TNFαRII |
|  | sTNFαRI |
|  | sTNFRII |
| tnfβ (lymphotoxin) | TNFαR |
|  | others? |
| ***************************************************** | |
| tnfαR | tnfα |
| (2 isoforms) |  |
| ?FAS/FAS | ? |
| ?FAS/tnfαR | ? |
| ? | FAS/FAS |
| ? | FAS/tnfαR |
| surface molecules of unknown function | |
| CD27/CD27 | ? |
| CD27/CD27a | ? |
| sCD27 | ? |
| ? | CD27/CD27 |
| Ox-40 (rat, mouse) | ?? |
| (CD4 + T cell specific) |  |

TABLE 6-continued

Cell Surface Interactions Involving Members of the tnfα - tnfαR families on T and B cells

| T cells | B cells |
|---|---|
| ***************************************************** | |
| CD38 (OKT10) | ?? |
| (activation induced) |  |
| ngf | NGFR |
| ? | CD30 (Hodgkin's Assoc.Ag) |

An interesting feature of several members of the tnfα family is that proteolytic cleavage of the pro-cytokine surface form of tnfα generates the soluble cytokine form of tnfα. Future studies will determine if T-BAM is cleaved by proteases and what role soluble T-BAM, if identified, may play in T-B cell interactions. It is also interesting that TNFαRs (Umiel, et al., 1987; Heller, et al., 1990; Gray, et al., 1990) and CD27 (Loenen, et al., 1992; DeJong, et al., 1991) molecules have soluble forms, which suggests that soluble forms of CD40 molecule may exist and might also play roles in T-B interactions.

Additional complexity in the interactions of T cell surface molecules with B cell CD40 is suggested by the recent report of another murine CD40-L that has a considerably larger M.W. than CD40-L (39 kDa vs. 33 kDa.) (Armitage, et al., 1992; Noelle, et al., 1992). However, its precise structure, or relationship to T-BAM or CD40-L are currently unknown.

Although several other B cell surface molecules have been described that may play roles in receiving contact dependent signals in lymphoid tissue. However, the effect of mAb 5c8 in inhibiting D1.1-B cell interactions appears to be relatively-unique among antibodies tested, in that anti-CR2, anti-LFAI, anti-LFA3 or anti-ICAM have no effects on D1.1 interactions with B cells. Therefore, the T-BAM dependent stage of T-B interactions appears to be a discreet step in helper effector function.

The transient nature of T-BAM expression, suggests that it may play a role in stabilizing that T-B "cognate pair".

This physical association of activated peptide-specific CD4+ T cell with a "cognate" native protein-specific B cell appears to be the molecular basis of the physiologically defined, "antigen bridge".

In addition to clarifying the relationship between T-BAM and CD40-L, the availability of a cDNA encoding T-BAM will allow us to identify homologous genes in other species, particularly the mouse in which physiological aspects of T-BAM's functions can be addressed by overexpression (in transgenics) or by targeted gene disruption. In addition, the availability of T-BAM specific cDNA probes will facilitate the analysis of the regulation of T-BAM expression at the transcriptional level, as well as providing a means to study by genetic manipulations, the structural determinants of T-BAM's functional properties.

In addition to their roles in immune physiology, certain of the TNFαR family members appear to have been utilized by viral pathogens. The myxoma virus expresses a secreted protein with homology to TNFαR that is involved in viral virulence (Upton, et al., 1991). In addition, a protein coded by an open reading frame from the Shope fibroma virus is homologous to TNFαR (Smith, et al., 1990). Therefore, an additional feature of understanding these molecules may be in the identification or characterization of novel viruses that utilize functional domains of molecules such as T-BAM to induce immune pathology, for example in autoimmune disease.

REFERENCES

Andersson, J., M. H. Schreier, and F. Melchers. 1980. T-Cell-dependent B-cell stimulation is H-2 restricted and antigen dependent only at the resting B-cell level. *Proc. Natl. Acad. Sci. U. S. A.* 77:1612.

Armitage, R. J., W. C. Fanslow, L. Strockbine, T. A. Sato, K. N. Clifford, B. M. Macduff, D. M. Anderson, S. D. Gimpel, T. Davis-Smith, C. R. Maliszewski, E. A. Clark, C. A. Smith, K. H. Grabstein, D. Cosman, and M. K. Spriggs, 1992. Molecular and biological characterization of a murine ligand for CD40. *Nature* 357:80–82.

Ashman, R. B. and A. Mullbacher. 1979. A T helper cell for anti-viral cytotoxic T-cell responses. *J. Exp. Med.* 150:1277.

Askonas, B. A. and A. R. Williamson. 1972. Factors affecting the propagation of a B cell clone forming antibody to the 2,4-dinitrophenyl group. *Eur. J. Immunol.* 2:487.

Banchereau, J., P. De Paoli, A. Valle, E. Garcia, and F. Rousset. 1991a. Long-term human B cell lines dependent on interleukin-4 and antibody to CD40. *Science* 251:70.

Banchereau, J. and F. Rousset. 1991b. Growing human B lymphocytes in the CD40 system. *Nature* 353:678.

Bank, I., R. A. DePinho, M. B. Brenner, J. Cassimeris, F. W. Alt, and L. Chess. 1986. A functional T3 molecule associated with a novel heterodimer on the surface of immature human thymocytes. *Nature* 322:179.

Barrett, T. B., G. Shu, and E. A. Clark. 1991. CD40 signaling activates CD11a/CD18 (LFA-1)-mediated adhesion in B cells. *J. Immunol.* 146:1722.

Bartlett, W. C., J. McCann, D. M. Shepherd, M. Roy, and R. J. Noelle. 1990. Cognate interactions between helper T cells and B cells. IV. Requirements for the expression of effector phase activity by helper T cells. *J. Immunol.* 145:3956.

Bartlett, W. C., A. Michael, J. McCann, D. Yuan, E. Claassen, and R. . Noelle. 1989. Cognate interactions between helper T cells and B cells. II. Dissection of cognate help by using a class II-restricted, antigen-specific, IL-2-dependent helper T cell clone. *J. Immunol.* 143:1745.

Bennink, J. R. and P. C. Doherty. 1978. Different rules govern help for cytotoxic cells and B cells. *Nature* 276:829.

Bevilacqua, M. P., J. S. Pober, D. L. Mendrick, R. S. Cotran, and M. A. Gimbrone. 1987. Identification of an inducible endothelial-leukocyte adhesion molecule. *Proc. Natl. Acad. Sci. U.S.A.* 84:9238.

Bjorndahl, J. M., S. Nakamura, T. Hara, L. K. Jung, and S. M. Fu. 1988. The 28-kDa/32-kDa activation antigen EA1. Further characterization and signal requirements for its expression. *J. Immunol.* 141:4094.

Borst, J., C. Sluyser, E. De Vries, H. Klein, C. J. Melief, and R. A. van Lier. 1989. Alternative molecular form of human T cell-specific antigen CD27 expressed upon T cell activation. *Eur. J. Immunol.* 19:357.

Brian, A. A. 1988. Stimulation of B-cell proliferation by membrane-associated molecules from activated T cells. *Proc. Natl. Acad. Sci. U. S. A.* 85:564.

Brian, A. A. 1988. Stimulation of B-cell proliferation by membrane-associated molecules from activated T cells. *Proc. Natl. Acad. Sci. U. S. A.* 85:564.

Cambier, J. C. and M. H. Julius. 1988. Early changes in quiescent B cell physiology subsequent to cognate and bystander interaction with helper T cells. *Scand. J. Immunol.* 2759.

Carter, R. H., M. O. Spycher, Y. C. Ng, R. Hoffman, and D. T. Fearon. 1988. Synergistic interaction between complement receptor type 2, and membrane IgM on B lymphocytes. *J. Immunol.* 141:457.

Chao, M. V., M. A. Bothwell, A. H. Ross, H. Koprowski, A. A. Lanahan, C. R. Buck, and A. Sehgal. 1986. Gene transfer and molecular cloning of the human NGF receptor. *Science* 232:518.

Clark, E. A. and J. A. Ledbetter. 1986. Activation of human B cells mediated through two distinct cell surface differentiation antigens, Bp35 and Bp50. *Proc. Natl. Acad. Sci. U. S. A.* 83:4494.

Clark, E. A., T. C. Yip, J. A. Ledbetter, H. Yukawa, H. Kikutani, T. Kishimoto, and M. H. Ng. 1988. CDw40 and BLCa-specific monoclonal antibodies detect two distinct molecules which transmit progression signals to human B lymphocytes. *Eur. J. Immunol.* 18:451.

Clark, E. A., G. L. Shu, B. Luscher, K. E. Draves, J. Banchereau, J. A. Ledbetter, and M. A. Valentine. 1989. Activation of human B cells. Comparison of the signal transduced by IL-4 to four different competence signals. *J. Immunol.* 143:3873.

Clark, E. A. 1990. CD40: a cytokine receptor in search of a ligand. *Tissue Antigens.* 36:33.

Clement, L. T., M. K. Dagg, and G. L. Gartland. 1984. Small, resting B cells can be induced to proliferate by direct signals from activated helper T cells. *J. Immunol.* 132:740.

Camerini, D., G. Walz, W. A. Loenen, J. Borst, and B. Seed. 1991. The T cell activation antigen CD27 is a member of the nerve growth factor/tumor necrosis factor receptor gene family. *J. Immunol.* 147:3165.

Crow, M. K. and H. G. Kunkel. 1985. Activated B lymphocytes: stimulators of an augmented autologous mixed leukocyte reaction. Cell Immunol. 90:555.

Crow, M. K., B. Kushner, J. A. Jovers, S. M. Friedman, S. E. Mechanic, and W. Stohl. 1989. Human peripheral blood T helper cell-induced B cell activation results in B cell surface expression of the CD23 (BLAST-2) antigen. *Cell Immunol.* 121:99.

Crow, M. K., J. A. Jover, and S. M. Friedman. 1986. Direct T helper-B cell interactions induce an early B cell activation antigen. *J. Exp. Med.* 164:1760.

Chestnut, R. W. and H. M. Grey. 1981. Studies on the capacity of B cells to serve as antigen-presenting cells. *J. Immunol.* 126:1075.

Damle, N. K., P. S. Linsley, and J. A. Ledbetter. 1991. Direct helper T cell-induced B cell differentiation involves interation between T cell antigen CD28 and B cell activation antigen B7. *Eur. J. Immunol.* 21:1277.

Doech, H. M., R. K. Schuurman, and E. W. Gelfant. 1980. Polyclonal activation of human lymphocytes in vitro-II. Reappraisal of T and B cell-specific mitogens. *J. Immunol.* 125:827.

DeFranco, A. L., J. D. Ashwell, R. H. Schwartz, and W. E. Paul. 1984. Polyclonal stimulation of resting B lymphocytes by antigen-specific T lymphocytes. *J. Exp. Med.* 159:861.

De Jong, R., W. A. Loenen, M. Brouwer, L. van Emmerik, E. F. de Vries, J. Borst, and R. A. van Lier. 1991. Regulation of expression of CD27, a T cell-specific member of a novel family of membrane receptors. *J. Immunol.* 146:2488.

Dembic, Z., H. Loetscher, U. Gubler, Y. C. Pan, H. W. Lahm, R. Gentz, M. Brockhaus, and W. Lesslauer. 1990. Two human TNF receptors have similar extracellular, but distinct intracellular, domain sequences. *Cytokine.* 2:231.

Depper, J. M., W. J. Leonard, M. Kronke, P. D. Noguchi, R. E., Cunningham, T. A. Waldmann, and W. C. Greene.

1984. Regulation of interleukin 2 receptor expression: effects of phorbol diester, phospholipase C, and reexposure to lectin or antigen. *J. Immunol.* 133:3054.

Doyle, C. and J. L. Strominger. 1987. Interaction between CD4 and class II MHC molecules mediates cell adhesion. *Nature* 330:256.

Durkop, H., U. Latza, M. Hummel, F. Eitelbach, B. Seed, and H. Stein. 1992. Molecular cloning and expression of a new member of the nerve growth factor receptor family that is characteristic for Hodgkin's disease. *Cell* 68:421.

Emilie, D., C. Wallon, P. Galanaud, A. Fischer, D. Olive, and J. F. Delfraissy. 1988. Role of the LFA3-CD2 interaction in human specific B cell differentiation. *J. Immunol.* 141:1912.

Engelmann, H., H. Holtmann, C. Brakebusch, Y. S. Avni, I. Sarov, Y. Nophar, E. Hadas, O. Leitner, and D. Wallach. 1990. Antibodies to a soluble form of a tumor necrosis factor (TNF) receptor have TNF-like activity. *J. Biol. Chem.* 265:14497.

Fan, S. T., A. L. Glasebrook, and T. S. Edgington. 1990. Clonal analysis of CD4+ T helper cell subsets that induce the monocyte procoagulant response. *Cell Immunol.* 128:52.

Fan, S. T. and T. S. Edgington. 1988. Clonal analysis of mechanisms of murine T helper cell collaboration with effector cells of macrophage lineage. *J. Immunol.* 141:1819.

Farrah, T. and C. A. Smith. 992. Emerging cytokine family. *Nature* 358:26.

Friedman, S. M., J. M. Breard, and L. Chess. 1976. Triggering of human peripheral blood B cells: polyclonal induction and modulation of an in vitro PFC response. *J. Immunol.* 117:2021.

Friedman, S. M., M. K. Crow, O. H. Irigoyen, C. Russo, D. N. Posnett, and L. Rogozinski. 1986. Human helper-T-cell function does not require T4 antigen expression. *Cell Immunol.* 103:105.

Goodwin, R. G., D. Anderson, R. Jerzy, T. Davis, C. I. Brannan, N. G. Copeland, N. A. Jenkins, and C. A. Smith. 1991. Molecular cloning and expression of the type 1 and type 2 murine receptors for tumor necrosis factor. *Mol. Cell Biol.* 11:3020.

Goldberg, D., A. Green, A. B. Gottlieb, M. K. Crow, A. Lewison, and S. M. Friedman. 1985. Cloned allospecific human helper T cell lines induce an MHC-restricted proliferative response by resting B cells. *J Immunol.* 135:1012.

Gray, D. and H. Skarvall. 1988. B-cell memory is short-lived in the absence of antigen. *Nature* 336:70.

Gray, D., M. Kosco, and B. Stockinger. 1991. Novel pathways of antigen presentation for the maintenance of memory. *Int. Immunol.* 3:141.

Gray, P. W., K. Barrett, D. Chantry, M. Turner, and M. Feldmann. 1990. Cloning of human tumor necrosis factor (TNF) receptor cDNA and expression of recombinant soluble TNF-binding protein. *Proc. Natl. Acad. Sci. U. S. A.* 87:7380.

Grusby, M. J., R. S. Johnson, V. E. Papaioannou, and L. H. Glimcher. 1991. Depletion of CD4 T cells in major histocompatibility complex class II-deficient mice. *Science* 253:1417.

Hakoshima, T. and K. Tomita. 1988. Crystallization and preliminary X-ray investigation reveals that tumor necrosis factor is a compact trimer furnished with 3-fold symmetry. *J. Mol. Biol.* 201:455.

Hara, T., L. K. Jung, J. M. Bjorndahl, and S. M. Fu. 1986. Human T cell activation. III. Rapid induction of a phosphorylated 28 cD/32 kD disulfide-linked early activation antigen (EA 1) by 12-o-tetradecanoyl phorbol-13-acetate, mitogens, and antigens. *J. Exp. Med.* 164:1988.

Hart, D. N. and J. L. McKenzie. 1988. Isolation and characterization of human tonsil dendritic cells. *J. Exp. Med.* 168:157.

Heller, R. A., K. Song, M. A. Onasch, W. H. Fischer, D. Chang, and G. M. Ringold. 1990. Complementary DNA cloning of a receptor for tumor necrosis factor and demonstration of a shed form of the receptor. *Proc. Natl. Acad. Sci. U. S. A.* 87:6151.

Himmler, A., I. Maurer Fogy, M. Kronke, P. Scheurich, K. Pfizenmaier, M. Lantz, I. Olsson, R. Hauptmann, C. Stratowa, and G. R. Adolf. 1990. Molecular cloning and expression of human and rat tumor necrosis factor receptor chain (p60) and its soluble derivative, tumor necrosis factor-binding protein. *DNA Cell Biol.* 9:705.

Hirohata, S., D. F. Jelinek, and P. E. Lipsky. 1988. T cell-dependent activation of B cell proliferation and differentiation by immobilized monoclonal antibodies to CD3. *J. Immunol.* 140:3736.

Hodgkin, P. D., L. C. Yamashita, R. L. Coffman, and M. R. Kehry. 1990. Separation of events mediating B cell proliferation and Ig production by using T cell membranes and lymphokines. *J. Immunol.* 145:2025.

Inghirami, G., B. Y. Zhu, L. Chess, and D. M. Knowles. 1990. Flow cytometric and immunohistochemical characterization of the gamma/delta T-lymphocyte population in normal human lymphoid tissue and peripheral blood. *Am. J. Pathol.* 136:357.

Inghirami, G., D. R. Foitl, A. Sabichi, B. Y. Zhu, and D. M. Knowles. 1991. Autoantibody-associated cross-reactive idiotype-bearing human B lymphocytes: distribution and characterization, including Ig VH gene and CD5 antigen expression. *Blood* 78:1503.

Itoh, N., S. Yonehara, A. Ishii, M. Yonehara, S. Mzushima, M. Sameshima, A. Hase, Y. Seto, and S. Nagata. 1991. The polypeptide encoded by the cDNA for human cell surface antigen Fas can mediate apoptosis. *Cell* 66:233.

Jackson, D. G. and J. I. Bell. 1990. Isolation of a cDNA encoding the human CD38 (T10) molecule, a cell surface glycoprotein with an unusual discontinuous pattern of expression during lymphocyte differentiation. *J. Immunol.* 144:2811.

Janeway, C. A., S. Carding, B. Jones, J. Murray, P. Portoles, R. Rasmussen, J. Rojo, K. Saizawa, J. West, and K. Bottomly 1988. CD4+ T cells: specificity and function. *Immunol. Rev.* 101:39.

Johnson, D., A. Lanahan, C. R. Buck, A. Sehgal, C. Morgan, E. Mercer, M. Bothwell, and M. Chao. 1986. Expression and structure of the human NGF receptor. *Cell* 47:545.

Jones, B. and C. A. Janeway. 1981. Cooperative interaction of B lymphocytes with antigen-specific helper T lymphocytes is MHC restricted. *Nature* 292:547.

Jover, J. A., E. K. Chartash, B. Kushner, S. M. Friedman, and M. K. Crow. 1989. T helper cell-induced CD23 (BLAST-2) expression: an activation marker for the high density fraction of human B cells. *Clin. Immunol. Immunopathol.* 53:99.

Julius, M. H., J. M. Chiller, and C. L. Sidman. 1982. Major histocompatibility complex-restricted cellular interactions determining B cell activation. *Eur. J. Immunol.* 12:627.

Julius, M. H. and H. G. Rammensee. 1988. T helper cell-dependent induction of resting B cell differentiation need not require cognate cell interaction. *Eur. J. Immunol.* 18:375.

Julius, M. H., H. G. Rammensee, M. J. Ratcliffe, M. C. Lamers, J. Langhorne, and G. Kohler. 1988. The molecular interactions with helper T cells which limit antigen-specific B cell differentiation. *Eur. J. Immunol.* 18:381.

Kast, W. M., A. M. Bronkhorst, L. P. de Waal, and C. J. Melief. 1986. Cooperation between cytotoxic and helper T lymphocytes in protection against lethal Sendai virus infection. Protection by T cells is MHC-restricted and MHC-regulated; a model for MHC-disease associations. *J. Exp. Med.* 164:723.

Katz, D. H., T. Hamaoka, M. E. Dorf, and B. Benacerraf. 1973. Cell interactions between histoincompatible T and B lyphocytes. The H-2 gene complex determines successful physiologic lymphocyte interactions. *Proc. Natl. Acad. Sci. U. S. A.* 70:2624.

Kimata, H., A. Yoshida, C. Ishioka, T. Kusunoki, S. Hosoi, and H. Mikawa. 1991. Nerve growth factor specifically induces human IgG4 production. *Eur. J. Immunol.* 21:137.

Kirchevsky, A., E. G. Armstrong, J. Schlatterer, S. Birken, J. O'Connor, K. Bikel, S. Silverberg, J. W. Lustbader, and R. E. Canfield. 1988. Preparation and characterization of antibodies to the urinary fragment of the human chorionic gonadotropin beta-subunit. *Endocrinology* 123:584.

Ko, H. S., S. M. Fu, R. J. Winchester, D. T. Yu, and H. G. Kunkel. 1979. Ia determinatns on stimulated human T lymphocytes. Occurrence on mitogen- and antigen-activated T cells. *J. Exp. Med.* 150:246.

Krensky, A. M., C. Clayberger, C. S. Reiss, J. L. Strominger, and S. J. Burakoff. 1982. Specificity of OKT4+ cytotoxic T lymphocyte clones. *J. Immunol.* 129:2001.

Krusemeier, M. and E. C. Snow. 1988. Induction of lymphokine responsiveness of hapten-specific B lymphocytes promoted through an antigen-mediated T helper lymphocyte interaction. *J. Immunol.* 140:367.

Kubota, E., D. T. McKenzie, R. W. Dutton, and S. L. Swain. 1991. Role of T cells in the B-cell response: glutaraldehyde-fixed T-helper hybridoma cells synergize with the lymphokines IL-4 to induce B-cell activation and proliferation. *Immunology.* 72:40.

Kupfer, A. and S. J. Singer. 1989. Cell biology of cytotoxic and helper T cell functions: immunofluorescence microscopic studies of single cells and cell couples. *Annu. Rev. Immunol.* 7:309.

Kupfer, A., S. L. Swain, and S. J. Sinner. 1987. The specific direct interaction of helper T cells and antigen-presenting B cells. II. Reorienrtation of the microtubule organizing center and reorganization of the membrane-associated cytoskeleton inside the bound helper T cells. *J. Exp. Med.* 165:1565.

Ledbetter, J. A., G. Shu, M. Gallagher, and E. A. Clark. 1987. Augmentation of normal and malignant B cell proliferation by monoclonal antibody to the B cell-specific antigen BP50 (CDW40). *J. Immunol.* 138:788.

Ledbetter, J. A. and E. A. Clark. 1986. Surface phenotype and function of tonsillar germinal center and mantle zone B cell subsets. *Hum. Immunol.* 15:30.

Lederman, S., M. J. Yellin, A. Krichevsky, J. Belko, J. J. Lee, and L. Chess. 1992. Identification of a novel surface protein on activated CD4+ T cells that induces contact dependent B cell differentiation (help) *J. Exp. Med.* 175:1091.

Leist, T. P., M. Kohler, and R. M. Zinkernagel. 1989. Impaired generation of anti-viral cytotoxicity against lymphocytic choriomeningitis and vaccinia virus in mice treated with CD4-specific monoclonal antibody. *Scand. J. Immunol.* 30:679.

Lewis, M., L. A. Tartaglia, A. Lee, G. L. Bennett, G. C. Rice, G. H. Wong, E. Y. Chen, and D. V. Goeddel. 1991. Cloning and expression of cDNAs for two distinct murine tumor necrosis factor receptors demonstrate one receptor is species specific. *Proc. Natl. Acad. Sci. U. S. A.* 88:2830.

Linsley, P. S., E. A. Clark, and J. A. Ledbetter. 1990. T-cell antigen CD28 mediates adhesion with B cells by interacting with activation antigen B7/BB-1. *Proc. Natl. Acad. Sci. U.S.A.* 87:5031.

Liu, Y. J., D. E. Joshua, G. T. Williams, C. A. Smith, J. Gordon, and I. C. MacLennan. 1989. Mechanism of antigen-driven selection in germinal centres. *Nature* 342:929.

Liu, Y-J., G. D. Johnson, J. Gordon, and I. C. M. MacLennan. 1992. Germinal centers in T-cell-dependent antibody responses. *Immunol. Today* 13:17.

Liu, Y. J., J. A. Cairns, M. J. Holder, S. D. Abbot, K. U. Jansen, J. Y. Bonnefoy, J. Gordon, and I. C. MacLennan. 1991. Recombinant. 25-kDa CD23 and interleukin 1 alpha promote the survival of germinal center B cells: evidence for bifurcation in the development of centrocytes rescued from apoptosis. *Eur. J. Immunol.* 21:1107.

Loenen, W. A., E. De Vries, L. A. Gravestein, R. Q. Hintzen, R. A. van Lier, and J. Borst. 1992. The CD27 membrane receptor, a lymphocyte-specific member of the nerve growth factor receptor family, gives rise to a soluble form by protein processing that does not involve receptor endocytosis. *Eur. J. Immunol.* 22:447.

Loetscher, H., Y. C. Pan, H. W. Lahm, R. Gentz, M. Brockhaus, H. Tabuchi, and W. Lesslauer. 1990. Molecular cloning and expression of the human 55 kd tumor necrosis factor receptor. *Cell* 61:351.

Lohoff, M., M. Dirks, P. Rohwer, and M. Rollinghoff. 1989. Studies on the mechanism of polyclonal B cell stimulation by Th2 cells. *Eur. J. Immunol.* 1977.

Mallett, S., S. Fossum, and A. N. Barclay. 1990. Characterization of the MRC OX40 antigen of activated CD4 positive T lymphocytes—a molecule related to nerve growth factor receptor. *EMBO J.* 9:1063.

Martin, P. J., J. A. Ledbetter, Y. Morishita, C. H. June, P. G. Beatty, and J. A. Hansen. 1986. A 44 kilodalton cell surface homodimer regulates interleukin 2 production by activated human T lymphocytes. *J. Immunol.* 136:3282.

Martinez, A. C. and A. Coutinho. 1981. B-cell activation is a two step process. *Nature* 290:60.

McDonald, N. Q., R. Lapatto, J. Murray Rust, J. Gunning, A. Wlodawer, and T. L. Blundell. 1991. New protein fold revealed by a 2.3-A resolution crystal structure of nerve growth factor. *Nature* 354:411.

Mitchell, G. F. and J. F. Miller. 1968. Cell to cell interaction in the immune response. II. The source of hemolysin-forming cells in irradiated mice given bone marrow and thymus or thoracic duct lymphocytes. *J. Exp. Med.* 128:821.

Mitchison, N. A. 1971. The carrier effect in the secondary response to hapten-protein conjugates. V. Use of antilymphocyte serum to deplete animals of helper cells. *Eur. J. Immunol.* 1:68.

Nemerow, G. R., M. E. McNaughton, and N. R. Cooper. 1985. Binding of monoclonal antibody to the Epstein Barr virus (EBV)/CR2 receptor induces activation and differentiation of human B lymphocytes. *J. Immunol.* 135:3068.

Noelle, R. J., J. Daum, W. C. Bartlett, J. McCann, and D. M. Shepherd. 1991. Cognate interactions between helper T cells and B cells. V. Reconstitution of T helper cell function using purified plasma membranes from activated Th1 and Th2 helper cells and lymphokines. *J. Immunol.* 46:1118.

Noelle, R. J., M. Roy, D. M. Shepherd, I. Stamenkovic, J. A. Ledbetter, and A. Aruffo. 1992. A 39-kDa protein on activated helper T cells binds CD40 and transduces the signal for cognate activation of B cells. *Proc. Natl. Acad. Sci. U. S. A.* 89:6550.

Noelle, R. J. and E. C. Snow. 1990. Cognate interactions between helper T cells and B cells. Immunol. Today 11:361.

Noelle, R. J. and E. C. Snow. 1991. T helper cell-dependent B cell activation. *FASEB J.* 5:2770.

Noelle, R. J., J. McCann, L. Marshall, and W. C. Bartlett. 1989. Cognate interactions between helper T cells and B cells. III. Contact-dependent, lymphokine-independent induction of B cell cycle entry by activated helper T cells. *J. Immunol.* 143:1807.

Noelle, R. J., E. C. Snow, J. W. Uhr, and E. S. Vitetta. 1983. Activation of antigen-specific B cells: role of T cells, cytokines, and antigen in induction of growth and differentiation. *Proc. Natl. Acad. Sci. U.S.A.* 80:6628.

Nophar, Y., O. Kemper, C. Brakebusch, H. Englemann, R. Zwang, D. Aderka, H. Holtmann, and D. Wallach. 1990. Soluble forms of tumor necrosis factor receptors (TNF-Rs). The cDNA for the type I TNF-R, cloned using amino acid sequence data of its soluble form, encodes both the cell surface and a soluble form of the receptor. *EMBO J.* 9:3269.

Nossal, G. J. 1992. The molecular and cellular basis of affinity maturation in the antibody response. *Cell* 68:1.

O'Brien, R. L., P. Marrack, U. Storb, and J. W. Kappler. 1988. B cells expressing Ig transgenes respond to a T-dependent antigen only in the presence of Ia-compatible T cells. *J. Immunol.* 141:3335.

Oehm, A., Behrmann, I., Falk, W., Paulita, M., Maier, G., Klas, C., Li-Weber, M., Richards, S., Dhein, J., Trauth, B. C., et al. 1992 Purification and molecular cloning of the APO-1 cell surface antigen, a member of the Tumor Necrosis Factor/Never Growth Factor Receptor Superfamily. Sequence Identity with the Fas Antigen. *J. Biol. Chem.* 267(15):10709.

Otten, U., P. Ehrhard, and R. Peck. 1989. Nerve growth factor induces growth and differentiation of human B lymphocytes. *Proc. Natl. Acad. Sci. U. S. A.* 86:10059.

Owens, T. 1988. A noncognate interaction with anti-receptor antibody-activated helper T cells induces small resting murine B cells to proliferate and to secrete antibody. *Eur. J. Immunol.* 18:395.

Paterson, D. J., W. A. Jefferies, J. R. Green, M. R. Brandon, P. Corthesy, M. Puklavec, and A. F. Williams. 1987. Antigens of activated rat T lymphocytes including a molecule of 50,000 Mr detected only on CD4 positive T blasts. *Mol. immunol.* 24:1281.

Poo, W. J., L. Conrad, and C. A. Janeway. 1988. Receptor-directed focusing of lymphokine release by helper T cells. *Nature* 332:378.

Pollok, K. E., V. O'Brien, L. Marshall, J. W. Olson, R. J. Noelle, and E. C. Snow. 1991. The development of competence in resting B cells. The induction of cyclic AMP and ornithine decarboxylase activity after direct contact between B and T helper cells. *J. Immunol.* 146:1633.

Principato, M. A., G. S. Thompson, and S. M. Friedman. 1983. A cloned major histocompatibility complex-restricted trinitrophenyl-reactive human helper T cell line that activates B cell subsets via two distinct pathways. *J. Exp. Med.* 158:1444.

Rabin, E. M., J. Ohara, and W. E. Paul. 1985. B-cell stimulatory factor 1 activates resting B cells. Proc. Natl. Acad. Sci. U. S. A. 82:2935.

Rahemtulla, A., W. P. Fung-Leung, M. W. Schilham, T. M. Kundig, S. R. Sambhara, A. Narendran, A. Arabian, A. Wakeham, C. J. Paige, R. M. Zinkernagel, R. G. Miller, and T. W. Mak. 1991. Normal development and function of CD8$^+$ cells but markedly decreased helper cell activity in mice lacking CD4. *Nature* 353:180.

Reinherz, E. L., P. C. Kung, G. Goldstein, and S. F. Schlossman. 1979. Separation of functional subsets of human T cells by a monoclonal antibody. *Proc. Natl. Acad. Sci. U. S. A.* 76:4061.

Reinherz, E. L., P. C. Kung, J. M. Breard, G. Goldstein, and S. F. Schlossman. 1980. T cell requirements for generation of helper factor(s) in man: analysis of the subsets involved. J. Immunol. 124:1883.

Reinherz, E. L., P. C. Kung, J. M. Pesando, J. Ritz, G. Goldstein, and S. F. Schlossman. 1979. Ia determinants on human T-cell subsets defined by monoclonal antibody. Activation stimuli required for expression. *J. Exp. Med.* 150:1472.

Riedel, C., T. Owens, and G. J. Nossal. 1988. A significant proportion of normal resting B cells are induced to secrete immunoglobulin through contact with anti-receptor antibody-activated helper T cells in clonal cultures. *Eur. J. Immunol.* 18:403.

Risso, A., D. Smilovich, M. C. Capra, I. Baldissarro, G., Yan, A. Bargellesi, and M. E. Cosulich. 1991. CD69 in resting and activated T lymphocytes. Its association with a GTP binding protein and biochemical requirements for its expression. *J. Immunol.* 146:4105.

Rogozinski, L., A. Bass, E. Glickman, M. A. Talle, G. Goldstein, J. Wang, L. Chess, and Y. Thomas. 1984. The T4 surface antigen is involved in the induction of helper function. *J. Immunol.* 126:735.

Rothe, J. G., M. Brockhaus, R. Gentz, and W. Lesslauer. 1991. Molecular cloning and expression of the mouse Tnf receptor type b. *Immunogenetics* 34:338.

Rothlein, R., M. L. Dustin, S. D. Marlin, and T. A. Springer. 1986. A human intercellular adhesion molecule (ICAM-1) distinct from. LFA-1. *J. Immunol.* 137:1270.

Sanchez Madrid, F., A. M. Krensky, C. F. Ware, E. Robbins, J. L. Strominger, S. J. Burakoff, and T. A. Springer. 1982. Three distinct antigens associated with human T-lymphocyte-mediated cytolysis: LFA-1, LFA-2, and LFA-3. *Proc. Natl. Acad. Sci. U.S.A.* 79:7489.

Sanders, V. M., J. M. Snyder, J. W. Uhr, and E. S. Vitetta. 1986. Characterization of the physical interaction between antigen-specific B and T cells. *J. Immunol.* 137:2395.

Sanders, V. M. and E. S Vitetta. 1991. B cell-associated LFA-1 and T cell-associated ICAM-1 transiently cluster in the area of contact between interacting cells. *Cell Immunol.* 132:45.

Sehgal, A., M. Bothwell, and M. Chao. 1989. Gene transfer of truncated NGF receptor clones leads to cell surface expression in mouse fibroblasts. *Nucleic. Acids. Res.* 17:5623.

Sekita, K., C. Straub, D. Hoessli, and R. H. Zubler. 1988. B cell-stimulating activity of lymphoid cell membrane fractions. *Eur. J. Immunol.* 18:1405.

Sen, J., P. Bossu, S. J. Burakoff, and A. K. Abbas. 1992. T cell surface molecules regulating noncognate B lymphocyte activation. Role of CD2 and LFA-1. *J. Immunol.* 148:1037.

Shields, J. G., R. J. Armitage, B. N. Jamieson, P. C. Beverley, and R. E. Callard. 1989. Increased expression of surface IgM but not IgD or IgG on human B cells in response to IL-4. *Immunology* 66:224.

Siegel, J. P. and H. S. Mostowski. 1990. A bioassay for the measurement of human interleukin-4. *J. Immunol. Methods* 132:287.

Smith, S. H. M. H. Brown, D. Rowe, R E. Callard, and P. C. Beverley. 1986. Functional subsets of human helper-inducer cells defined by a new monoclonal antibody, UCHL1. *Immunology* 58:63.

Smith, R. A. and C. Baglioni. 1987. The active form of tumor necrosis factor is a trimer. *J. Biol. Chem.* 262:6951.

Smith, C. A., A. Davis, D. Anderson., L. Sclam, M. P. Beckmann, R. Jerzy, S. K. Dower, D. Cosman, and R. G. Goodwin. 1990. A receptor for tumor necrosis factor defines an unusual family of cellular and viral proteins. *Science* 248:1019.

Snow, E. C., R. J. Noelle, J. W. Uhr, and E. S. Vitetta. 1983. Activation of antigen-enriched B cells. II. Role of linked recognition in B cell proliferation to thymus-dependent antigens. *J. Immunol.* 130:614.

Spiegel, H., H. Herbst, G. Niedobitek, H. D. Foss, and H. Stein. 1992. Follicular dendritic cells are a major reservoir for human immunodeficiency virus type 1 in lymphoid tissues facilitating infection of CD4+ T-helper cells. *Am. J. Pathol.* 140:15.

Sprent, J. 1978a. Restricted helper function of F1 hybrid T cells positively selected to heterlogous erythrocytes in irradiated parental strain mice. II. Evidence for restrictions affecting helper cell induction and T-B collaboration, both mapping to the K-end of the H-2 complex. *J. Exp. Med.* 147:1159.

Sprent, J. 1978b. Role of H-2 gene products in the function of T helper cells from normal and chimeric mice in vivo. *Immunol. Rev.* 42:108.

Stamenkovic, I., D. Sgroi, A. Aruffo, M. S. Sy, and T. Anderson. 1991. The B lymphocyte adhesion molecule CD22 interacts with leukocyte common antigen CD45RO on T cells and alpha2-6 sialyltransferase, CD75, on B cells. *Cell* 66:1133.

Stamenkovic, I., E. A. Clark, and B. Seed. 1989. A B-lymphocyte activation molecule related to the nerve growth factor receptor and induced by cytokines in carcinomas. *EMBO J.* 8:1403.

Tesch, H., F. I. Smith, W. J. Muller Hermes, and K. Rajewsky. 1984. Heterogeneous and monoclonal helper T cells induce similar anti-(4-hydroxy-3-nitrophenyl)acetyl (NP) antibody populations in the primary adoptive response. I. Isotype distribution. *Eur. J. Immunol.* 4:188.

Thomas, Y., J. Sosman, L. Rogozinski, O. Irigoyen, P. C. Kung, G. Goldstein, and L. Chess. 1981. Functional analysis of human T cell subsets defined by monoclonal antibodies. III. Regulation of helper factor production by T cell subsets. *J. Immunol.* 126:1948.

Thomas, T., L. Rogozinski, O. H. Irigoyen, S. M. Friedman, P. C. Kung, G. Goldstein, and L. Chess. 1981. Functional analysis of human T cell subsets defined by monoclonal antibodies. IV. Induction of suppressor cells within the OKT4+ population. *J. Exp. Med.* 154:459.

Thomas, Y., J. Sosman, O. Irigoyen, S. M. Friedman, P. C. Kung, G. Goldstein, and L. Chess. 1980. Functional analysis of human T cell subsets defined by monoclonal antibodies. I. Collaborative T-T interactions in the immunoregulation of B cell differentiation. *J. Immunol.* 125:2402.

Thomas, Y., L. Rogozinski, O. H. Irigoyen, H. H. Shen, M. A. Talle, G. Goldstein, and L. Chess. 1982. Functional analysis of human T cell subsets defined by monoclonal antibodies. V. Suppressor cells within the activated OKT4+ population belong to a distinct subset. *J. Immunol.* 128:1386.

Thompson, C. B., M. E. Schaefer, F. D. Finkelman, I. Scher, J. Farrar, and J.. J. Mond. 1985. T cell-derived B cell growth factor(s) can induce stimulation of both resting and activated B cells. *J. Immunol.* 134:369.

Tohma, S., S. Hirohata, and P. E. Lipsky. 1991. The role of CD11a/CD18-CD54 interactions in human T cell-dependent B cell activation. *J. Immunol.* 146:492.

Tohma, S. and P. E. Lipsky. 1991. Analysis of the mechanism of T cell-dependent polyclonal activation of human B cells. Induction of human B cell responses by fixed activated T cells. *J. Immunol.* 146:2544.

Torimoto, Y., K. Sugita, D. S. Weinberg, N. H. Dang, C. Donahue, N. L. Letvin, S. F. Schlossman, and C. Morimoto. 1991. Development of a monoclonal antibody, anti-6C2, which is involved in the interaction of CD4 T helper cells and activated B cells. *J. Immunol.* 146:2176.

Umiel, T., L. M. Nadler, I. J. Cohen, H. Levine, B. Stark, Z. Mammon, M. Dzaldetti, G. Rechavi, F. Simoni, and N. Katzir. 1987. Undifferentiated leukemia of infancy with t(11:17) chromosomal rearrangement. Coexpressing myeloid and B cell restricted antigens. *Cancer* 59:1143.

Upton, C., J. L. Macen, M. Schreiber, and G. McFadden. 1991. Myxoma virus expresses a secreted protein with homology to the tumor necrosis factor receptor gene family that contributes to viral virulence. *Virology* 184:370.

Van de Velde, H., I. Von Hoegen, W. Luc, J. R. Parnes, and K. Theilemans. 1991. The B-cell surface protein CD72/Lyb-2 is the ligand for CD5. *Nature* 351:662.

Vitetta, E. S., R. Fernandez Botran, C. D. Myers, and V. M. Sanders. 1989. Cellular interactions in the humoral immune response. *Adv. Immunol.* 45:1.

Wasik, M. A., R. P. Donnelly, and D. I. Beller. 1988. Lymphokine-independent induction of macrophage membrane IL-1 by autoreactive T cells recognizing either class I or class II MHC determinants. *J. Immunol.* 141:3456.

Watanabe F., R., C. I. Brannan, N. G. Copeland, N. A. Jenkins, and S. Nagata. 1992. Lymphoproliferation disorder in mice explained by defects in Fas antigen that mediates apoptosis. *Nature* 356:314.

Weaver, C. T., L. M. Duncan, and E. R. Unanue. 1989. T cell induction of macrophage IL-1 during antigen presentation. Characterization of a lymphokine mediator and comparison of TH1 and TH2 subsets. *J. Immunol.* 142:3469.

Weigert, M. G., I. M. Cesari, S. J. Yonkovich, and M. Cohn. 1970. Variability in the lambda light chain sequences of mouse antibody. *Nature* 228:1045.

Whalen, B. J., H. P. Tony, and D. C. Parker. 1988. Characterization of the effector mechanism of help for antigen-presenting and bystander resting B cell growth mediated by Ia-restricted Th2 helper T cell lines. *J. Immunol.* 141:2230.

White, R. A., Mason, D. W. Mason, A. F. Williams, G. Galfre, and C. Milstein. 1978. T-lymphocyte heterogeneity in the rat: separation of functional subpopulations using a monoclonal antibody. *J. Exp. Med.* 148:664.

Yellin, M. J., J. J. Lee, L. Chess, and S. Lederman. 1991. A human CD4$^-$ leukemic subclone with contact dependent helper function. *J. Immunol.* 147:3389.

Yamada, H., P. J. Martin, M. A. Bean, M. P. Braun, P. G. Beatty, K. Sadamoto, and J. A. Hansen. 1985. Monoclonal antibody 9.3 and anti-CD11 antibodies define reciprocal subsets of lymphocytes. *Eur. J. Immunol.* 15:1164.

Yonehara, S., A. Ishii, and M. Yonehara. 1989. A cell-killing monoclonal antibody (anti-Fas) to a cell surface antigen co-downregulated with the receptor of tumor necrosis factor. *J. Exp. Med.* 169:1747.

Zimecki, M., Z. Wieczorek, J. A. Kapp, and C. W. Pierce. 1988. Secretion of interleukin 1 (IL-1) by peritoneal macrophages upon contact with syngeneic T cells is Ia-restricted and antigen-independent process. *Arch. Immunol. Ther. Exp.* (*Warsz*). 36:661.

Zimecki, M., Z. Wieczorek, J. A. Kapp, and C. W. Pierce. 1989. Structures on T cells and macrophages involved in interleukin 1 (Il-1) secretion by macrophages upon contact with syngeneic thymocytes. *Arch. Immunol. Ther. Exp.* (*Warsz*). 37:587.

Zinkernagel, R. M. 1976. T helpers may be sensitized by antigen-specifically altered structures, which are coded by the I region of the H-2 gene complex. *Adv. Exp. Med. Biol.* 66:527.

Zinkernagel, R. M., G. N. Callahan, A. Althage, S. Cooper, J. W. Streilein, and J. Klein. 1978. The lymphoreticular system in triggering virus plus self-specific cytotoxic T cells: evidence for T help. *J. Exp. Med.* 147:897.

What is claimed is:

1. A method of inhibiting an autoimmune response in a human suffering from an autoimmune disease selected from the group consisting of psoriasis, Lyme disease and hyper IgE syndrome which comprises administering to the human, in an amount effective to treat the autoimmune disease, an antibody that binds specifically to a protein to which monoclonal antibody 5c8 produced by the hybridoma having ATCC Accession No. HB 10916 specifically binds.

2. The method of claim 1, wherein the autoimmune disease is psoriasis.

3. The method of claim 1, wherein the autoimmune disease is Lyme disease.

4. The method of claim 1, wherein the autoimmune disease is hyper IgE syndrome.

5. The method of claim 1 wherein the antibody is a monoclonal antibody.

6. The method of claim 1, wherein the antibody is monoclonal antibody 5c8 produced by the hybridoma having ATCC Accession No. HB 10916.

7. The method of claim 1, wherein the antibody is conjugated to a therapeutic agent.

8. The method of claim 7, wherein the therapeutic agent is selected from the group consisting of; radioisotopes, toxins, toxoids, and chemotherapeutic agents.

9. The method of claim 1, wherein the antibody is administered in a pharmaceutically acceptable carrier.

10. The method of claim 9, wherein the carrier comprises buffered saline, physiological saline, water, or a water/oil emulsion.

11. The method of claim 9, wherein the antibody is administered by intravenous, intraperitoneal, or intramuscular administration.

12. The method of claim 1, wherein the antibody is a monoclonal antibody.

13. The method of claim 1, wherein the antibody is a chimeric antibody.

14. The method of claim 1, wherein the antibody is a humanized antibody.

15. The method of claim 1, wherein the antibody is a murine antibody.

16. The method of claim 1, wherein the antibody is a human antibody.

* * * * *